United States Patent
Mori et al.

(10) Patent No.: US 11,814,638 B2
(45) Date of Patent: Nov. 14, 2023

(54) **MARKER ASSOCIATED WITH SMUT RESISTANCE IN PLANT BELONGING TO GENUS *SACCHARUM* AND USE THEREOF**

(71) Applicant: TOYOTA JIDOSHA KABUSHIKI KAISHA, Toyota (JP)

(72) Inventors: Masaaki Mori, Okazaki (JP); Tatsuro Kimura, Kariya (JP); Hiroyuki Enoki, Hamamatsu (JP); Yusuke Ueta, Miyoshi (JP); Takeo Sakaigaichi, Miyakonojo (JP); Yusuke Tarumoto, Koshi (JP); Minoru Tanaka, Tsukuba (JP); Katsuki Adachi, Nishinoomote (JP); Taichiro Hattori, Nishinoomote (JP); Makoto Umeda, Nishinoomote (JP); Michiko Hayano, Nishinoomote (JP)

(73) Assignee: TOYOTA JIDOSHA KABUSHIKI KAISHA, Toyota (JP)

( * ) Notice: Subject to any disclaimer, the term of this patent is extended or adjusted under 35 U.S.C. 154(b) by 0 days.

(21) Appl. No.: 17/257,453

(22) PCT Filed: Jul. 2, 2019

(86) PCT No.: PCT/JP2019/026324
§ 371 (c)(1),
(2) Date: Dec. 31, 2020

(87) PCT Pub. No.: WO2020/009113
PCT Pub. Date: Jan. 9, 2020

(65) Prior Publication Data
US 2021/0139929 A1    May 13, 2021

(30) Foreign Application Priority Data

Jul. 3, 2018  (JP) ................................ 2018-127142
Oct. 19, 2018 (JP) ................................ 2018-197546
Jul. 1, 2019  (JP) ................................ 2019-122913

(51) Int. Cl.
C12Q 1/6895  (2018.01)
A01H 1/04    (2006.01)
A01H 1/00    (2006.01)
C12N 15/82   (2006.01)

(52) U.S. Cl.
CPC ......... *C12N 15/8282* (2013.01); *A01H 1/045* (2021.01); *A01H 1/1255* (2021.01); *C12Q 1/6895* (2013.01); *C12Q 2600/156* (2013.01)

(58) Field of Classification Search
None
See application file for complete search history.

(56) References Cited

U.S. PATENT DOCUMENTS

| | | | |
|---|---|---|---|
| 8,519,223 B2 | 8/2013 | Taguchi et al. | |
| 9,758,841 B2 | 9/2017 | Enoki et al. | |
| 2010/0138950 A1 | 6/2010 | Ragot | |
| 2014/0230100 A1* | 8/2014 | Enoki ................ | A01H 1/04 800/298 |
| 2017/0327907 A1 | 11/2017 | Enoki et al. | |

FOREIGN PATENT DOCUMENTS

| | | |
|---|---|---|
| JP | 2010-516236 A | 5/2010 |
| JP | 2012-235772 A | 12/2012 |
| WO | 2007/125958 A1 | 11/2007 |
| WO | 2012/147635 A1 | 11/2012 |

OTHER PUBLICATIONS

Butterfield, 2007, PhD thesis "Marker Assisted Breeding in Sugarcane: A Complex Polyploid", University of Stellenbosch, pp. 1-75.*
Aitken et al, 2014, BMC Genomics 15:152.*
Piperidis et al, 2020, Plant J. 103:2039-2061.*
Thirugnanasambandam et al, 2018, Front. Plant Sci. 9:616. doi: 10.3389/fpls.2018.00616.*
Y.-B. Pan et al., "Molecular Genotyping of Sugarcane Clones With Microsatellite DNA Markers", Maydica, 2003, pp. 319-329, vol. 48.
Nathalie Piperidis et al., "Comparative genetics in sugarcane enables structured map enhancement and validation of marker-trait associations", Molecular Breeding, Feb. 2008, pp. 233-247, vol. 21.
Khan et al., "Development of an RAPD-based SCAR marker for smut disease resistance in commercial sugarcane cultivars of Pakistan", Crop Protection, vol. 94, 2017, pp. 166-172.
Raboin et al., "Undertaking Genetic Mapping of Sugarcane Smut Resistance", Proc S Air Sug Technol Ass, vol. 75, 2001, pp. 94-98.
Liping Xu et al., "Identification of Rapd Marker Linked To S Mut Resistance Gene in Sugarcane", Chin J Appl Environ Biol, 2004, vol. 10, No. 3, pp. 263-267 (5 pages total).
Hai-lian Ji et al., "Comparative QTL Mapping of Resistance to *Sporisorium reiliana* in Maize Based on Meta-analysis of QTL Locations", Journal of Plant Genetic Resources, 2007, vol. 8, No. 2, pp. 132-139 (8 pages total).

* cited by examiner

*Primary Examiner* — Anne Kubelik
(74) *Attorney, Agent, or Firm* — Sughrue Mion, PLLC

(57) ABSTRACT

This invention is intended to evaluate smut resistance with higher accuracy using a marker associated with sugarcane smut resistance, which consists of a continuous nucleic acid region existing in a region between the nucleotide sequence as shown in SEQ ID NO: 1 and the nucleotide sequence as shown in SEQ ID NO: 6, a region between the nucleotide sequence as shown in SEQ ID NO: 135 and the nucleotide sequence as shown in SEQ ID NO: 143, or a region between the nucleotide sequence as shown in SEQ ID NO: 144 or 145 and the nucleotide sequence as shown in SEQ ID NO: 151 of a sugarcane chromosome.

6 Claims, 27 Drawing Sheets
Specification includes a Sequence Listing.

MARKER ASSOCIATED WITH SMUT RESISTANCE IN PLANT BELONGING TO GENUS *SACCHARUM* AND USE THEREOF

CROSS REFERENCE TO RELATED APPLICATIONS

This application is a National Stage of International Application No. PCT/JP2019/026324 filed Jul. 2, 2019, claiming priority based on Japanese Patent Application No. 2018-127142 filed Jul. 3, 2018, Japanese Patent Application No. 2018-197546 filed Oct. 19, 2018 and Japanese Patent Application No. 2019-122913 filed Jul. 1, 2019.

TECHNICAL FIELD

The present invention relates to a marker associated with smut resistance that enables selection of a sugarcane line resistant to smut and a method for using the same.

BACKGROUND ART

Sugarcane has been cultivated for edible use such as a raw material for sugar, liquor, and the like. In addition, sugarcane has been used in a variety of industrial fields, including the use thereof as a raw material for biofuel. Under such circumstances, there is a need to develop novel sugarcane varieties having desirable characteristics (e.g., sugar content, enhanced vegetative capacity, sprouting capacity, disease resistance, insect resistance, cold resistance, an increase in leaf blade length, an increase in leaf area, and an increase in stalk length).

In general, there are three methods for identification of a plant variety/line: that is, "characteristics comparison" for comparison of characteristics data; "comparison during cultivation" for comparison of plants cultivated under the same conditions; and "DNA assay" for DNA analysis. There are many problems in line identification by means of characteristics comparison or comparison during cultivation, such as lowered precision due to differences in cultivation conditions and long-term field research that requires a number of steps. In particular, sugarcane plants are much larger than other graminaceous crops such as rice and maize, and it is thus difficult to conduct line identification through field research.

In order to identify a variety resistant to a certain disease, in addition, it is necessary to carry out an inoculation test using a causative microorganism of a disease after long-term cultivation of sugarcane and then collect disease resistance data by observing lesions and the like. When the test is carried out, however, it is necessary to prevent the causative microorganism from propagation to an external environment more definitely and provide facilities, such as a large-scale special-purpose greenhouse, a special-purpose field, or a facility isolated from an external environment. In order to prepare a novel sugarcane variety, in addition, tens of thousands of hybrids are first prepared via crossing, followed by seedling selection and stepwise selection of elite lines. Eventually, 2 or 3 types of candidate novel varieties having desirable characteristics can be obtained. For preparation of a novel sugarcane variety, as described above, it is necessary to cultivate and evaluate an enormous number of lines, and it is also necessary to prepare the large-scale greenhouse or field as described above and make time-consuming efforts.

Therefore, it has been required to develop a method for identification of a sugarcane line having disease resistance with the use of markers present in the sugarcane genome. If markers excellent in a variety of characteristics could be used for production of a novel sugarcane variety, in particular, various problems peculiar to sugarcane as described above would be resolved, and the markers would be able to serve as very effective tools. However, sugarcane plants have a large number of chromosomes (approximately 100 to 130) due to higher polyploidy, and the development of marker technology has been thus slow. In the case of sugarcane, the USDA reported genotyping with the use of SSR markers (Non-Patent Literature 1), although precision of genotyping is low because of the small numbers of markers and polymorphisms in each marker. In addition, the above genotyping is available only for American/Australian varieties, and it cannot be used for identification of major varieties cultivated in Japan, Taiwan, India, and other countries and lines serving as useful genetic resources.

In addition, Non-Patent Literature 2 suggests the possibility that a sugarcane genetic map can be prepared by increasing the number of markers, comparing individual markers in terms of a characteristic relation, and verifying the results. However, Non-Patent Literature 2 does not disclose a sufficient number of markers, and markers linked to characteristics of interest have not been found.

As disclosed in Patent Literature 1, a marker associated with black root rot resistance in sugar beet is known as a marker associated with disease resistance. Patent Literature 2 also discloses a technique of selecting a *Zea mays* variety using a maker linked to a trait of interest.

Meanwhile, causative microorganisms of sugarcane smut have high-level infectivity, and, therefore, the onset of smut results in immediate infection of the entire field. Sugarcane crops affected with smut cannot be used as raw material for sugar production, and, in addition, such affected crops would wither and die. Therefore, development of smut will cause a significant decline in yield in the following year and later. Damage due to smut has been reported in 28 or more countries, including Brazil, U.S.A., Australia, China, and Indonesia. Smut can be prevented by sterilization treatment at the time of planting; however, preventive effects are limited to the early growth period. Thus, cultivation of a sugarcane variety imparted with smut resistance has been awaited.

Patent Literature 3 discloses markers linked to smut resistance that were discovered by preparing many sugarcane plant markers and conducting linkage analysis of quantitative traits along with such markers for hybrid progeny lines.

CITATION LIST

Non Patent Literature

Non Patent Literature 1: Maydica 48, 2003, 319-329, "Molecular genotyping of sugarcane clones with microsatellite DNA markers"

Non Patent Literature 2: Nathalie Piperidis et al., Molecular Breeding, 2008, Vol. 21, 233-247

Patent Literature

Patent Literature 1: WO 2007/125958
Patent Literature 2: JP 2010-516236 A
Patent Literature 3: WO 2012/147635

SUMMARY OF INVENTION

Technical Problem

While Patent Literature 3 discloses markers linked to smut resistance, development of smut resistance markers exhibiting higher association with smut resistance had been awaited. Under the above circumstances, the present invention is intended to provide an improved smut resistance marker exhibiting higher association with smut resistance.

Solution to Problem

The present inventors have conducted intensive studies to achieve the object. The present inventors prepared many markers of particular sugarcane varieties and conducted linkage analysis of quantitative traits along with such markers for hybrid progeny lines. Accordingly, the present inventors found markers linked to quantitative traits such as smut resistance. This has led to the completion of the present invention.

The present invention encompasses the following.

(1) A marker associated with sugarcane smut resistance, which consists of a continuous nucleic acid region existing in a region between the nucleotide sequence as shown in SEQ ID NO: 1 and the nucleotide sequence as shown in SEQ ID NO: 6, a region between the nucleotide sequence as shown in SEQ ID NO: 135 and the nucleotide sequence as shown in SEQ ID NO: 143, or a region between the nucleotide sequence as shown in SEQ ID NO: 144 or 145 and the nucleotide sequence as shown in SEQ ID NO: 151 of a sugarcane chromosome.

(2) The marker associated with sugarcane smut resistance according to (1), wherein the nucleic acid region comprises any nucleotide sequence selected from the group consisting of the nucleotide sequences as shown in SEQ ID NOs: 1 to 6, 135 to 143, and 144 to 151 or a part of the nucleotide sequence.

(3) The marker associated with sugarcane smut resistance according to (1), wherein the nucleic acid region comprises the nucleotide sequence as shown in SEQ ID NO: 1 or 2 of a sugarcane chromosome or a part of the nucleotide sequence.

(4) The marker associated with sugarcane smut resistance according to (1), wherein the nucleic acid region comprises any nucleotide sequence selected from the group consisting of the nucleotide sequences as shown in SEQ ID NOs: 138 to 140 of a sugarcane chromosome or a part of the nucleotide sequence.

(5) The marker associated with sugarcane smut resistance according to (1), wherein the nucleic acid region comprises a nucleotide sequence as shown in SEQ ID NO: 149 or 151 of a sugarcane chromosome or a part of the nucleotide sequence.

(6) The marker associated with sugarcane smut resistance according to (1), wherein the nucleic acid region comprises any nucleotide sequence selected from the group consisting of the nucleotide sequences as shown in SEQ ID NOs: 298, 303, 307, 311, and 316 of a sugarcane chromosome or a part of the nucleotide sequence.

(7) A method for producing a sugarcane line having improved smut resistance comprising: a step of extracting a chromosome of a progeny plant obtained from parent plants, at least one of which is a sugarcane plant, and/or a chromosome of a parent sugarcane plant; and a step of determining the presence or absence of the marker associated with sugarcane smut resistance according to any one of (1) to (6) in the obtained chromosome.

(8) The method for producing a sugarcane line according to (7), wherein the step of determination involves the use of a DNA chip comprising a probe corresponding to the marker associated with sugarcane smut resistance.

(9) The method for producing a sugarcane line according to (7), wherein the progeny plant is a seed or young seedling and the chromosome is extracted from the seed or young seedling.

This description includes part or all of the content as disclosed in the descriptions and/or drawings of Japanese Patent Application Nos. 2018-127142, 2018-197546, and 2019-122913, which are priority documents of the present application.

Advantageous Effects of Invention

The present invention can provide a novel marker associated with sugarcane smut resistance that is linked particularly to smut resistance among various sugarcane quantitative traits. With the use of the marker associated with sugarcane smut resistance of the present invention, smut resistance of hybrid sugarcane progeny lines can be tested. Thus, a sugarcane variety with improved smut resistance can be identified in a very cost-effective manner.

BRIEF DESCRIPTION OF DRAWINGS

FIG. 1(A) the results of calculation of the morbidity of smut of a progeny line resulting from crossbreeding between "KY08-6023" and "JW90"; FIG. 1(B) the results of calculation of the morbidity of smut of a progeny line resulting from crossbreeding between "KY08-6039" and "JW90"; and FIG. 1(C) the results of calculation of the morbidity of smut of a progeny line resulting from crossbreeding between "KY08-6041" and "JW90".

DESCRIPTION OF EMBODIMENTS

Figure 1:
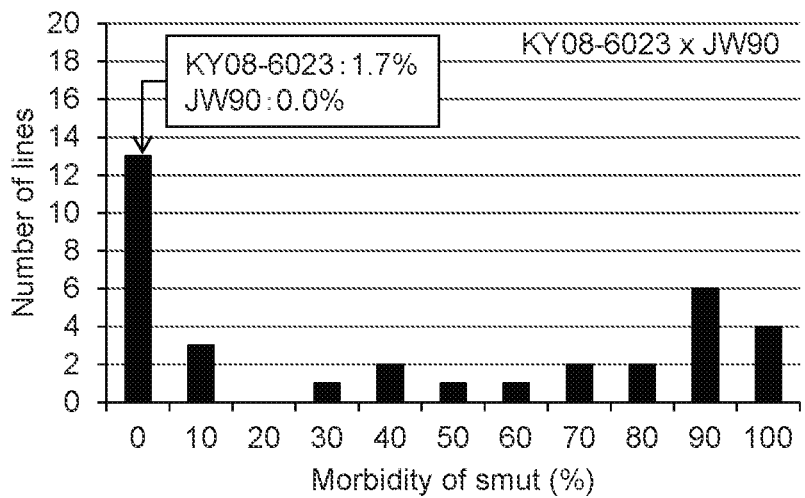
FIGS. 1(A)-1(C) show characteristic diagrams showing.
Figure 1:
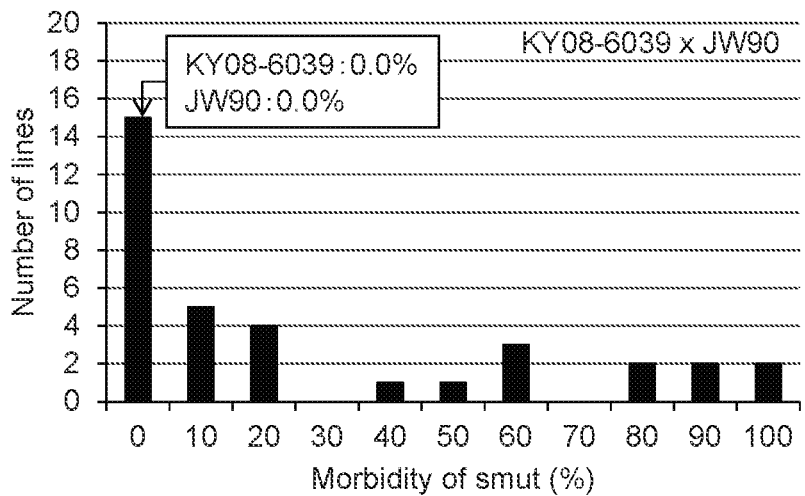
Figure 1:
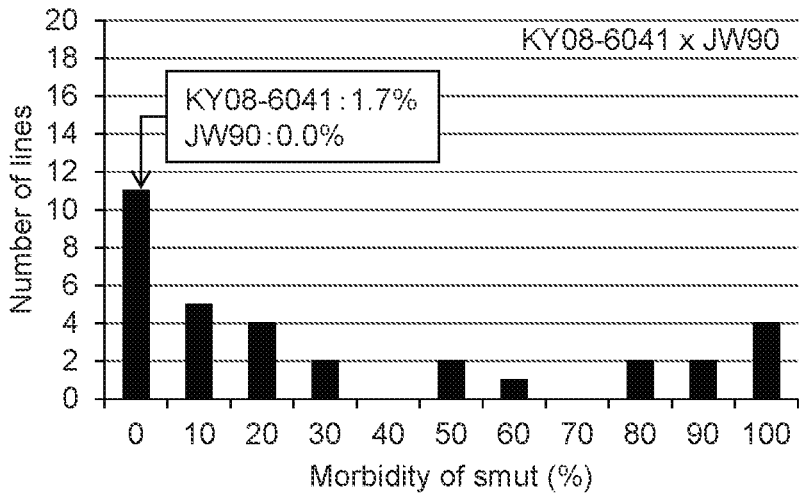

The marker associated with sugarcane smut resistance according to the present invention and the method for using the same are described below. In particular, a method for producing a sugarcane line using a marker associated with sugarcane smut resistance is described.

[Markers Associated with Sugarcane Smut Resistance]

The marker associated with sugarcane smut resistance of the present invention is a particular region present on a sugarcane chromosome, it is linked to a causative gene (or a group of causative genes) for a trait of sugarcane smut resistance, and it can be thus used for identification of a trait of sugarcane smut resistance. Therefore, whether or not a progeny line obtained with the use of a known sugarcane line has a trait of improving smut resistance can be determined by confirming the presence or absence of the marker associated with sugarcane smut resistance in such progeny line. In the present invention, the term "smut" refers to a disease characterized by lesion formation due to infection with a microorganism of the genus *Ustilago*. One example of a microorganism of the genus *Ustilago* is *Ustilago scitaminea*.

In addition, the term "marker associated with sugarcane smut resistance" refers to a marker linked to a causal gene (or a group of causative genes) of a trait of improving smut resistance. In the presence of the marker of interest in a certain sugarcane variety, for example, such sugarcane variety can be determined to have improved smut resistance.

The term "sugarcane" used herein refers to a plant belonging to the genus *Saccharum* of the family Poaceae. In addition, the term "sugarcane" includes so-called noble cane (scientific name: *Saccharum officinarum*) and wild cane (scientific name: *Saccharum spontaneum*), *Saccharum barberi, Saccharum sinense*, and the earlier species of *Saccharum officinarum* (*Saccharum robustum*). The term "known sugarcane variety/line" is not particularly limited. It includes any variety/line usable in Japan and any variety/line used outside Japan. Examples of sugarcane varieties cultivated in Japan include, but are not particularly limited to, Ni1, NiN2, NiF3, NiF4, NiF5, Ni6, NiN7, NiF8, Ni9, NiTn10, Ni11, Ni12, Ni14, Ni15, Ni16, Ni17, NiTn19, NiTn20, Ni22, and Ni23. Examples of major sugarcane varieties used in Japan include, but are not particularly limited to, NiF8, Ni9, NiTn10, and Ni15. Further, examples of major sugarcane varieties that have been introduced into Japan include, but are not limited to, F177, Nco310, and F172. In addition, sugarcane varieties and lines are wild-type varieties with excellent disease resistance, and wild-type varieties with excellent smut resistance are used. Examples of wild-type varieties with excellent smut resistance include, but are not particularly limited to, JW90, Iriomote 15, and Iriomote 8.

In addition, a progeny line may be a line obtained by crossing a maternal plant and a paternal plant of the same species, each of which is a sugarcane variety/line, or it may be a hybrid line obtained from parent plants when one thereof is a sugarcane variety/line and the other is a closely related variety/line (*Erianthus arundinaceus*). In addition, a progeny line may be obtained by so-called backcrossing. In particular, both or either the maternal line and the paternal line is preferably a wild-type variety with excellent smut resistance, such as JW90, Iriomote 15, or Iriomote 8.

Example of Markers Associated with Sugarcane Smut Resistance 1

The marker associated with sugarcane smut resistance was newly identified by quantitative trait loci (QTL) analysis using a genetic linkage map comprising 86 linkage groups including 31,191 markers (4,503 thereof are derived from JW90) originally obtained from sugarcane chromosomes and the sugarcane smut resistance data. In addition, many genes are presumably associated with sugarcane smut resistance, which is a quantitative trait characterized by a continuous distribution. That is, sugarcane smut resistance is evaluated based on the morbidity of smut characterized by such continuous distribution. For QTL analysis, the QTL Cartographer gene analysis software (Wang S., C. J. Basten, and Z.-B. Zeng, 2010; Windows QTL Cartographer 2.5, Department of Statistics, North Carolina State University, Raleigh, N.C.) is used, and the analysis is carried out by the composite interval mapping (CIM) method.

Specifically, a region included in the above genetic linkage map with LOD scores equivalent to or exceeding a given threshold (e.g., 2.5); i.e., a region of approximately 8.4 cM (centimorgan), was identified by the QTL analysis described above. The term "morgan (M)" used herein refers to a unit representing the relative distance between genes on a chromosome, and it expresses the crossover rate in percent figures. In the case of a sugarcane chromosome, 1 cM corresponds to approximately 2,000 kb. In addition, it is suggested that a causative gene (or a group of causative genes) for a trait that improves smut resistance could be present at the peak position or in the vicinity thereof.

The 8.4 cM region comprises 6 types of markers listed in Table 1 in the order shown therein and it is linked to a trait of improving smut resistance.

TABLE 1

| Varity | Linkage group | Position (cM) | Range (cM) | Adjacent marker | LOD value | Effects (%) |
|---|---|---|---|---|---|---|
| JW90 | 42 | 0.0 | 8.4 | AMP0121265 (SEQ ID NO: 1)-AMP0120752 (SEQ ID NO: 2)-<br>AMP0035185 (SEQ ID NO: 3)-AMP0114852 (SEQ ID NO: 4)-<br>AMP0089904 (SEQ ID NO: 5)-AMP0100370 (SEQ ID NO: 6) | 24.5 | −47.2 |

In Table 1, "Linkage group" represents the number given to each group among a plurality of linkage groups specified by QTL analysis. In Table 1, the name of the marker provided in the column indicating adjacent markers represents the name given to each marker originally obtained in the present invention.

In addition, the peak included in the 8.4 cM region is present adjacent to the marker comprising the nucleotide sequence as shown in SEQ ID NO: 1 (AMP0121265).

A continuous nucleic acid region existing in the 8.4 cM region containing markers shown in Table 1 can be used as a marker associated with sugarcane smut resistance. The term "nucleic acid region" used herein refers to a region comprising a nucleotide sequence having 95% or less, preferably 90% or less, more preferably 80% or less, and most preferably 70% or less identity to a different region present on a sugarcane chromosome. If the identity of a nucleic acid region serving as a marker associated with sugarcane smut resistance to a different region falls within the above range, the nucleic acid region can be specifically detected in accordance with a conventional technique. The identity value described herein can be calculated using, for example, BLAST® with default parameter settings.

The nucleic acid region serving as a marker associated with sugarcane smut resistance can comprise 8 or more, preferably 15 or more, more preferably 20 or more, and most preferably 30 nucleotides. If the length of the nucleic acid region serving as a marker associated with sugarcane smut resistance falls within the above range, the nucleic acid region can be specifically detected in accordance with a conventional technique.

The marker associated with sugarcane smut resistance may be any continuous nucleic acid region selected from the 8.4 cM region. The nucleotide sequence of the 8.4 cM region can be identified by flanking sequence analysis such as inverse PCR analysis using primers designed based on the nucleotide sequences as shown in SEQ ID NOs: 1 to 6.

In particular, the marker associated with sugarcane smut resistance is preferably selected from a region adjacent to the nucleotide sequence as shown in SEQ ID NO: 1 or 2 in the 8.4 cM region described above because of the presence of the peak adjacent to the nucleotide sequence as shown in SEQ ID NO: 1.

The 6 types of the markers or some thereof can be used as the marker associated with sugarcane smut resistance. Specifically, one or more markers selected from among the 6 types of markers can be used as the markers associated with sugarcane smut resistance. Alternatively, a partial region of the 6 types of markers can be used as the marker associated with sugarcane smut resistance.

Example of the Marker Associated with Sugarcane Smut Resistance 2

The marker associated with sugarcane smut resistance was newly identified by quantitative trait loci (QTL) analysis using a genetic linkage map of progeny plants of Iriomote 15 comprising 58 linkage groups including 64,757 markers (1,166 thereof are derived from progeny plants of Iriomote 15) originally obtained from sugarcane chromosomes and the sugarcane smut resistance data. In addition, many genes are presumably associated with sugarcane smut resistance, which is a quantitative trait characterized by a continuous distribution. That is, sugarcane smut resistance is evaluated based on the morbidity of smut characterized by such continuous distribution. For QTL analysis, the QTL Cartographer gene analysis software (Wang S., C. J. Basten, and Z.-B. Zeng, 2010; Windows QTL Cartographer 2.5. Department of Statistics, North Carolina State University, Raleigh, N.C.) is used, and the analysis is carried out by the composite interval mapping (CIM) method.

Specifically, a region included in the above genetic linkage map with LOD scores equivalent to or exceeding a given threshold (e.g., 2.5); i.e., a region of approximately 26.6 cM (centimorgan), was identified by the QTL analysis described above. The term "morgan (M)" used herein refers to a unit representing the relative distance between genes on a chromosome, and it expresses the crossover rate in percent figures. In the case of a sugarcane chromosome, 1 cM corresponds to approximately 2,000 kb. In addition, it is suggested that a causative gene (or a group of causative genes) for a trait that improves smut resistance could be present at the peak position or in the vicinity thereof.

The 26.6 cM region comprises 9 types of markers listed in Table 2 in the order shown therein and it is linked to a trait of improving smut resistance.

TABLE 2

| Varity | Linkage group | Position (cM) | Range (cM) | Adjacent marker | LOD value | Effects (%) |
|---|---|---|---|---|---|---|
| Iriomote 15 | 15 | 25.7 | 26.6 | AMP0014532 (SEQ ID NO: 135)-AMP0043152 (SEQ ID NO: 136)-<br>AMP0069135 (SEQ ID NO: 137)-AMP0032477 (SEQ ID NO: 138)-<br>AMP0018405 (SEQ ID NO: 139)-AMP0002312 (SEQ ID NO: 140)-<br>AMP0007121 (SEQ ID NO: 141)-AMP0090106 (SEQ ID NO: 142)-<br>AMP0015886 (SEQ ID NO: 143) | 11.5 | −37.8 |

In Table 2, "Linkage group" represents the number given to each group among a plurality of linkage groups specified by QTL analysis. In Table 2, the name of the marker provided in the column indicating adjacent markers represents the name given to each marker originally obtained in the present invention.

In addition, the peak included in the 26.6 cM region is present in a position between the marker comprising the nucleotide sequence as shown in SEQ ID NO: 138 (AMP0032477) and the marker comprising the nucleotide sequence as shown in SEQ ID NO: 140 (AMP002312). In particular, the peak is present adjacent to the marker comprising the nucleotide sequence as shown in SEQ ID NO: 139 (AMP0018405).

A continuous nucleic acid region existing in the 26.6 cM region containing markers shown in Table 2 can be used as a marker associated with sugarcane smut resistance. The term "nucleic acid region" used herein refers to a region comprising a nucleotide sequence having 95% or less, preferably 90% or less, more preferably 80% or less, and most preferably 70% or less identity to a different region present on a sugarcane chromosome. If the identity of a nucleic acid region serving as a marker associated with sugarcane smut resistance to a different region falls within the above range, the nucleic acid region can be specifically detected in accordance with a conventional technique. The identity value described herein can be calculated using, for example, BLAST® with default parameter settings.

The nucleic acid region serving as a marker associated with sugarcane smut resistance can comprise 8 or more, preferably 15 or more, more preferably 20 or more, and most preferably 30 nucleotides. If the length of the nucleic acid region serving as a marker associated with sugarcane smut resistance falls within the above range, the nucleic acid region can be specifically detected in accordance with a conventional technique.

The marker associated with sugarcane smut resistance may be any continuous nucleic acid region selected from the 26.6 cM region. The nucleotide sequence of the 26.6 cM region can be identified by flanking sequence analysis such as inverse PCR analysis using primers designed based on the nucleotide sequences as shown in SEQ ID NOs: 135 to 143.

In particular, the marker associated with sugarcane smut resistance is preferably selected from the region between the nucleotide sequence as shown in SEQ ID NO: 138 and the nucleotide sequence as shown in SEQ ID NO: 140 in the 26.6 cM region described above. In addition, the marker associated with sugarcane smut resistance is preferably selected from the region comprising the nucleotide sequence as shown in SEQ ID NO: 139 and a nucleotide sequence adjacent to the nucleotide sequence as shown in SEQ ID NO: 139 in the 26.6 cM region described above. The marker is preferably selected in such manner because of the presence of the peak in the region between the nucleotide sequence as shown in SEQ ID NO: 138 and the nucleotide sequence as shown in SEQ ID NO: 140, which is adjacent to the nucleotide sequence as shown in SEQ ID NO: 139.

The 9 types of the markers or some thereof can be used as the markers associated with sugarcane smut resistance. Specifically, one or more markers selected from among the 9 types of markers can be used as the markers associated with sugarcane smut resistance. Alternatively, a partial region of the 9 types of markers can be used as the marker associated with sugarcane smut resistance.

Example of Markers Associated with Sugarcane Smut Resistance 3

The marker associated with sugarcane smut resistance was newly identified by quantitative trait loci (QTL) analysis using a genetic linkage map derived from the progeny line "KY09-6092" of Iriomote 8 comprising 117 linkage groups including 57,444 markers (2,936 thereof are derived from the progeny line "KY09-6092" of Iriomote 8) originally obtained from sugarcane chromosomes and the sugarcane smut resistance data.

In addition, many genes are presumably associated with sugarcane smut resistance, which is a quantitative trait characterized by a continuous distribution. That is, sugarcane smut resistance is evaluated based on the morbidity of smut characterized by such continuous distribution. For QTL analysis, the QTL Cartographer gene analysis software (Wang S., C. J. Basten, and Z.-B. Zeng, 2010; Windows QTL Cartographer 2.5. Department of Statistics. North Carolina State University, Raleigh, N.C.) is used, and the analysis is carried out by the composite interval mapping (CIM) method.

Specifically, a region included in the above genetic linkage map with LOD scores equivalent to or exceeding a given threshold (e.g., 2.5); i.e., a region of approximately 12.27 cM (centimorgan), was identified by the QTL analysis described above. The term "morgan (M)" used herein refers to a unit representing the relative distance between genes on a chromosome, and it expresses the crossover rate in percent figures. In the case of a sugarcane chromosome, 1 cM corresponds to approximately 2,000 kb. In addition, it is suggested that a causative gene (or a group of causative genes) for a trait that improves smut resistance could be present at the peak position or in the vicinity thereof.

The 12.27 cM region comprises 7 types of markers listed in Table 3 in the order shown therein and it is linked to a trait of improving smut resistance.

TABLE 3

| Varity | Linkage group | Position (cM) | Range (cM) | Adjacent marker | LOD value | Effects (%) |
|---|---|---|---|---|---|---|
| Iriomote 8 | 8 | 83.8 | 12.27 | AMP0063683 (SEQ ID NOs: 144, 145)-<br>AMP0082090 (SEQ ID NO: 146)-AMP0013802 (SEQ ID NO: 147)-<br>AMP0083204 (SEQ ID NO: 148)-AMP0043774 (SEQ ID NO: 149)-<br>AMP0094596 (SEQ ID NO: 150)-AMP0091501 (SEQ ID NO: 151) | 68.7 | −54.2 |

In Table 3, "Linkage group" represents the number given to each group among a plurality of linkage groups specified by QTL analysis. In Table 3, the name of the marker provided in the column indicating adjacent markers represents the name given to each marker originally obtained in the present invention. Among the markers shown in Table 3, AMP0063683 is a nucleic acid region comprising the nucleotide sequence as shown in SEQ ID NO: 144 and the nucleotide sequence as shown in SEQ ID NO: 145 at both ends. Markers other than AMP0063683 are each a nucleic acid region comprising a single nucleotide sequence.

In addition, the peak included in the 12.27 cM region is present adjacent to the marker comprising the nucleotide sequence as shown in SEQ ID NO: 151 (AMP0091501).

A continuous nucleic acid region existing in the 12.27 cM region containing markers shown in Table 3 can be used as a marker associated with sugarcane smut resistance. The term "nucleic acid region" used herein refers to a region comprising a nucleotide sequence having 95% or less, preferably 90% or less, more preferably 80% or less, and most preferably 70% or less identity to a different region present on a sugarcane chromosome. If the identity of a nucleic acid region serving as a marker associated with sugarcane smut resistance to a different region falls within the above range, the nucleic acid region can be specifically detected in accordance with a conventional technique. The identity value described herein can be calculated using, for example, BLAST® with default parameter settings.

The nucleic acid region serving as a marker associated with sugarcane smut resistance can comprise 8 or more, preferably 15 or more, more preferably 20 or more, and most preferably 30 nucleotides. If the length of the nucleic acid region serving as a marker associated with sugarcane smut resistance falls within the above range, the nucleic acid region can be specifically detected in accordance with a conventional technique.

The marker associated with sugarcane smut resistance may be any continuous nucleic acid region selected from the 12.27 cM region. The nucleotide sequence of the 12.27 cM region can be identified by flanking sequence analysis such as inverse PCR analysis using primers designed based on the nucleotide sequences as shown in SEQ ID NOs: 144 to 151.

In particular, the marker associated with sugarcane smut resistance is preferably selected from a region between the nucleotide sequence as shown in SEQ ID NO: 150 and the nucleotide sequence as shown in SEQ ID NO: 151 in the 12.27 cM region described above because of the presence of the peak adjacent to the nucleotide sequence as shown in SEQ ID NO: 151.

The 7 types of the markers or some thereof can be used as the marker associated with sugarcane smut resistance. Specifically, one or more markers selected from among the 7 types of markers can be used as the markers associated with sugarcane smut resistance. Alternatively, a partial region of the 7 types of markers can be used as the marker associated with sugarcane smut resistance.

A part of the 12.27 cM region comprising the markers shown in Table 3 comprises a partial region in common with a part of the 8.4 cM region comprising the markers shown in Table 1. Specifically, the nucleotide sequence of a region in the vicinity of the peak included in the 12.27 cM region is in common with the nucleotide sequence of a region in the vicinity of the peak included in the 8.4 cM region. More specifically, the nucleotide sequence of an adjacent region comprising AMP0121265 located at 0 cM among the markers associated with sugarcane smut resistance derived from JW90 shown in Table 1 is in common with the nucleotide sequence of an adjacent region comprising AMP0091501 located at 83.76 cM among the markers associated with sugarcane smut resistance derived from Iriomote 8 shown in Table 3. Accordingly, it is highly likely that the regions comprising the common nucleotide sequence comprises a factor (e.g., a causative gene) that improves sugarcane smut resistance. It is more preferable that such regions be used as the markers associated with sugarcane smut resistance.

[Sugarcane Marker Identification]

As described above, markers associated with sugarcane smut resistance were identified from among 31,191 markers originally obtained from sugarcane chromosomes (4,503 markers thereof are derived from JW90), 64,757 markers originally obtained from sugarcane chromosomes (1,166 markers thereof are derived from the progeny lines "KY08-6023," "KY08-6039," and "KY08-6041" of Iriomote 15), and 57,444 markers originally obtained from sugarcane chromosomes (2,936 markers thereof are derived from the progeny line "KY09-6092" of Iriomote 8) in the present invention. The 31,191 markers (4,503 markers thereof are derived from JW90), the 64,757 markers (1,166 markers thereof are derived from the progeny lines "KY08-6023," "KY08-6039," and "KY08-6041" of Iriomote 15), and the 57,444 markers (2,936 markers thereof are derived from the progeny line "KY09-6092" of Iriomote 8) are described herein. When identifying these markers, a DNA library was prepared in accordance with the method for preparing a DNA library disclosed in WO 2018/003220.

Specifically, a nucleic acid amplification reaction is carried out in a reaction solution in which a primer comprising an arbitrary nucleotide sequence (hereafter, referred to as a "random primer") is adjusted at high concentration, and the amplified nucleic acid fragments are served as a DNA library. Here, the term "high concentration" refers to higher concentration than the primer concentration in a conventional nucleic acid amplification reaction. Specifically, the method for preparing a DNA library according to the present invention involves the use of a random primer at higher concentration than the primer concentration in a conventional nucleic acid amplification reaction. As a template included in the reaction solution, genomic DNA prepared from an organism, the DNA library of which is to be prepared, can be used.

The sequence of the random primer is not particularly limited. For example, a nucleotide comprising 9 to 30 bases can be used. In particular, a random primer is a nucleotide comprising an arbitrary sequence of 9 to 30 bases. A nucleotide type (a sequence type) is not particularly limited, and 1 or more types of nucleotides, preferably 1 to 10,000 types of nucleotides, more preferably 1 to 1,000 types of nucleotides, further preferably 1 to 100 types of nucleotides, and most preferably 1 to % types of nucleotides may be used. With the use of nucleotides (a group of nucleotides) within the range described above as a random primer, amplified nucleic acid fragments can be obtained with higher reproducibility. When a random primer comprises a plurality of nucleotides, it is not necessary that all nucleotides comprise the same number of bases (9 to 30 bases), and a random primer may comprise a plurality of nucleotides of a different number of bases.

In order to obtain a particular amplicon via a nucleic acid amplification reaction, in general, nucleotide sequences of primers are designed in accordance with the amplicon of interest. For example, a pair of primers is designed to flank the position corresponding to the amplicon in template DNA, such as genomic DNA. In such a case, primers are designed to hybridize to a specific region in the template, and it can thus be referred to as "specific primers."

Unlike a primer designed to obtain a particular amplicon, in contrast, a random primer is not designed to hybridize to a specific region in template DNA, but it is designed to obtain a random amplicon. A random primer may comprise any nucleotide sequence. It accidentally hybridizes to a complementary region in template DNA and it can thus be involved in random amplicon amplification.

Specifically, a random primer can be a nucleotide comprising an arbitrary sequence involved in random amplicon amplification, as described above. An arbitrary sequence is not particularly limited. For example, it may be designed as a nucleotide sequence of nucleotides randomly selected from the group consisting of adenine, guanine, cytosine, and thymine, or it may be designed as a particular nucleotide sequence. Examples of particular nucleotide sequences include a nucleotide sequence comprising a restriction enzyme recognition sequence or a nucleotide sequence comprising an adaptor sequence applied to a next-generation sequencer.

When a plurality of types of nucleotides are designed as random primers, a plurality of nucleotide sequences of given length can be designed by randomly selecting nucleotides from the group consisting of adenine, guanine, cytosine, and thymine. When a plurality of types of nucleotides are designed as random primers, alternatively, a plurality of nucleotide sequences each comprising a common region composed of a particular nucleotide sequence and an uncommon region composed of an arbitrary nucleotide sequence can be designed. An uncommon region may be composed of a nucleotide sequence of nucleotides randomly selected from the group consisting of adenine, guanine, cytosine, and thymine. Alternatively, an uncommon region may comprise all of the 4 types of nucleotides; i.e., adenine, guanine, cytosine, and thymine, or some thereof. A common region is not particularly limited, and it may be composed of any nucleotide sequence. For example, a common region can be a nucleotide sequence comprising a restriction enzyme recognition sequence, a nucleotide sequence comprising an adaptor sequence applied to a next-generation sequencer, or a nucleotide sequence that is common among a particular gene family.

When a plurality of nucleotide sequences of given length are designed by randomly selecting nucleotides from among 4 types of nucleotides as a plurality of random primers, a plurality of nucleotide sequences are preferably designed to have 70% or lower, preferably 60% or lower, more preferably 50% or lower, and most preferably 40% or lower identity in regions constituting 30% or more, preferably 50% or more, more preferably 70% or more, and further preferably 90% or more of the entire sequences. When a plurality of nucleotide sequences of given length are designed by randomly selecting nucleotides from among 4 types of nucleotides as a plurality of random primers, the nucleotide sequences are designed to comprise the nucleotides having the identity within the range described above. Thus, amplified fragments can be obtained over the entire genomic DNA of the target organism species. That is, homogeneity of amplified fragments can be enhanced.

When a plurality of nucleotide sequences each comprising a common region composed of a particular nucleotide sequence and an uncommon region composed of an arbitrary nucleotide sequence are designed as a plurality of random primers, for example, several 3'-terminal nucleotides can be designed as an uncommon region, and remaining 5'-terminal nucleotides can be designed as a common region. If the "n" number of 3'-terminal nucleotides is designated as an uncommon region, $4^n$ types of random primers can be designed. The number "n" can be 1 to 5, preferably 2 to 4, and more preferably 2 or 3.

As random primers each comprising a common region and an uncommon region, for example, 16 types of random primers each comprising a 5'-terminal adaptor sequence applied to a next-generation sequencer (a common region) and a 3'-terminal region of 2 nucleotides (an uncommon region) can be designed in total. When a 3'-terminal region is designed to comprise 3 nucleotides (an uncommon region), 64 types of random primers can be designed in total. As the types of random primers are increased, amplified fragments can be more extensively obtained throughout the entire genomic DNA of the target organism species. When designing a random primer comprising a common region and an uncommon region, accordingly, it is preferable that a 3'-terminal region comprise 3 nucleotides.

Alternatively, 64 types of nucleotide sequences each comprising a common region and an uncommon region of 3 nucleotides may be first designed, and up to 63 types of random primers selected from among the 64 types of nucleotide sequences may then be used. In other words, use of up to 63 types of random primers can occasionally yield results of analysis conducted by a nucleic acid amplification reaction or with the use of a next-generation sequencer superior to those attained with the use of all of 64 types of random primers.

It is preferable that random primer concentration be adequately determined in accordance with a base length of the random primer. When a plurality of types of nucleotides with different base length are used as random primers, the base length of the random primer can be the average (it may be a simple average or weight average by taking the amount of nucleotides into consideration).

Specifically, a nucleic acid amplification reaction is carried out with the use of a random primer with a 9 to 30 base length at 4 to 200 microM, and preferably at 4 to 100 microM. Under such conditions, many amplified fragments, and, in particular, many amplified fragments of 100 to 500 base length, can be obtained with high reproducibility via a nucleic acid amplification reaction.

More specifically, random primer concentration is preferably 40 to 60 microM when a random primer is of 9 to 10 base length. When a random primer is of 10 to 14 base length, random primer concentration is preferably at a level that satisfies $y>3E+08x^{-6.974}$ and 100 microM or lower, provided that "y" represents the base length of the random primer and "x" represents random primer concentration. When a random primer is of 14 to 18 base length, random primer concentration is preferably 4 to 100 microM. When a random primer is of 18 to 28 base length, it is preferable that random primer concentration be 4 microM or higher and satisfies $y<8E+08x^{-5.533}$. When a random primer is of 28 to 29 base length, random primer concentration is preferably 6 to 10 microM. By adjusting the random primer concentration at the level described above in accordance with the base length of the random primer, many amplified fragments can be obtained more definitely while achieving high reproducibility.

The inequations described above; i.e., $y>3E+08x^{-6.974}$ and $y<8E+08x^{-5.533}$, were formed as a result of thorough investigation of the correlation between the length and the concentration of a random primer as described in WO 2018/003220, so that many DNA fragments of 100 to 500 base length can be amplified with high reproducibility.

The amount of genomic DNA used as a template in a nucleic acid amplification reaction is not particularly limited. When the amount of the reaction solution is 50 microliters, the amount of genomic DNA is preferably 0.1 to 1,000 ng, more preferably 1 to 500 ng, further preferably 5 to 200 ng, and most preferably 10 to 100 ng. By adjusting the amount of genomic DNA used as a template in such range, an amplification reaction from the random primer would not be inhibited, and many amplified fragments can be obtained with high reproducibility.

In accordance with the method described above, a DNA library can be produced from sugarcane with excellent smut resistance, and a DNA library can be produced from sugarcane with smut susceptibility. The nucleotide sequences in these DNA libraries are analyzed with the use of a next-generation sequencer, the read number of fragments constituting the library is compared with each other, and fragments peculiar to the DNA library produced from sugarcane with excellent smut resistance can be selected.

More specifically, the present inventors subjected a wild-type sugarcane line (Iriomote 15) to crossbreeding with a known sugarcane variety (NiF8) to obtain progeny lines (3 lines), subjected the obtained progeny lines to crossbreeding with the wild-type sugarcane line (JW90) to obtain progeny lines (33 lines, 35 line, and 35 lines, respectively), and prepared a DNA library thereof. The resulting DNA library was applied to a next-generation sequencer to obtain the read number data, the genotype data were obtained therefrom, and position information of the marker in the chromosome was determined based on the genotype data using the AntMap software for constructing genetic linkage maps (Iwata H, Ninomiya S, 2006, AntMap: Constructing genetic linkage maps using an ant colony optimization algorithm, Breed Sci., 56: 371-378) in accordance with the Kosambi's genetic distance formula. Further, a genetic map datasheet was prepared based on the obtained marker position information using Mapmaker/EXP ver. 3.0 (A Whitehead Institute for Biomedical Research Technical Report. Third Edition, January, 1993). As a result, the 31,191 markers including the aforementioned 6 types of markers associated with sugarcane smut resistance shown in SEQ ID NOs: 1 to 6 were identified. In addition, the step of obtaining the read number data by applying the DNA library to the next-generation sequencer was repeated two times to obtain a larger amount of the read number data, and the genotype data were obtained from the read number data. Thus, 64,757 markers including 9 types of the markers associated with sugarcane smut resistance as shown in SEQ ID NOs: 135 to 143 were identified in the same manner.

In addition, the present inventors subjected a wild-type sugarcane line (Iriomote 8) to crossbreeding with a known sugarcane variety (NiF8) to obtain progeny lines, subjected a sugarcane variety "NiTn18" to crossbreeding with a sugarcane variety "NiTn24" to obtain progeny lines, obtained 154 progeny lines therefrom, and prepared a DNA library thereof. The resulting DNA library was applied to a next-generation sequencer to obtain the read number data, the genotype data were obtained therefrom, and position information of the marker in the chromosome was determined based on the genotype data using the AntMap software for constructing genetic linkage maps (Iwata H, Ninomiya S, 2006, AntMap: Constructing genetic linkage maps using an ant colony optimization algorithm, Breed Sci., 56: 371-377) in accordance with the Kosambi's genetic distance formula. Further, a genetic map datasheet was prepared based on the obtained marker position information using Mapmaker/EXP ver. 3.0 (A Whitehead Institute for Biomedical Research Technical Report, Third Edition, January, 1993). As a result, 57,444 markers including 7 types of the markers associated with sugarcane smut resistance as shown in SEQ ID NOs: 144 (and 145) to 151 indicated above were identified.

The adjacent region comprising the marker associated with sugarcane smut resistance having the nucleotide sequence as shown in SEQ ID NO: 151 and the adjacent region comprising the marker associated with sugarcane smut resistance having the nucleotide sequence as shown in SEQ ID NO: 1 were identified independently of each other; however, these regions comprise a plurality of markers having the identical nucleotide sequence.

[Use of Markers Associated with Sugarcane Smut Resistance]

With the use of markers associated with sugarcane smut resistance, whether or not a sugarcane progeny line or the like whose phenotype concerning smut resistance remains unknown would exhibit a phenotype for improved smut resistance can be determined. As the marker associated with sugarcane smut resistance, one or more nucleic acid regions included in the 8.4 cM region mentioned above may be used. Alternatively, one or more nucleic acid regions included in the 26.6 cM region mentioned above may be used as the markers associated with sugarcane smut resistance. Further, one or more nucleic acid regions included in the 12.27 cM region may be used as the markers associated with sugarcane smut resistance. Furthermore, one or more nucleic acid regions included in the 8.4 cM region, one or more nucleic acid regions included in the 26.6 cM region, or one or more nucleic acid regions included in the 12.27 cM region may be used as the markers associated with sugarcane smut resistance. In this case, the use of the markers associated with sugarcane smut resistance encompasses an embodiment involving a nucleic acid amplification reaction with the use of a pair of primers that specifically amplifies the markers and an embodiment involving the use of a DNA microarray having probes corresponding to the markers.

A pair of primers that specifically amplifies the markers associated with sugarcane smut resistance can be adequately designed in accordance with the nucleotide sequence of the 8.4 cM region, the nucleotide sequence of the 26.6 cM region, and the nucleotide sequence of the 12.27 cM region. For example, a pair of primers can be designed to amplify a region included in the nucleotide sequence of the 8.4 cM region, the nucleotide sequence of the 26.6 cM region, and the nucleotide sequence of the 12.27 cM region, such as a region of 1 kbp or smaller, 800 bp or smaller, 500 bp or smaller, or 350 bp or smaller. Alternatively, a pair of primers can be designed to amplify a part of or the entire nucleic acid region comprising the nucleotide sequence as shown in any of SEQ ID NO: 1 to 6, 135 to 143, and 144 (145) to 151. A part of the nucleic acid region can be composed of 10 continuous bases, 20 continuous bases, 40 continuous bases, 80 continuous bases, 100 continuous bases, or 140 continuous bases included in the nucleotide sequence as shown in any of SEQ ID NO: 1 to 6, 135 to 143, and 144 (145) to 151.

A probe corresponding to the marker associated with sugarcane smut resistance is an oligonucleotide that can specifically hybridize under stringent conditions to the marker associated with sugarcane smut resistance as defined above. For example, such oligonucleotide can be designed as a partial region of at least 10 continuous bases, 15 continuous bases, 20 continuous bases, 25 continuous bases, 30 continuous bases, 35 continuous bases, 40 continuous bases, 45 continuous bases, or 50 continuous bases of the entire region of the nucleotide sequence of the marker associated with sugarcane smut resistance as defined above or a complementary strand thereof. The probe can be immobilized on a support. Specifically, any type of microarray, such as a microarray having a planar substrate made of glass or silicone as a carrier, a bead array comprising microbeads as carriers, or a three-dimensional microarray comprising a probe immobilized on an inner wall of a hollow fiber, can be used.

With the use of the DNA microarray thus prepared, whether or not a sugarcane line whose phenotype concerning smut resistance remains unknown as typified by a progeny line or the like would exhibit a phenotype for improved smut resistance can be determined. By any method other than the method involving the use of a DNA microarray as described above, whether or not a sugarcane line whose phenotype concerning smut resistance remains unknown would exhibit a phenotype for improved smut resistance may be determined by detecting the marker associated with sugarcane smut resistance in accordance with a conventional technique.

More specifically, genomic DNA is first extracted from a sugarcane sample. In this case, a sugarcane sample is a sugarcane line such as a sugarcane progeny line whose phenotype concerning smut resistance remains unknown and/or a parent sugarcane line used for producing a progeny line. Such sugarcane lines are to be evaluated as to have a trait for improved smut resistance. Also, plants other than sugarcane, such as graminaceous plants including *Sorghum* or *Erianthus*, may be employed as plant samples and smut resistance of such plant samples may be evaluated.

Subsequently, a nucleic acid amplification reaction is carried out with the use of the extracted genomic DNA as a template and the pair of primers described above, so as to amplify the marker associated with sugarcane smut resistance. In this case, one of the primers may be labeled with a fluorescent dye and so on, so that the amplified genomic DNA fragment can be labeled. Any conventional substance may be used as a label. Examples of labels that can be used include fluorescent molecules, dye molecules, radioactive molecules, and so on.

Subsequently, a labeled genomic DNA fragment is brought into contact with the DNA microarray under given conditions, so as to allow a probe immobilized on the DNA microarray to hybridize to the labeled genomic DNA fragment. In such a case, hybridization is preferably carried out under highly stringent conditions. Thus, whether or not a sugarcane sample has the marker associated with sugarcane smut resistance can be determined with higher accuracy. In addition, stringent conditions can be adjusted in terms of reaction temperature and salt concentration. That is, higher stringency can be realized by raising temperature or lowering salt concentration. When a probe of 50- to 75-base length is used, for example, higher stringency can be realized by performing hybridization at 40 degrees C. to 44 degrees C. in 0.21 SDS and 6×SSC.

In addition, hybridization between a probe and a labeled genomic DNA fragment can be confirmed by detecting a label. After the above hybridization reaction between the labeled genomic DNA fragment and the probe, specifically, an unreacted genomic DNA fragment or the like is washed, and the label bound to the genomic DNA fragment specifically hybridized to the probe is then observed. When the label is a fluorescent material, for example, the fluorescence wavelength is detected. When the label is a dye molecule, the dye wavelength is detected. More specifically, an apparatus, such as a fluorescent detector or an image analyzer used for conventional DNA microarray analysis, can be used.

It is also possible to detect the marker associated with sugarcane smut resistance in the genomic DNA extracted from a sugarcane sample by a method other than the method involving the use of DNA microarrays described above. For example, the genomic DNA extracted from a sugarcane sample is used as a template and the read number of the marker associated with sugarcane smut resistance is measured using a next-generation sequencer. Thus, the presence or absence of the marker associated with sugarcane smut resistance can be determined with high accuracy.

With the use of the DNA microarray or next-generation sequencer, as described above, whether or not the sugarcane sample has the marker associated with sugarcane smut resistance can be determined. The marker associated with sugarcane smut resistance is linked to a trait of improving smut resistance. If the marker associated with sugarcane smut resistance is present in a sugarcane sample, accordingly, the sugarcane sample can be identified as a variety with improved smut resistance.

According to the method described above, in particular, it is not necessary to cultivate sugarcane samples to such an extent that an actual smut resistance test can be performed. For instance, seeds of a progeny line or a young seedling obtained as a result of germination of such seeds can be used. Therefore, the area of a field used for cultivation of sugarcane samples and other factors such as cost of cultivation can be significantly reduced with the use of the markers associated with sugarcane smut resistance. In addition, use of markers associated with sugarcane smut resistance eliminates the need of actual infection with a causative microorganism of smut (*Ustilago scitaminea*), and the cost of facilities such as a large-scale special-purpose greenhouse, a special-purpose field, or a facility isolated from an external environment, can be reduced.

When producing a novel sugarcane variety, it is particularly preferable that several tens of thousands of hybrids be first produced via crossbreeding and evaluated with the use of markers associated with sugarcane smut resistance prior to or instead of seedling selection. Thus, the number of elite lines to be cultivated in actual fields can be reduced to a significant extent, and time-consuming efforts and the cost required for production of a novel sugarcane variety can be reduced to a significant extent.

When producing a novel sugarcane variety, alternatively, whether or not a marker associated with sugarcane smut resistance is present in a parent variety subjected to crossbreeding may be first determined, so as to select a parent variety with excellent smut resistance. A parent variety with excellent smut resistance may be preferentially used to produce a progeny line, so that development of a progeny line with excellent smut resistance with high frequency can be expected. Thus, the number of elite lines to be cultivated can be reduced to a significant extent, and time-consuming efforts and the cost required for production of a novel sugarcane variety can be reduced to a significant extent.

EXAMPLES

The present invention is hereafter described in greater detail with reference to the following examples, although the technical scope of the present invention is not limited thereto.

Example 1

(1) Materials

Genomic DNAs were extracted from the sugarcane variety (NiF8), the wild-type sugarcane variety (Iriomote 15), 3 progeny lines (KY08-6023), (KY08-6039), and (KY08-6041) resulting from crossbreeding between (NiF8) and (Iriomote 15), and 33, 35, and 35 progeny lines resulting from crossbreeding between (KY08-6023) and the wild-type sugarcane variety (JW90), between (KY08-6039) and the wild-type sugarcane variety (JW90), and between (KY08-6041) and the wild-type sugarcane variety (JW90), respectively. The extracted genomic DNAs were purified with the use of the DNeasy Plant Mini Kit (QIAGEN).

(2) Preparation of DNA Library

In this example, a DNA library was prepared in accordance with the method for preparing a DNA library described in WO 2018/003220. Specifically, a dNTP mixture (final concentration 0.2 mM) was added to 15.0 ng of the genomic DNA obtained in (1) above, a 60 microM random primer was added to 0.625 units of Prime STAR DNA Polymerase (Takara Bio Inc.), and the resulting mixtures were each subjected to PCR in the final reaction amount of 25 microliters. PCR was carried out through treatment at 98 degrees C. for 2 minutes, and 30 cycles of 98 degrees C. for 10 seconds, 50 degrees C. for 15 seconds, and 72 degrees C. for 20 seconds, followed by storage at 4 degrees C.

The random primers used in this example are summarized in Table 4.

TABLE 4

| No | Sequence (5'→3') | SEQ ID NO: |
|---|---|---|
| 1 | TAAGAGACAGAGA | 7 |
| 2 | TAAGAGACAGAGC | 8 |
| 3 | TAAGAGACAGCGT | 9 |
| 4 | TAAGAGACAGCTA | 10 |
| 5 | TAAGAGACAGCTC | 11 |
| 6 | TAAGAGACAGGCT | 12 |
| 7 | TAAGAGACAGGTA | 13 |
| 8 | TAAGAGACAGGTC | 14 |
| 9 | TAAGAGACAGTAC | 15 |
| 10 | TAAGAGACAGTCA | 18 |

TABLE 4-continued

| No | Sequence (5'→3') | SEQ ID NO: |
|---|---|---|
| 11 | TAAGAGACAGTGA | 17 |
| 12 | TAAGAGACAGTTG | 18 |

(3) Preparation of DNA Library for Next-Generation Sequencer

A dNTP mixture (final concentration 0.2 mM), 1.25 units of PrimeSTAR HS DNA Polymerase (Takara Bio Inc.), and a set of primers were added to 1.5 microliters of the solution after the reaction of (2) and the resulting mixtures were each subjected to PCR in the final reaction amount of 50 microliters. PCR was carried out through treatment at 95 degrees C. for 2 minutes, and 25 cycles of 98 degrees C. for 15 seconds, 55 degrees C. for 15 seconds, and 72 degrees C. for 20 seconds, followed by storage at 4 degrees C. In this example, the forward primers (SEQ ID NOs: 19 to 133) shown in Table 5 and the reverse primer (5'-AATGA-TACGGCGACCACCGAGATCTACACCGCGCA-GATCGTCGGCAGCGTCAGATGTGTATAAGAGACAG-3' (SEQ ID NO: 134)) were used in combination for a total of 115 combinations of 103 lines resulting from crossbreeding between (KY08-6023), (KY08-6039), or (KY08-6041) and (JW90) (33, 35, and 35 lines, respectively) and 6 lines of the parent and grandparent lines (i.e., (NiF8), (Iriomote 15), (KY08-6023), (KY08-6039), (KY08-6041), and (JW90)) (2 repeats each).

TABLE 5

| No | Forward (5' → 3') | SEQ ID NO: |
|---|---|---|
| 1 | CAAGCAGAAGACGGCATACGAGATTCGTCAGAGTCTCGTGGGCTCGGAGATGTGTATAAGAGACAG | 19 |
| 2 | CAAGCAGAAGACGGCATACGAGATCGCTAGCGGTCTCGTGGGCTCGGAGATGTGTATAAGAGACAG | 20 |
| 3 | CAAGCAGAAGACGGCATACGAGATTCTCAGTAGTCTCGTGGGCTCGGAGATGTGTATAAGAGACAG | 21 |
| 4 | CAAGCAGAAGACGGCATACGAGATCGTAGATAGTCTCGTGGGCTCGGAGATGTGTATAAGAGACAG | 22 |
| 5 | CAAGCAGAAGACGGCATACGAGATACGAGCAGGTCTCGTGGGCTCGGAGATGTGTATAAGAGACAG | 23 |
| 6 | CAAGCAGAAGACGGCATACGAGATATACGTGAGTCTCGTGGGCTCGGAGATGTGTATAAGAGACAG | 24 |
| 7 | CAAGCAGAAGACGGCATACGAGATGTCTAGAGGTCTCGTGGGCTCGGAGATGTGTATAAGAGACAG | 25 |
| 8 | CAAGCAGAAGACGGCATACGAGATAGTCGACAGTCTCGTGGGCTCGGAGATGTGTATAAGAGACAG | 26 |
| 9 | CAAGCAGAAGACGGCATACGAGATCTCACAGAGTCTCGTGGGCTCGGAGATGTGTATAAGAGACAG | 27 |
| 10 | CAAGCAGAAGACGGCATACGAGATAGACATAGGTCTCGTGGGCTCGGAGATGTGTATAAGAGACAG | 28 |
| 11 | CAAGCAGAAGACGGCATACGAGATAGCGACGCGTCTCGTGGGCTCGGAGATGTGTATAAGAGACAG | 29 |
| 12 | CAAGCAGAAGACGGCATACGAGATTGATAGAGGTCTCGTGGGCTCGGAGATGTGTATAAGAGACAG | 30 |
| 13 | CAAGCAGAAGACGGCATACGAGATGACGACTGGTCTCGTGGGCTCGGAGATGTGTATAAGAGACAG | 31 |
| 14 | CAAGCAGAAGACGGCATACGAGATTGTGCTCAGTCTCGTGGGCTCGGAGATGTGTATAAGAGACAG | 32 |
| 15 | CAAGCAGAAGACGGCATACGAGATATGAGCTGGTCTCGTGGGCTCGGAGATGTGTATAAGAGACAG | 33 |
| 16 | CAAGCAGAAGACGGCATACGAGATTCTCTCACGTCTCGTGGGCTCGGAGATGTGTATAAGAGACAG | 34 |
| 17 | CAAGCAGAAGACGGCATACGAGATGCAGATCAGTCTCGTGGGCTCGGAGATGTGTATAAGAGACAG | 35 |
| 18 | CAAGCAGAAGACGGCATACGAGATTCTGCAGAGTCTCGTGGGCTCGGAGATGTGTATAAGAGACAG | 36 |
| 19 | CAAGCAGAAGACGGCATACGAGATACGTGAGCGTCTCGTGGGCTCGGAGATGTGTATAAGAGACAG | 37 |
| 20 | CAAGCAGAAGACGGCATACGAGATCGCGTGAGGTCTCGTGGGCTCGGAGATGTGTATAAGAGACAG | 38 |

TABLE 5-continued

| No | Forward (5' → 3') | SEQ ID NO: |
|---|---|---|
| 21 | CAAGCAGAAGACGGCATACGAGATCATACTACGTCTCGTGGGCTCGGAGATGTGTATAAGAGACAG | 39 |
| 22 | CAAGCAGAAGACGGCATACGAGATTCTACACAGTCTCGTGGGCTCGGAGATGTGTATAAGAGACAG | 40 |
| 23 | CAAGCAGAAGACGGCATACGAGATGATAGATCGTCTCGTGGGCTCGGAGATGTGTATAAGAGACAG | 41 |
| 24 | CAAGCAGAAGACGGCATACGAGATGAGCGTACGTCTCGTGGGCTCGGAGATGTGTATAAGAGACAG | 42 |
| 25 | CAAGCAGAAGACGGCATACGAGATCAGAGACAGTCTCGTGGGCTCGGAGATGTGTATAAGAGACAG | 43 |
| 26 | CAAGCAGAAGACGGCATACGAGATCATAGATGGTCTCGTGGGCTCGGAGATGTGTATAAGAGACAG | 44 |
| 27 | CAAGCAGAAGACGGCATACGAGATAGATGCTAGTCTCGTGGGCTCGGAGATGTGTATAAGAGACAG | 45 |
| 28 | CAAGCAGAAGACGGCATACGAGATCTCATCTCGTCTCGTGGGCTCGGAGATGTGTATAAGAGACAG | 46 |
| 29 | CAAGCAGAAGACGGCATACGAGATTATCTATGGTCTCGTGGGCTCGGAGATGTGTATAAGAGACAG | 47 |
| 30 | CAAGCAGAAGACGGCATACGAGATAGAGTATCGTCTCGTGGGCTCGGAGATGTGTATAAGAGACAG | 48 |
| 31 | CAAGCAGAAGACGGCATACGAGATGTGACTAGGTCTCGTGGGCTCGGAGATGTGTATAAGAGACAG | 49 |
| 32 | CAAGCAGAAGACGGCATACGAGATCTATGCTCGTCTCGTGGGCTCGGAGATGTGTATAAGAGACAG | 50 |
| 33 | CAAGCAGAAGACGGCATACGAGATCTGACTACGTCTCGTGGGCTCGGAGATGTGTATAAGAGACAG | 51 |
| 34 | CAAGCAGAAGACGGCATACGAGATTATCAGTAGTCTCGTGGGCTCGGAGATGTGTATAAGAGACAG | 52 |
| 35 | CAAGCAGAAGACGGCATACGAGATGAGTCTGCGTCTCGTGGGCTCGGAGATGTGTATAAGAGACAG | 53 |
| 36 | CAAGCAGAAGACGGCATACGAGATCAGTCGCAGTCTCGTGGGCTCGGAGATGTGTATAAGAGACAG | 54 |
| 37 | CAAGCAGAAGACGGCATACGAGATGACATCTAGTCTCGTGGGCTCGGAGATGTGTATAAGAGACAG | 55 |
| 38 | CAAGCAGAAGACGGCATACGAGATCTGTGACGGTCTCGTGGGCTCGGAGATGTGTATAAGAGACAG | 56 |
| 39 | CAAGCAGAAGACGGCATACGAGATAAGAGGCAGTCTCGTGGGCTCGGAGATGTGTATAAGAGACAG | 57 |
| 40 | CAAGCAGAAGACGGCATACGAGATCTAGTACGGTCTCGTGGGCTCGGAGATGTGTATAAGAGACAG | 58 |
| 41 | CAAGCAGAAGACGGCATACGAGATAGGAGTCCGTCTCGTGGGCTCGGAGATGTGTATAAGAGACAG | 59 |
| 42 | CAAGCAGAAGACGGCATACGAGATCATGCCTAGTCTCGTGGGCTCGGAGATGTGTATAAGAGACAG | 60 |
| 43 | CAAGCAGAAGACGGCATACGAGATGTAGAGAGGTCTCGTGGGCTCGGAGATGTGTATAAGAGACAG | 61 |
| 44 | CAAGCAGAAGACGGCATACGAGATCCTCTCTGGTCTCGTGGGCTCGGAGATGTGTATAAGAGACAG | 62 |
| 45 | CAAGCAGAAGACGGCATACGAGATAGCGTAGCGTCTCGTGGGCTCGGAGATGTGTATAAGAGACAG | 63 |
| 46 | CAAGCAGAAGACGGCATACGAGATTCCTCTACGTCTCGTGGGCTCGGAGATGTGTATAAGAGACAG | 64 |
| 47 | CAAGCAGAAGACGGCATACGAGATGACGTACAGTCTCGTGGGCTCGGAGATGTGTATAAGAGACAG | 65 |
| 48 | CAAGCAGAAGACGGCATACGAGATGACTGTAGGTCTCGTGGGCTCGGAGATGTGTATAAGAGACAG | 66 |
| 49 | CAAGCAGAAGACGGCATACGAGATTCAGTACAGTCTCGTGGGCTCGGAGATGTGTATAAGAGACAG | 67 |
| 50 | CAAGCAGAAGACGGCATACGAGATCATGATAGGTCTCGTGGGCTCGGAGATGTGTATAAGAGACAG | 68 |
| 51 | CAAGCAGAAGACGGCATACGAGATGCATCTCGGTCTCGTGGGCTCGGAGATGTGTATAAGAGACAG | 69 |
| 52 | CAAGCAGAAGACGGCATACGAGATTGCACAGAGTCTCGTGGGCTCGGAGATGTGTATAAGAGACAG | 70 |
| 53 | CAAGCAGAAGACGGCATACGAGATGAGCTATAGTCTCGTGGGCTCGGAGATGTGTATAAGAGACAG | 71 |
| 54 | CAAGCAGAAGACGGCATACGAGATAGTCTGCAGTCTCGTGGGCTCGGAGATGTGTATAAGAGACAG | 72 |
| 55 | CAAGCAGAAGACGGCATACGAGATCGCTGTGAGTCTCGTGGGCTCGGAGATGTGTATAAGAGACAG | 73 |
| 56 | CAAGCAGAAGACGGCATACGAGATCTGATGTGGTCTCGTGGGCTCGGAGATGTGTATAAGAGACAG | 74 |
| 57 | CAAGCAGAAGACGGCATACGAGATGCACTCTAGTCTCGTGGGCTCGGAGATGTGTATAAGAGACAG | 75 |
| 58 | CAAGCAGAAGACGGCATACGAGATTCTGCTCAGTCTCGTGGGCTCGGAGATGTGTATAAGAGACAG | 76 |

TABLE 5-continued

| No | Forward (5' → 3') | SEQ ID NO: |
|---|---|---|
| 59 | CAAGCAGAAGACGGCATACGAGATTGTATCTAGTCTCGTGGGCTCGGAGATGTGTATAAGAGACAG | 77 |
| 60 | CAAGCAGAAGACGGCATACGAGATACAGTGAGGTCTCGTGGGCTCGGAGATGTGTATAAGAGACAG | 78 |
| 61 | CAAGCAGAAGACGGCATACGAGATATGCGATAGTCTCGTGGGCTCGGAGATGTGTATAAGAGACAG | 79 |
| 62 | CAAGCAGAAGACGGCATACGAGATGAGACATGGTCTCGTGGGCTCGGAGATGTGTATAAGAGACAG | 80 |
| 63 | CAAGCAGAAGACGGCATACGAGATGTCATGTGGTCTCGTGGGCTCGGAGATGTGTATAAGAGACAG | 81 |
| 64 | CAAGCAGAAGACGGCATACGAGATTCATGATAGTCTCGTGGGCTCGGAGATGTGTATAAGAGACAG | 82 |
| 65 | CAAGCAGAAGACGGCATACGAGATGTCATCTCGTCTCGTGGGCTCGGAGATGTGTATAAGAGACAG | 83 |
| 66 | CAAGCAGAAGACGGCATACGAGATTATCTCTAGTCTCGTGGGCTCGGAGATGTGTATAAGAGACAG | 84 |
| 67 | CAAGCAGAAGACGGCATACGAGATCTGATATAGTCTCGTGGGCTCGGAGATGTGTATAAGAGACAG | 85 |
| 68 | CAAGCAGAAGACGGCATACGAGATTACGCATGGTCTCGTGGGCTCGGAGATGTGTATAAGAGACAG | 86 |
| 69 | CAAGCAGAAGACGGCATACGAGATCGTGAGTGGTCTCGTGGGCTCGGAGATGTGTATAAGAGACAG | 87 |
| 70 | CAAGCAGAAGACGGCATACGAGATGACACATGGTCTCGTGGGCTCGGAGATGTGTATAAGAGACAG | 88 |
| 71 | CAAGCAGAAGACGGCATACGAGATACATGACGGTCTCGTGGGCTCGGAGATGTGTATAAGAGACAG | 89 |
| 72 | CAAGCAGAAGACGGCATACGAGATGCGTCTAGGTCTCGTGGGCTCGGAGATGTGTATAAGAGACAG | 90 |
| 73 | CAAGCAGAAGACGGCATACGAGATTCACGCTGGTCTCGTGGGCTCGGAGATGTGTATAAGAGACAG | 91 |
| 74 | CAAGCAGAAGACGGCATACGAGATTCATGTACGTCTCGTGGGCTCGGAGATGTGTATAAGAGACAG | 92 |
| 75 | CAAGCAGAAGACGGCATACGAGATTAGTGACGGTCTCGTGGGCTCGGAGATGTGTATAAGAGACAG | 93 |
| 76 | CAAGCAGAAGACGGCATACGAGATCACGATAGGTCTCGTGGGCTCGGAGATGTGTATAAGAGACAG | 94 |
| 77 | CAAGCAGAAGACGGCATACGAGATACACACTGGTCTCGTGGGCTCGGAGATGTGTATAAGAGACAG | 95 |
| 78 | CAAGCAGAAGACGGCATACGAGATAGCATCACGTCTCGTGGGCTCGGAGATGTGTATAAGAGACAG | 96 |
| 79 | CAAGCAGAAGACGGCATACGAGATTAGTCGTAGTCTCGTGGGCTCGGAGATGTGTATAAGAGACAG | 97 |
| 80 | CAAGCAGAAGACGGCATACGAGATGCATCGCGGTCTCGTGGGCTCGGAGATGTGTATAAGAGACAG | 98 |
| 81 | CAAGCAGAAGACGGCATACGAGATATCATGTCGTCTCGTGGGCTCGGAGATGTGTATAAGAGACAG | 99 |
| 82 | CAAGCAGAAGACGGCATACGAGATGTACTCTAGTCTCGTGGGCTCGGAGATGTGTATAAGAGACAG | 100 |
| 83 | CAAGCAGAAGACGGCATACGAGATAGTGCATAGTCTCGTGGGCTCGGAGATGTGTATAAGAGACAG | 101 |
| 84 | CAAGCAGAAGACGGCATACGAGATCGCATCAGGTCTCGTGGGCTCGGAGATGTGTATAAGAGACAG | 102 |
| 85 | CAAGCAGAAGACGGCATACGAGATCGCTATAGGTCTCGTGGGCTCGGAGATGTGTATAAGAGACAG | 103 |
| 86 | CAAGCAGAAGACGGCATACGAGATTAGCTCTAGTCTCGTGGGCTCGGAGATGTGTATAAGAGACAG | 104 |
| 87 | CAAGCAGAAGACGGCATACGAGATGTCGATAGGTCTCGTGGGCTCGGAGATGTGTATAAGAGACAG | 105 |
| 88 | CAAGCAGAAGACGGCATACGAGATAGCTCGTAGTCTCGTGGGCTCGGAGATGTGTATAAGAGACAG | 106 |
| 89 | CAAGCAGAAGACGGCATACGAGATACACAGTAGTCTCGTGGGCTCGGAGATGTGTATAAGAGACAG | 107 |
| 90 | CAAGCAGAAGACGGCATACGAGATCAGATGTAGTCTCGTGGGCTCGGAGATGTGTATAAGAGACAG | 108 |
| 91 | CAAGCAGAAGACGGCATACGAGATCTCTACAGGTCTCGTGGGCTCGGAGATGTGTATAAGAGACAG | 109 |
| 92 | CAAGCAGAAGACGGCATACGAGATGTCACTAGGTCTCGTGGGCTCGGAGATGTGTATAAGAGACAG | 110 |
| 93 | CAAGCAGAAGACGGCATACGAGATTGTACTAGGTCTCGTGGGCTCGGAGATGTGTATAAGAGACAG | 111 |
| 94 | CAAGCAGAAGACGGCATACGAGATACGCTATGGTCTCGTGGGCTCGGAGATGTGTATAAGAGACAG | 112 |
| 95 | CAAGCAGAAGACGGCATACGAGATATGTATAGGTCTCGTGGGCTCGGAGATGTGTATAAGAGACAG | 113 |
| 96 | CAAGCAGAAGACGGCATACGAGATTGTGACAGGTCTCGTGGGCTCGGAGATGTGTATAAGAGACAG | 114 |
| 97 | CAAGCAGAAGACGGCATACGAGATGACGTCAGGTCTCGTGGGCTCGGAGATGTGTATAAGAGACAG | 115 |

TABLE 5-continued

| No | Forward (5' → 3') | SEQ ID NO: |
|---|---|---|
| 98 | CAAGCAGAAGACGGCATACGAGATAGATCGAGGTCTCGTGGGCTCGGAGATGTGTATAAGAGACAG | 116 |
| 99 | CAAGCAGAAGACGGCATACGAGATATAGTAGAGTCTCGTGGGCTCGGAGATGTGTATAAGAGACAG | 117 |
| 100 | CAAGCAGAAGACGGCATACGAGATTATGACTAGTCTCGTGGGCTCGGAGATGTGTATAAGAGACAG | 118 |
| 101 | CAAGCAGAAGACGGCATACGAGATTAGAGATGGTCTCGTGGGCTCGGAGATGTGTATAAGAGACAG | 119 |
| 102 | CAAGCAGAAGACGGCATACGAGATAGCTGAGAGTCTCGTGGGCTCGGAGATGTGTATAAGAGACAG | 120 |
| 103 | CAAGCAGAAGACGGCATACGAGATACATCTGAGTCTCGTGGGCTCGGAGATGTGTATAAGAGACAG | 121 |
| 104 | CAAGCAGAAGACGGCATACGAGATGCGTGCTAGTCTCGTGGGCTCGGAGATGTGTATAAGAGACAG | 122 |
| 105 | CAAGCAGAAGACGGCATACGAGATACATGTAGGTCTCGTGGGCTCGGAGATGTGTATAAGAGACAG | 123 |
| 106 | CAAGCAGAAGACGGCATACGAGATATAGAGAGGTCTCGTGGGCTCGGAGATGTGTATAAGAGACAG | 124 |
| 107 | CAAGCAGAAGACGGCATACGAGATGTATCTAGGTCTCGTGGGCTCGGAGATGTGTATAAGAGACAG | 125 |
| 108 | CAAGCAGAAGACGGCATACGAGATATACTGTAGTCTCGTGGGCTCGGAGATGTGTATAAGAGACAG | 126 |
| 109 | CAAGCAGAAGACGGCATACGAGATGCACATAGGTCTCGTGGGCTCGGAGATGTGTATAAGAGACAG | 127 |
| 110 | CAAGCAGAAGACGGCATACGAGATATGATGAGGTCTCGTGGGCTCGGAGATGTGTATAAGAGACAG | 128 |
| 111 | CAAGCAGAAGACGGCATACGAGATAGTAGTAGGTCTCGTGGGCTCGGAGATGTGTATAAGAGACAG | 129 |
| 112 | CAAGCAGAAGACGGCATACGAGATTATGTCAGGTCTCGTGGGCTCGGAGATGTGTATAAGAGACAG | 130 |
| 113 | CAAGCAGAAGACGGCATACGAGATGTGTGTAGTCTCGTGGGCTCGGAGATGTGTATAAGAGACAG | 131 |
| 114 | CAAGCAGAAGACGGCATACGAGATTACGACAGGTCTCGTGGGCTCGGAGATGTGTATAAGAGACAG | 132 |
| 115 | CAAGCAGAAGACGGCATACGAGATATGTGATGGTCTCGTGGGCTCGGAGATGTGTATAAGAGACAG | 133 |

(4) Purification and Electrophoresis

Equivalent amounts of the solutions after the reaction in (3) above were mixed in a tube, 50 microliters were separated therefrom and purified using the MinElute PCR Purification Kit (QIAGEN), and the resultant was electrophoresed using the Agilent 2100 bioanalyzer (Agilent Technology) to obtain a fluorescence unit (FU).

(5) Analysis Using Next-Generation Sequencer

The DNA library obtained in (3) was analyzed using the Hiseq4000 Sequence System (Illumina) using paired-end 100 bp reads.

(6) Analysis of Read Data

The read data obtained in (5) above were analyzed using analytical software (GRAS-Di, Toyota Motor Corporation) to obtain the genotype data of 31,191 markers.

(7) Preparation of Genetic Map

On the basis of the genotype data obtained from JW90 in (6) above, genetic map data comprising 86 linkage groups were obtained with the use of the AntMap software for constructing genetic linkage maps (Iwata H, Ninomiya. S., 2006, AntMap: Constructing genetic linkage maps using an ant colony optimization algorithm. Breed Sci., 56: 371-377) by calculation using the Kosambi's genetic distance formula. The 86 linkage groups include genotype data of 4,503 markers of JW90.

(8) Acquisition of Smut Resistance Test Data

Stalks were collected from the 3 progeny lines resulting from crossbreeding between the sugarcane variety (NiF8) and the wild-type sugarcane variety (Iriomote 15); i.e., (KY08-6023), (KY08-6039), and (KY08-6041), and 33, 35, and 35 progeny lines resulting from crossbreeding between (KY08-6023), (KY08-6039), and (KY08-6041) and the wild-type sugarcane variety (JW90), and the collected stalks were subjected to germination stimulation at room temperature and high humidity for 2 to 3 days, followed by wound inoculation with smut spores. For wound inoculation, wounds were made on both sides of buds (6 wounds in total; approximately 4.0 mm in depth), and a spore suspension ($10^7$ to $10^8$ spores/ml) was then applied to the wounds using a brush. Seedlings subjected to wound inoculation were cultivated for 2 to 3 days at room temperature and high humidity and planted in nursery boxes (40 buds/box, 2 boxes/line). The planted seedlings were cultivated at high humidity in a greenhouse. The degree of the development of smut was investigated by counting, as the number of affected seedlings, the number of seedlings showing a symptom of smut, which is the outgrowth of a smut whip from the apex of a stalk. After the investigation of the number of the affected seedlings, the plant bodies of affected seedlings were harvested at the ground level and removed. The morbidity of smut was calculated as a percentage of the number of germinating stocks (excluding stocks killed by non-smut causes) accounted for by the number of affected stocks. FIG. 1(A) shows the results of calculation of the morbidity of smut of the progeny line resulting from crossbreeding between (KY08-6023) and (JW90), FIG. 1(B) shows the results of calculation of the morbidity of smut of the progeny line resulting from crossbreeding between (KY08-6039) and (JW90), and FIG. 1(C) shows the results of calculation of the morbidity of smut of the progeny line resulting from crossbreeding between (KY08-6041) and (JW90).

9) Quantitative Trait Loci (QTL) Analysis

Based on the genetic map data obtained from JW90 in (7) above and the smut resistance test data obtained in (8) above, QTL analysis was carried out by the composite interval mapping (CIM) method using the QTL Cartographer gene analysis software (statgen.ncsu.edu/qtlcart/cartographer.html). The LOD threshold was determined to be 2.5. As a result, the presence of QTL linked to sugarcane smut resistance was confirmed in a region of approximately 8.4 cM including the markers AMP0121265 to AMP0100370 in the 42nd linkage group of the wild-type sugarcane variety (JW90) (Table 6 and FIG. 2). When the value indicating the effect is negative, QTL is linked to a trait of improving smut resistance.

TABLE 6

| Varity | Linkage group | Position (cM) | Range (cM) | Adjacent marker | LOD value | Effects (%) |
|---|---|---|---|---|---|---|
| JW90 | 42 | 0.0 | 8.4 | AMP0121265-AMP0100370 | 24.5 | −47.2 |

Figure 2:
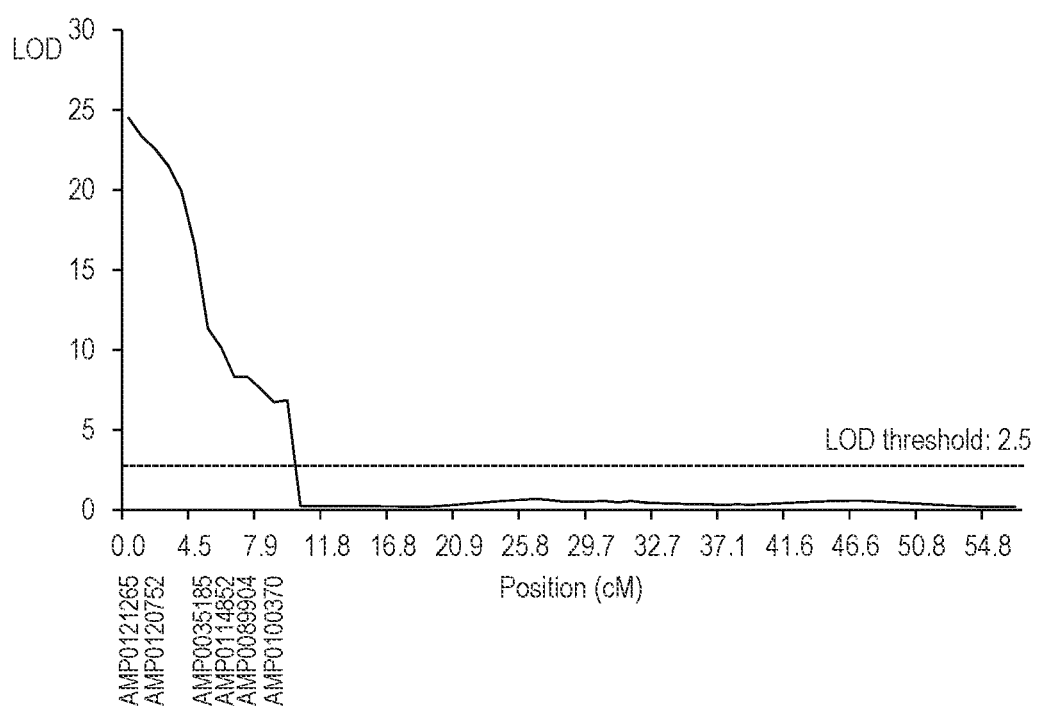
FIG. 2 shows a characteristic diagram showing the results of QTL analysis concerning smut resistance conducted in Example 1.
Figure 3:
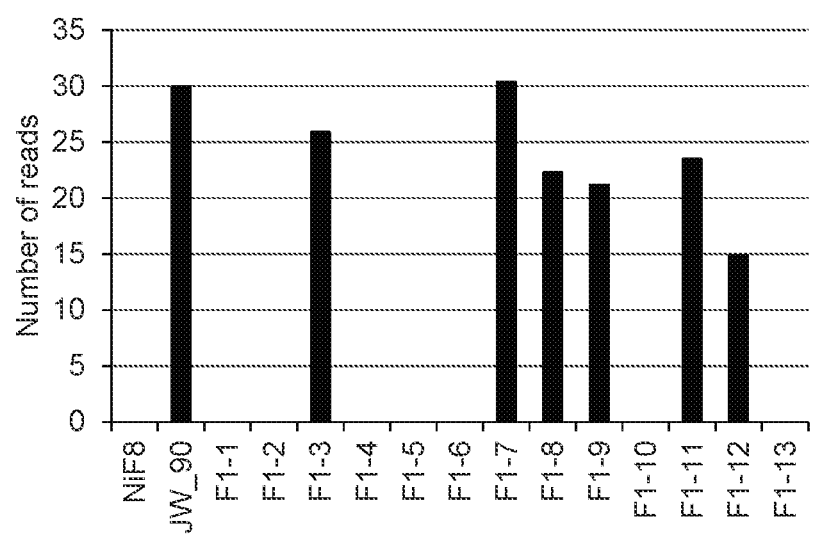
FIG. 3 shows a characteristic diagram showing the number of reads of AMP0121265 in each line.
Figure 4:
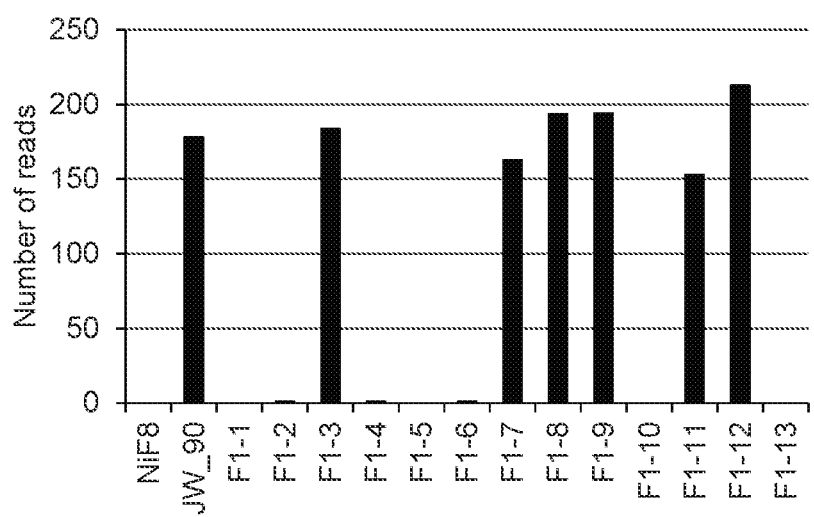
FIG. 4 shows a characteristic diagram showing the number of reads of AMP0120752 in each line.
Figure 5:
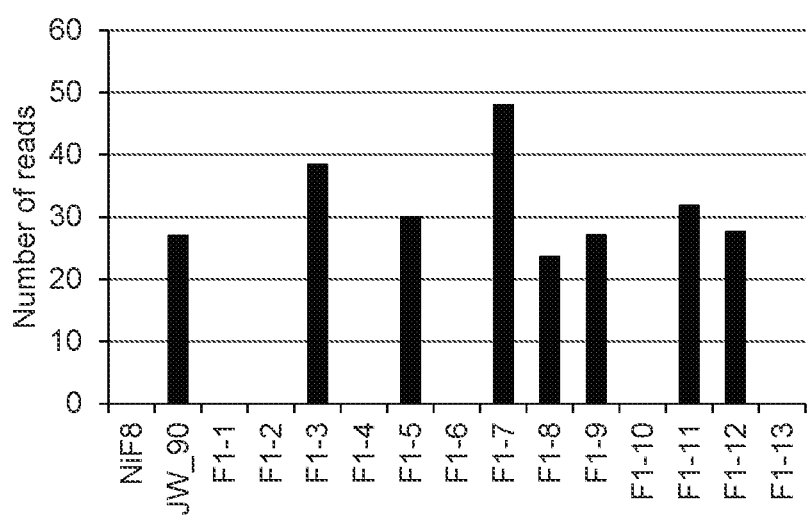
FIG. 5 shows a characteristic diagram showing the number of reads of AMP0035185 in each line.
Figure 6:
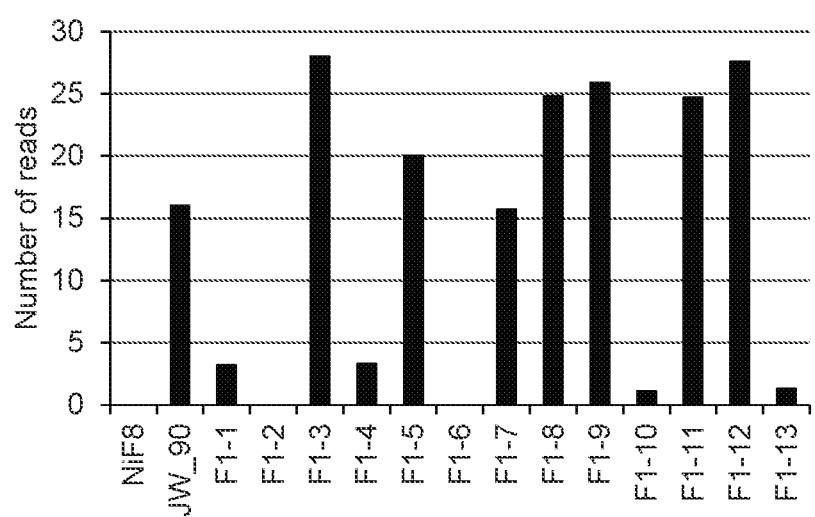
FIG. 6 shows a characteristic diagram showing the number of reads of AMP0114852 in each line.
Figure 7:
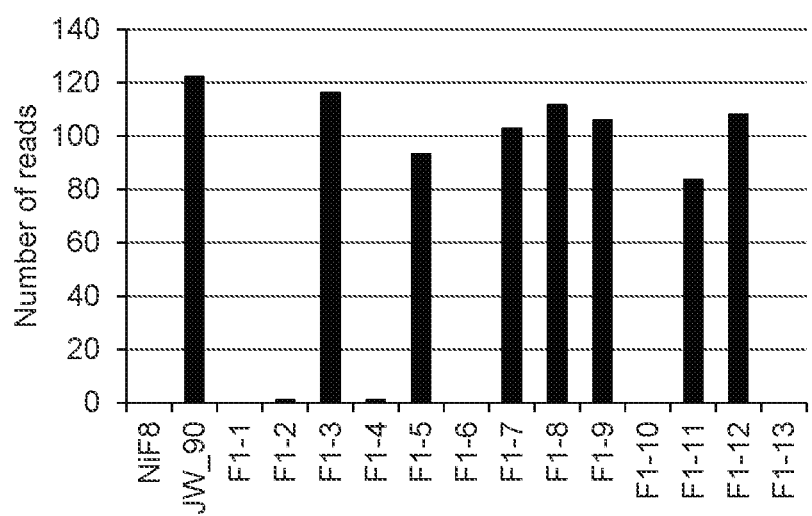
FIG. 7 shows a characteristic diagram showing the number of reads of AMP0089904 in each line.
Figure 8:
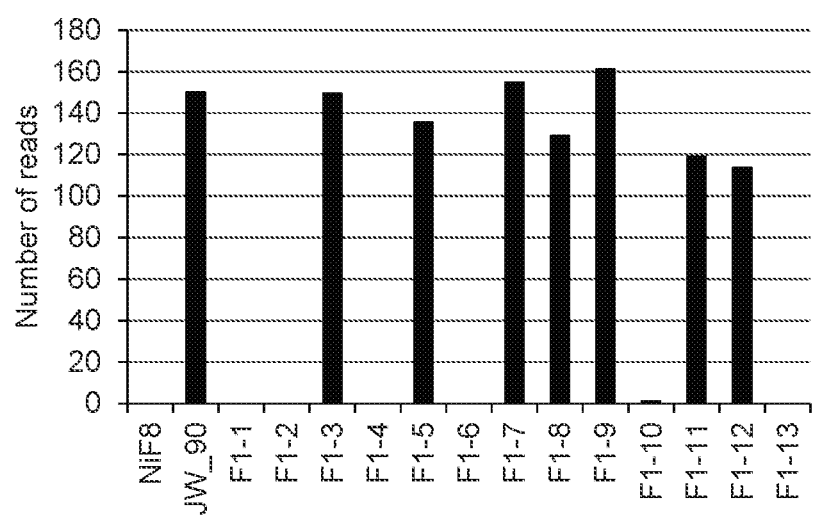
FIG. 8 shows a characteristic diagram showing the number of reads of AMP0100370 in each line.

As shown in Table 6 and FIG. 2, the range including the markers AMP0121265 to AMP0100370 in the 42nd linkage group observed in the present example exhibits a significantly higher LOD value and significantly improved effects, compared with those described in WO 2012/147635.

(10) Selection of Smut Resistance Selection Marker

The markers included in the QTL region linked to sugarcane smut resistance confirmed in (9) above (i.e., AMP0121265, AMP0120752, AMP0035185, AMP0114852, AMP0089904, and AMP0100370) were selected as selection markers (Table 7).

TABLE 7

| Varity | Linkage group | Marker | Nucleotide sequence information | SEQ ID NO: |
|---|---|---|---|---|
| JW90 | 42 | AMP0121265 | TAGCCCACTAAAAGAAAGCCTTGCATAACCC TTGATGTCACTTTATTTTGGTTTAAGACAGA TAAGTCTAGCTGAGTACCTTCTCGTACTTAG GGCGTTGTTCCCATTGTTGTTGTAGATGATT AGATGTACTACGGCTATTGCGTCA | SEQ ID NO: 1 |
| JW90 | 42 | AMP0120752 | TAGAGCGGAGGGCGTTGGAGCGTCTAGGAAT AGATCGCGTTCTCTCCAGTGGCGAGCCGATC TGAGTGGGAGGACGTGGATGGGGCTCACGCG GCGAGGAGGATGTGGATGCGGCGCCGTCCTG GTTCCTGCTCAACCACAGCGACGCTGGCGGC TACTGCACGGTGGA | SEQ ID NO: 2 |
| JW90 | 42 | AMP0035185 | CTCGAGCGGTGTCGGAGAGGAACAGGGGGAG CTGCCGGATGATGACCCGGTCGTCGGTGGCC CCACCCAGCTGACACGCCAAGCGGAAATCGG CGAGCCAAAGTTCGGGTTTGGTCTCGCTGTT GTACTTGGTGAGAGTCGTGGGGGGCGAAACC GCGCCGGGAGTATCATTTCACGAATAGCCTT ACTGAAGACCCGAGGGCCCGGAGGCTCGGGT GAAGGGCTACGATCCTCCGA | SEQ ID NO: 3 |
| JW90 | 42 | AMP0114852 | TACCCCACCAAAAAGCCTATCATGATCCTTG GTGTCATTTTATTTTGGTTCTGTCGGGTAAG TCTAGCTGAGTACCTTCTCGTACTCAGGGCT TTGTTCCCACTTGTTGCAGATGGACAGATGT AGTATGGTTATTGTATCA | SEQ ID NO: 4 |
| JW90 | 42 | AMP0089904 | GCCACCGGCCTCGTGGTCGTGAGACCGAGGA GAACGGTACCTGGGTATGGGCTGGTAGTCCT CATCCGTGCTGTCAGAAGTCACATCCTCAGG AAGATCAGCAGGCTGAGCGTCAAGATCGGCA AGCTCTGCCTCTGCAAGCTCATCAACTGTGG CGTCTTGCTCAGCTGCTGTCTCAGGAACCTC AGGTCGCTCAC | SEQ ID NO: 5 |

TABLE 7-continued

| Varity | Linkage group | Marker | Nucleotide sequence information | SEQ ID NO: |
|---|---|---|---|---|
| JW90 | 42 | AMP0100370 | GCGGTGAATAACGCGCAAAGGGTGAGAAGGC TCACACCGGATCTACGGGTTACACAGAGGTA CACATCCATCGATTCTAACACGGGCGTCCGG CTCGGCGCCGGGGCGCGGCGAGGGGTGGAGT GGATAGAACTCGCAGAAGAAGACGTGTTACT GTCTGTCCGCAC | SEQ ID NO: 6 |

Whether or not genotypes of the markers; i.e., the line samples, have the selection markers was determined by designating the threshold of each number of reads as 10, evaluating as "present" when the number of reads is 10 or more, and evaluating as "absent" when the number of reads is less than 10 (FIGS. 3 to 8, Table 8).

ant colony optimization algorithm, Breed Sci., 56: 371-377) by calculation using the Kosambi's genetic distance formula in the same manner as in Example 1. The 58 linkage groups include genotype data of 4,503 markers of the progeny lines; i.e., KY08-6023, KY08-6039, and KY08-6041, of Iriomote 15.

TABLE 8

| Marker | NiF8 | JW_90 | F1-1 | F1-2 | F1-3 | F1-4 | F1-5 | F1-6 | F1-7 | F1-8 | F1-9 | F1-10 | F1-11 | F1-12 | F1-13 |
|---|---|---|---|---|---|---|---|---|---|---|---|---|---|---|---|
| AMP0121265 | 0 | 30 | 0 | 0 | 25.9 | 0 | 0 | 0 | 30.4 | 22.3 | 21.2 | 0 | 23.5 | 14.9 | 0 |
| AMP0120752 | 0 | 178.2 | 0 | 1 | 183.6 | 1.1 | 0 | 1.1 | 162.6 | 193.5 | 194.1 | 0 | 153 | 212.6 | 0 |
| AMP0035185 | 0 | 27 | 0 | 0 | 38.4 | 0 | 30 | 0 | 48 | 23.6 | 27.1 | 0 | 31.8 | 27.6 | 0 |
| AMP0114852 | 0 | 16 | 3.2 | 0 | 28 | 3.3 | 20 | 0 | 15.7 | 24.8 | 25.9 | 1.1 | 24.7 | 27.6 | 1.3 |
| AMP0089904 | 0 | 122.1 | 0 | 1 | 116.2 | 1.1 | 93.3 | 0 | 102.9 | 111.6 | 105.9 | 0 | 83.6 | 108 | 0 |
| AMP0100370 | 0 | 150.2 | 0 | 0 | 149.4 | 0 | 135.5 | 0 | 154.8 | 129 | 161.1 | 1.1 | 118.9 | 113.8 | 0 |
| Incidence of smut (%) | 40.8 | 0 | 50.9 | 50 | 0 | 70.1 | 87.7 | 90.7 | 0 | 0 | 0 | 80.3 | 0 | 0 | 97.3 |

As shown in Table 8 and FIGS. 3 to 8, a line sample exhibiting a lower morbidity of smut has a significantly larger number of markers than a line sample exhibiting a higher morbidity of smut. Such results demonstrate that continuous nucleic acid regions selected from the region of approximately 8.4 cM including AMP0121265, AMP0120752, AMP0035185, AMP0114852, AMP0089904, and AMP0100370 can be used as the markers associated with sugarcane smut resistance.

Example 2

In Example 1, the marker associated with sugarcane smut resistance was identified based on the genotype data of 4,503 markers of JW90 among the genotype data of the 31,191 markers. In this example, the genotype data of Iriomote 15 were collected, and the marker associated with sugarcane smut resistance was identified in the same manner.

In this example, the DNA library prepared in Example 1 was subjected to the analysis using a next-generation sequencer as described in (5) two times in order to increase the amount of genotype data of Iriomote 15. The read data thus obtained were analyzed using analytical software (GRAS-Di, Toyota Motor Corporation) to obtain the genotype data of 64,757 markers.

On the basis of the genotype data obtained from progeny lines; i.e., KY08-6023, KY08-6039, and KY08-6041, of Iriomote 15, genetic map data comprising 58 linkage groups were obtained with the use of the AntMap software for constructing genetic linkage maps (Iwata H, Ninomiya, S., 2006, AntMap: Constructing genetic linkage maps using an Based on the genetic map data thus obtained and the smut resistance test data obtained in Example 1, QTL analysis was carried out by the composite interval mapping (CIM) method using the QTL Cartographer gene analysis software (statgen.ncsu.edu/qtlcart/cartographer.html). The LOD threshold was determined to be 2.5. As a result, the presence of QTL linked to sugarcane smut resistance was confirmed in a region between the markers AMP0014532 and AMP0015886 in the 15th linkage group of the wild-type sugarcane variety (Iriomote 15) (Table 9 and FIG. 9). When the value indicating the effect is negative, QTL is linked to a trait of improving the smut resistance.

TABLE 9

| Varity | Linkage group | Position (cM) | Range (cM) | Adjacent marker | LOD value | Effects (%) |
|---|---|---|---|---|---|---|
| Iriomote 15 | 15 | 25.7 | 26.6 | AMP0014532-AMP0015886 | 11.5 | −37.8 |

Figure 9:
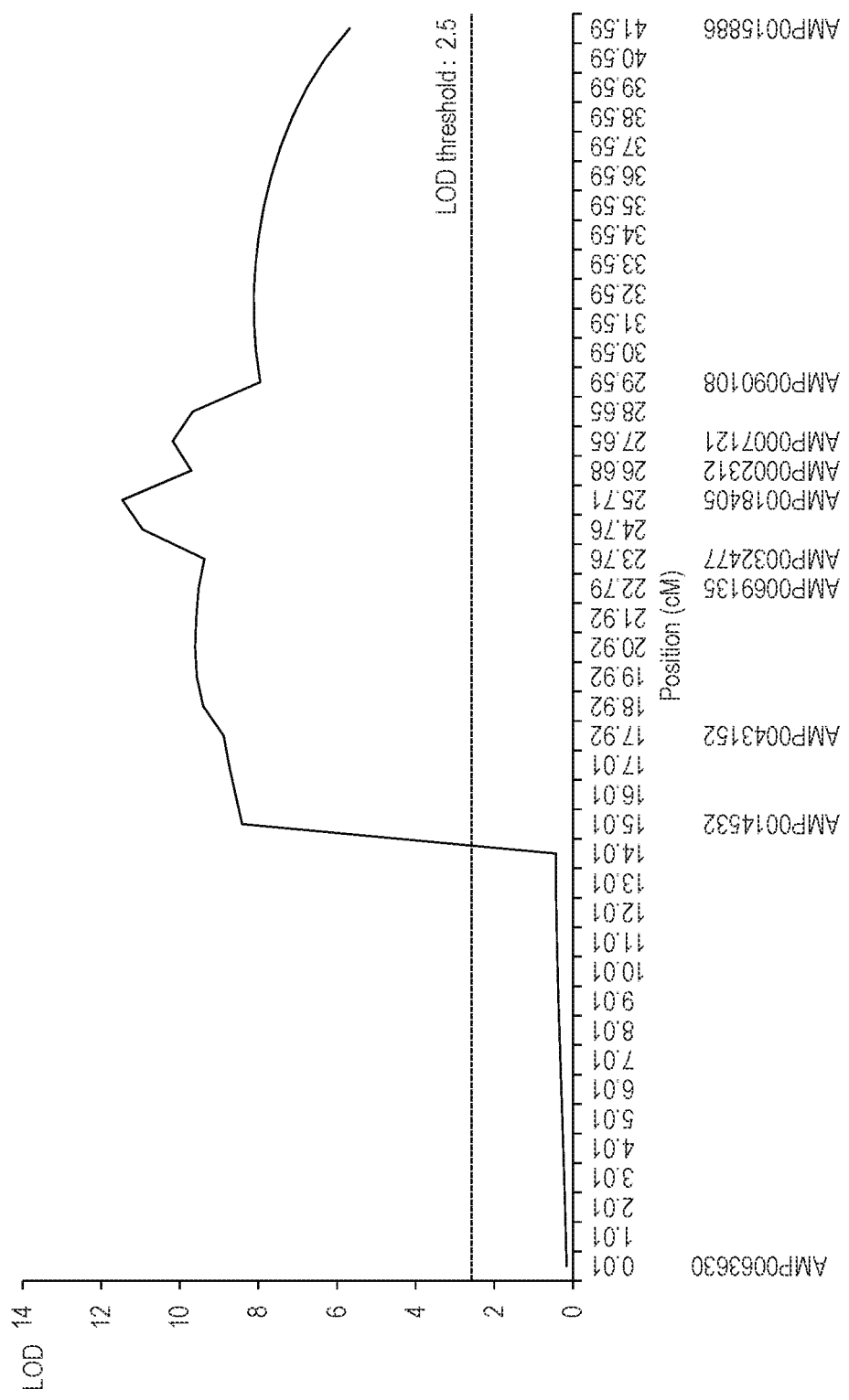
FIG. 9 shows a characteristic diagram showing the results of QTL analysis concerning smut resistance conducted in Example 2.
Figure 10:
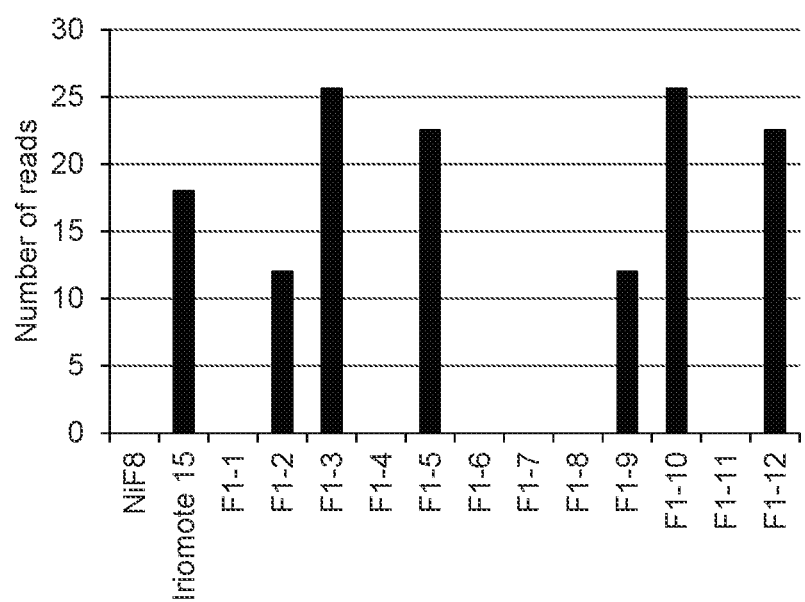
FIG. 10 shows a characteristic diagram showing the number of reads of AMP0014532 in each line.
Figure 11:
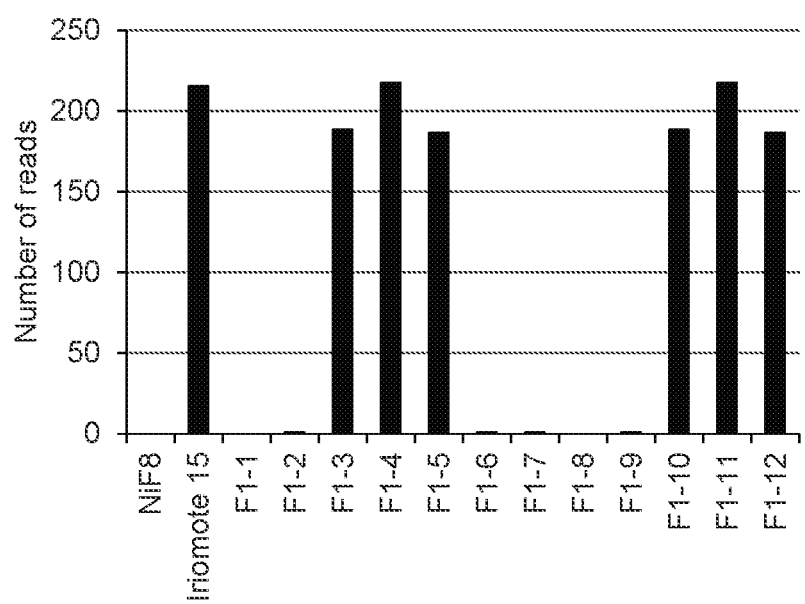
FIG. 11 shows a characteristic diagram showing the number of reads of AMP0043152 in each line.
Figure 12:
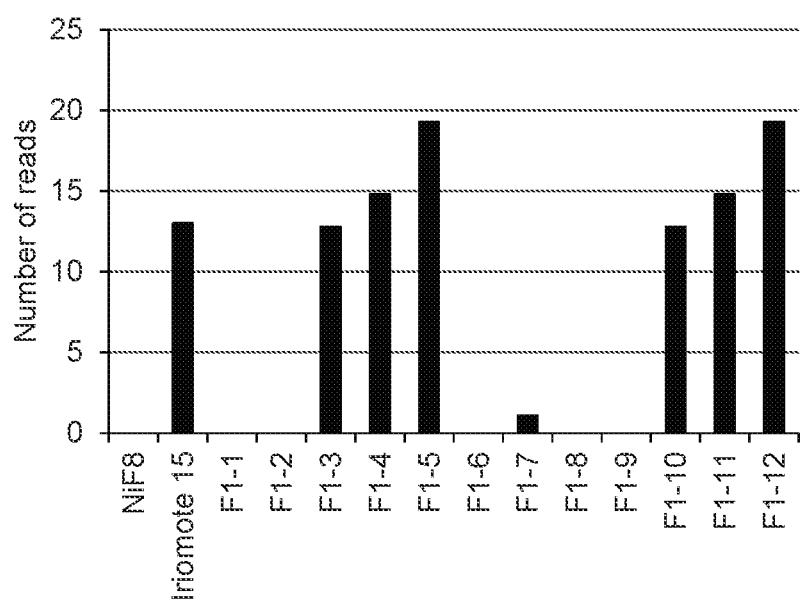
FIG. 12 shows a characteristic diagram showing the number of reads of AMP0069135 in each line.
Figure 13:
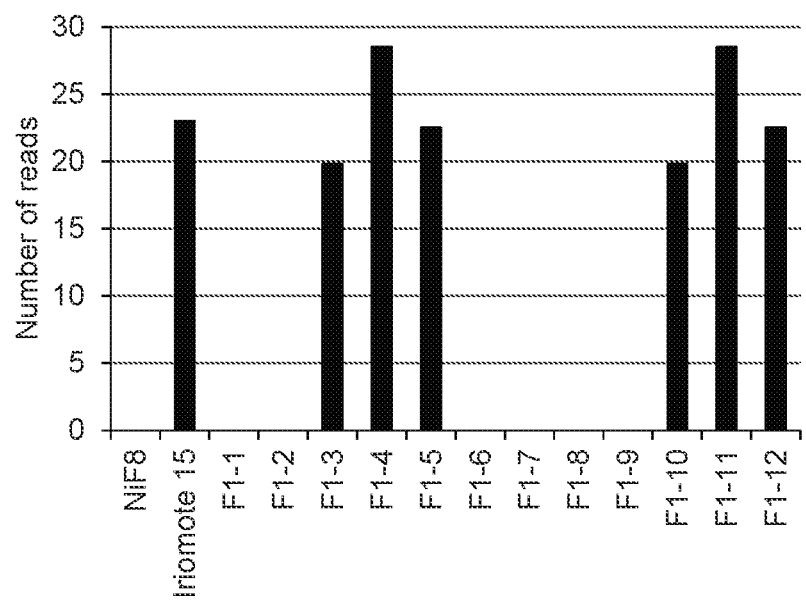
FIG. 13 shows a characteristic diagram showing the number of reads of AMP0032477 in each line.
Figure 14:
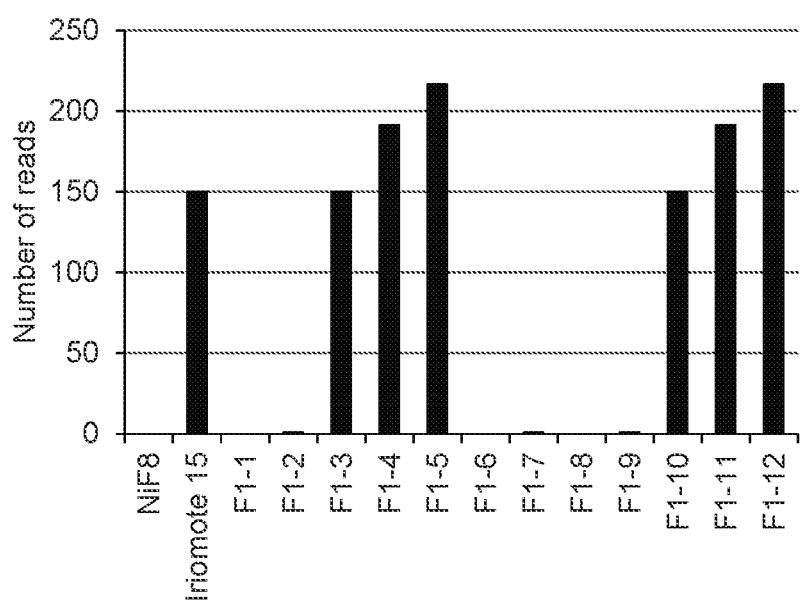
FIG. 14 shows a characteristic diagram showing the number of reads of AMP0018405 in each line.
Figure 15:
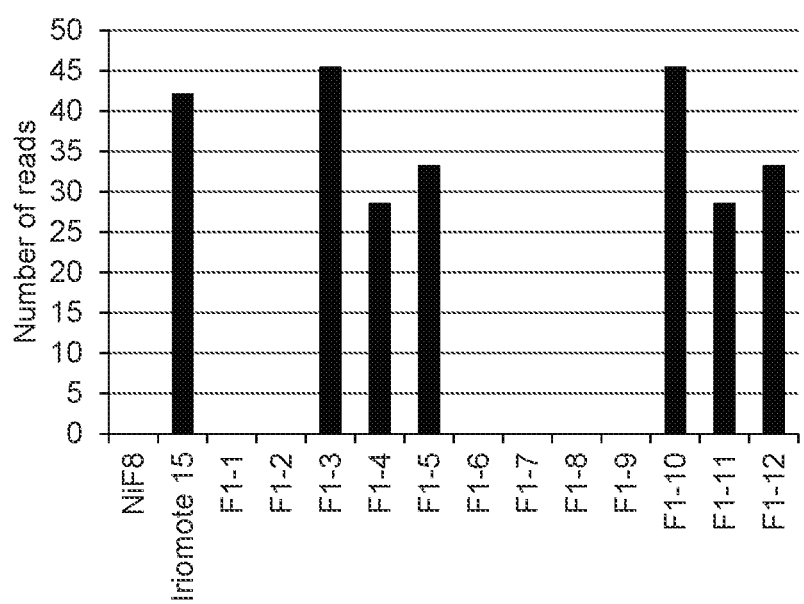
FIG. 15 shows a characteristic diagram showing the number of reads of AMP0002312 in each line.
Figure 16:
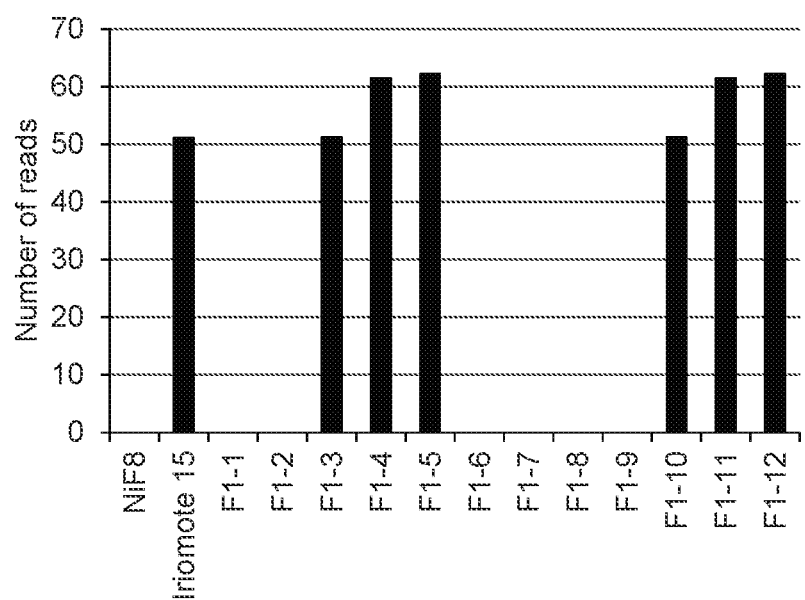
FIG. 16 shows a characteristic diagram showing the number of reads of AMP0007121 in each line.
Figure 17:
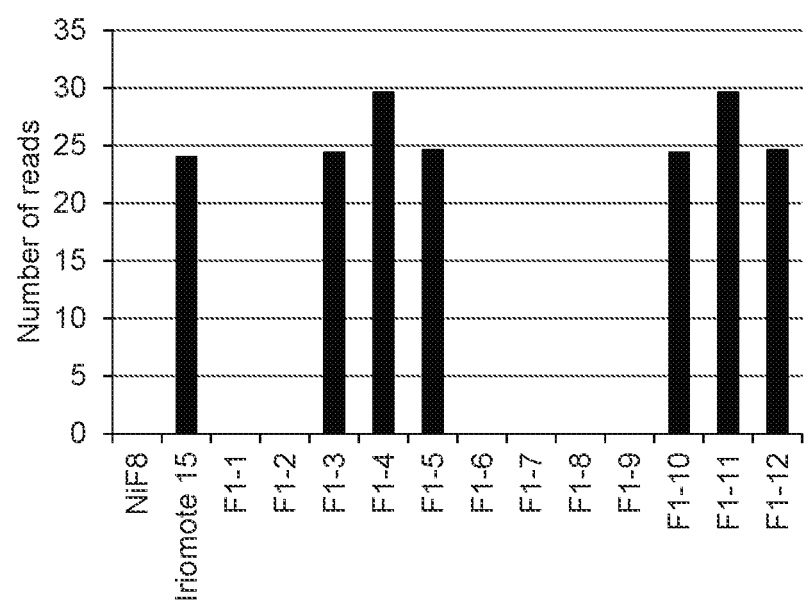
FIG. 17 shows a characteristic diagram showing the number of reads of AMP0090108 in each line.
Figure 18:
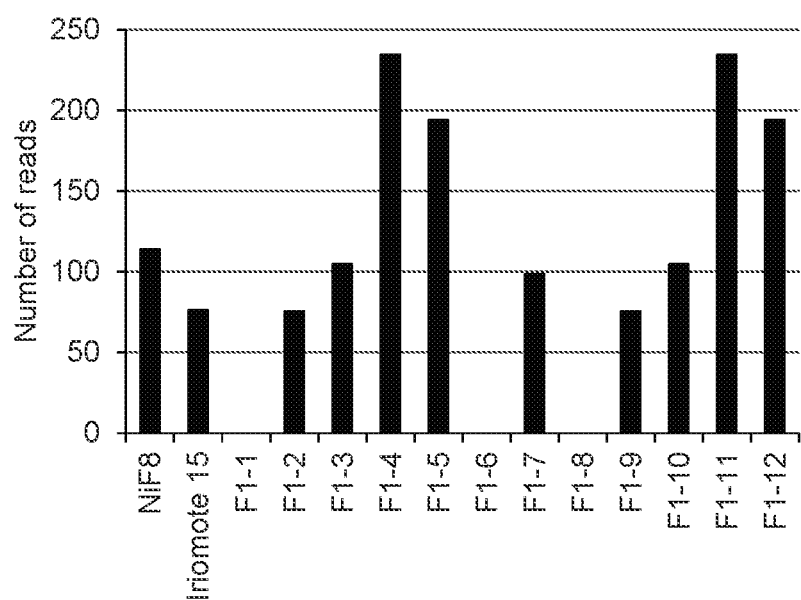
FIG. 18 shows a characteristic diagram showing the number of reads of AMP0015886 in each line.

As shown in Table 9 and FIG. 9, the range including the markers AMP0014532 to AMP0015886 in the 15th linkage group observed in Example 2 was found to exhibit a significantly higher LOD value and significantly improved effects, compared with those described in WO 2012/147635. In this example, the markers included in the QTL region linked to sugarcane smut resistance thus confirmed (i.e., AMP0014532, AMP0043152, AMP0069135, AMP0032477, AMP0018405, AMP0002312, AMP0007121, AMP0090108, and AMP0015886) were selected as selection markers (Table 10).

TABLE 10

| Varity | Linkage group | Marker | Nucleotide sequence information | SEQ ID NO: |
|---|---|---|---|---|
| Iriomote 15 | 15 | AMP0014532 | CAGAACGTGGTCGCCGTCGCCATGCTCCTTC GTAACATGCCTGAGCCATCGAATCCTGACAC TCGTCAAGCCCGAGATGAAATCCGAGGACTC ATCGAGACCGCTGCTATGCAGCAAACCGAGA GTTCTGCCTTGAGGTGAGGCGGGCCTACCTC GGAGCAG | SEQ ID NO: 135 |
| Iriomote 15 | 15 | AMP0043152 | CTCTGGCGAACGCGGTGAGGAGCACACCCAT GGTCTGCCCCGGCGAGATGACCAGCGTGGTG GCCGCTGTAGACCCCCACACGCCGCCCTGCA CTCTGCCTCCTTCCGAGGAGTTCGACCTCTT CGGC | SEQ ID NO: 136 |
| Iriomote 15 | 15 | AMP0069135 | GAGCACTTGATGTCACCTAATATACTGGTTC TGAGCCATTACCCGTTTGGGGTCCAATTAAT TTATGAAATGACTTGTTGTCAATTACCCTGA GTTTTTGTCCACTCTGAAGCTGAACTGAACA TTGTGTGCTCCGGTAGCTGAAAATCCTACCC TTAGCACTCAGACTGAGTCCATTGTTCTTAT CATAGCCTTATGGTTGTTCATTTTGTATGC | SEQ ID NO: 137 |
| Iriomote 15 | 15 | AMP0032477 | CTCGAGCGGTGTCCGACAGGAACAGGGGGAG TTGTCGTATGATGACCCGGTCGTCAGTGGCC CCACCCAACTGACAAGCCAAGTGGAAGTCAG CGAGCCAAAGTTTGGGTTTGGTTTCGCCGTT ATACTTGGTAAGAGTCGTGGGGGGCGGAAC CGAGCCGGGAGTAACATTTCATGAATGGCCT TGCTAAAGACCCGAGGTCCCGGTGGCTCGGG TGAAGGGCTTTGATCCTCCGA | SEQ ID NO: 138 |
| Iriomote 15 | 15 | AMP0018405 | CAGTAAGCTCCATCGAGGGACAAGCATCTAG TGAGTCAATACCAAAGTGGCGTGGGCATAA CCATACAGAGCCTGAAATGGGGAACGATCCA GAGTGGAATGCCAACTTGAATTGTACCAAAA CTCGGCAAGATGGATCCAATTATGCCACTTG TGGGGTACCGCATTGACAAAACAGCGTAAGA AGGTCTCCATGCACTGGTTGACGCGC | SEQ ID NO: 139 |
| Iriomote 15 | 15 | AMP0002312 | ACAGTGAACAGTGGTACTATATACAGTACCC GCTACAGCAACACACGTCGTGGTCTCCTTAG GCAGCAGAAATGGTATAAAAAAACGTACATA AAGGTACATGGCAGATAGGAGTATATTCTAT AAGGAGCACGTAACGCGTGACGGGTCACGCG TTCCAGCGTCGTCTACCTCGTGACAGGCCTC CTCCCTTGCCCCCTTCTCCCTCCCCGTGCCC CTCCTCCTCTGCCCCCTCCCTC | SEQ ID NO: 140 |
| Iriomote 15 | 15 | AMP0007121 | CAAAACAGGGACAATATATATCCTTTGTCTG CTTAATCAAAGCATGCCTTTTAGCTGCTTGA ATAAAACCATTCACATCTTGTATGTAGAAAG CTTCATATCTTCGTTTCGTGTACATCCATGA | SEQ ID NO: 141 |
| Iriomote 15 | 15 | AMP0090108 | GCCACCGGCCTCGTGGTCGTGAGACCGAGGA GACCGGTACCTGGGGATGGGCTGGTAGTCCT CATCAGTGCTGTCTGAAGTGACATCCTCAGG TATATCAGCAGTCTGAGTCTCAAGGTCCGCG AGCTCTGCCTCGGCAAGCTCGTCAACTCTGG CGTCCTGCTCAGCTGCTGTCTCAGGAACATC TGGGCGCTCAC | SEQ ID NO: 142 |
| Iriomote 15 | 15 | AMP0015886 | CAGAGGCCCTTGAAAGCACAGCTGGTTTTCA TCGTCACCCAGTGAAGAATGACATTTCGAGG AAGGCTTTAGGCTACTTGAATCCCACGAACA TTTCTACAGTAATATTGGTAATATGCGCAGA GGGTCCTTGGCTACTC | SEQ ID NO: 143 |

Whether or not genotypes of the markers; i.e., the line samples, have the selection markers was determined by designating the threshold of each number of reads as 10, evaluating as "present" when the number of reads is 10 or more, and evaluating as "absent" when the number of reads is less than 10 (FIGS. 10 to 18, Table 11).

TABLE 11

| Marker | NiF8 | Iriomote 15 | F1-1 | F1-2 | F1-3 | F1-4 | F1-5 | F1-6 | F1-7 | F1-8 | F1-9 | F1-10 | F1-11 | F1-12 |
|---|---|---|---|---|---|---|---|---|---|---|---|---|---|---|
| AMP0014532 | 0 | 18 | 0 | 12 | 25.6 | 0 | 22.5 | 0 | 0 | 0 | 12 | 25.6 | 0 | 22.5 |
| AMP0043152 | 0 | 215.3 | 0 | 1.1 | 188.4 | 217.6 | 186.5 | 1.1 | 1.1 | 0 | 1.1 | 188.4 | 217.6 | 186.5 |
| AMP0069135 | 0 | 13 | 0 | 0 | 12.8 | 14.8 | 19.3 | 0 | 1.1 | 0 | 0 | 12.8 | 14.8 | 19.3 |
| AMP0032477 | 0 | 23 | 0 | 0 | 19.8 | 28.5 | 22.5 | 0 | 0 | 0 | 0 | 19.8 | 28.5 | 22.5 |
| AMP0018405 | 0 | 150.2 | 0 | 1.1 | 150.1 | 191.4 | 216.5 | 0 | 1.1 | 0 | 1.1 | 150.1 | 191.4 | 216.5 |
| AMP0002312 | 0 | 42.1 | 0 | 0 | 45.4 | 28.5 | 33.2 | 0 | 0 | 0 | 0 | 45.4 | 28.5 | 33.2 |
| AMP0007121 | 0 | 51.1 | 0 | 0 | 51.2 | 61.5 | 62.2 | 0 | 0 | 0 | 0 | 51.2 | 61.5 | 62.2 |
| AMP0090108 | 0 | 24 | 0 | 0 | 24.4 | 29.6 | 24.6 | 0 | 0 | 0 | 0 | 24.4 | 29.6 | 24.6 |
| AMP0015886 | 113.9 | 76.1 | 0 | 75.5 | 104.7 | 234.6 | 194 | 0 | 98.6 | 0 | 75.5 | 104.7 | 234.6 | 194 |
| Incidence of smut (%) | 40.8 | 0 | 97.3 | 89.7 | 0 | 3.6 | 1.5 | 98.6 | 80.3 | 97.3 | 89.7 | 0 | 3.6 | 1.5 |

As shown in Table 11 and FIGS. 10 to 18, a line sample exhibiting a lower morbidity of smut was found to have a significantly larger number of markers than a line sample exhibiting a higher morbidity of smut. Such results demonstrate that continuous nucleic acid regions selected from the region of approximately 26.6 cM including AMP0014532, AMP0043152, AMP0069135, AMP0032477, AMP0018405, AMP0002312, AMP0007121, AMP0090108, and AMP0015886 can be used as the markers associated with sugarcane smut resistance.

Example 3

In this example, the marker associated with sugarcane smut resistance derived from the wild-type sugarcane line "Iriomote 8" was identified in the same manner as in Example 1, except for the use of the progeny line "KY09-6092" resulting from crossbreeding between the sugarcane variety "NiF8" and the wild-type sugarcane line "Iriomote 8," the progeny line "KY08-129" resulting from crossbreeding between the sugarcane variety "NiTn18" and the sugarcane variety "NiN24," and the 154 progeny lines resulting from crossbreeding between "KY09-6092" and "KY08-129."

In this example, the read data obtained in the same manner as in Example 1 except for the use of the forward primers shown in Table 12 instead of the forward primers shown in Table 5 for preparation of the DNA library for a next-generation sequencer were analyzed using analytical software (GRAS-Di, Toyota Motor Corporation) to obtain the genotype data of 57,444 markers.

TABLE 12

| No | Forward (5' → 3') | SEQ ID NO: |
|---|---|---|
| 1 | CAAGCAGAAGACGGCATACGAGATTCGTCAGAGTCTCGTGGGCTCGGAGATGTGTATAAGAGACAG | 152 |
| 2 | CAAGCAGAAGACGGCATACGAGATCGCTAGCGGTCTCGTGGGCTCGGAGATGTGTATAAGAGACAG | 153 |
| 3 | CAAGCAGAAGACGGCATACGAGATTCTCAGTAGTCTCGTGGGCTCGGAGATGTGTATAAGAGACAG | 154 |
| 4 | CAAGCAGAAGACGGCATACGAGATCGTAGATAGTCTCGTGGGCTCGGAGATGTGTATAAGAGACAG | 155 |
| 5 | CAAGCAGAAGACGGCATACGAGATATACGTGAGTCTCGTGGGCTCGGAGATGTGTATAAGAGACAG | 156 |
| 6 | CAAGCAGAAGACGGCATACGAGATGTCTAGAGGTCTCGTGGGCTCGGAGATGTGTATAAGAGACAG | 157 |
| 7 | CAAGCAGAAGACGGCATACGAGATAGTCGACAGTCTCGTGGGCTCGGAGATGTGTATAAGAGACAG | 158 |
| 8 | CAAGCAGAAGACGGCATACGAGATAGCGACGCGTCTCGTGGGCTCGGAGATGTGTATAAGAGACAG | 159 |
| 9 | CAAGCAGAAGACGGCATACGAGATTGATAGAGGTCTCGTGGGCTCGGAGATGTGTATAAGAGACAG | 160 |
| 10 | CAAGCAGAAGACGGCATACGAGATGACGACTGGTCTCGTGGGCTCGGAGATGTGTATAAGAGACAG | 161 |
| 11 | CAAGCAGAAGACGGCATACGAGATTGTGCTCAGTCTCGTGGGCTCGGAGATGTGTATAAGAGACAG | 162 |
| 12 | CAAGCAGAAGACGGCATACGAGATATGAGCTGGTCTCGTGGGCTCGGAGATGTGTATAAGAGACAG | 163 |
| 13 | CAAGCAGAAGACGGCATACGAGATTCTCTCACGTCTCGTGGGCTCGGAGATGTGTATAAGAGACAG | 164 |
| 14 | CAAGCAGAAGACGGCATACGAGATGCAGATCAGTCTCGTGGGCTCGGAGATGTGTATAAGAGACAG | 165 |
| 15 | CAAGCAGAAGACGGCATACGAGATTCTGCAGAGTCTCGTGGGCTCGGAGATGTGTATAAGAGACAG | 166 |
| 16 | CAAGCAGAAGACGGCATACGAGATACGTGAGCGTCTCGTGGGCTCGGAGATGTGTATAAGAGACAG | 167 |
| 17 | CAAGCAGAAGACGGCATACGAGATCGCGTGAGGTCTCGTGGGCTCGGAGATGTGTATAAGAGACAG | 168 |
| 18 | CAAGCAGAAGACGGCATACGAGATCATACTACGTCTCGTGGGCTCGGAGATGTGTATAAGAGACAG | 169 |
| 19 | CAAGCAGAAGACGGCATACGAGATTCTACACAGTCTCGTGGGCTCGGAGATGTGTATAAGAGACAG | 170 |
| 20 | CAAGCAGAAGACGGCATACGAGATGATAGATCGTCTCGTGGGCTCGGAGATGTGTATAAGAGACAG | 171 |

TABLE 12-continued

| No | Forward (5' → 3') | SEQ ID NO: |
|---|---|---|
| 21 | CAAGCAGAAGACGGCATACGAGATGAGCGTACGTCTCGTGGGCTCGGAGATGTGTATAAGAGACAG | 172 |
| 22 | CAAGCAGAAGACGGCATACGAGATCAGAGACAGTCTCGTGGGCTCGGAGATGTGTATAAGAGACAG | 173 |
| 23 | CAAGCAGAAGACGGCATACGAGATCATAGATGGTCTCGTGGGCTCGGAGATGTGTATAAGAGACAG | 174 |
| 24 | CAAGCAGAAGACGGCATACGAGATAGATGCTAGTCTCGTGGGCTCGGAGATGTGTATAAGAGACAG | 175 |
| 25 | CAAGCAGAAGACGGCATACGAGATCTCATCTCGTCTCGTGGGCTCGGAGATGTGTATAAGAGACAG | 176 |
| 26 | CAAGCAGAAGACGGCATACGAGATTATCTATGGTCTCGTGGGCTCGGAGATGTGTATAAGAGACAG | 177 |
| 27 | CAAGCAGAAGACGGCATACGAGATAGAGTATCGTCTCGTGGGCTCGGAGATGTGTATAAGAGACAG | 178 |
| 28 | CAAGCAGAAGACGGCATACGAGATGTGACTAGGTCTCGTGGGCTCGGAGATGTGTATAAGAGACAG | 179 |
| 29 | CAAGCAGAAGACGGCATACGAGATCTATGCTCGTCTCGTGGGCTCGGAGATGTGTATAAGAGACAG | 180 |
| 30 | CAAGCAGAAGACGGCATACGAGATCTGACTACGTCTCGTGGGCTCGGAGATGTGTATAAGAGACAG | 181 |
| 31 | CAAGCAGAAGACGGCATACGAGATTATCAGTAGTCTCGTGGGCTCGGAGATGTGTATAAGAGACAG | 182 |
| 32 | CAAGCAGAAGACGGCATACGAGATGAGTCTGCGTCTCGTGGGCTCGGAGATGTGTATAAGAGACAG | 183 |
| 33 | CAAGCAGAAGACGGCATACGAGATCAGTCGCAGTCTCGTGGGCTCGGAGATGTGTATAAGAGACAG | 184 |
| 34 | CAAGCAGAAGACGGCATACGAGATGACATCTAGTCTCGTGGGCTCGGAGATGTGTATAAGAGACAG | 185 |
| 35 | CAAGCAGAAGACGGCATACGAGATCTGTGACGGTCTCGTGGGCTCGGAGATGTGTATAAGAGACAG | 186 |
| 36 | CAAGCAGAAGACGGCATACGAGATAAGAGGCAGTCTCGTGGGCTCGGAGATGTGTATAAGAGACAG | 187 |
| 37 | CAAGCAGAAGACGGCATACGAGATCTAGTACGGTCTCGTGGGCTCGGAGATGTGTATAAGAGACAG | 188 |
| 38 | CAAGCAGAAGACGGCATACGAGATAGGAGTCCGTCTCGTGGGCTCGGAGATGTGTATAAGAGACAG | 189 |
| 39 | CAAGCAGAAGACGGCATACGAGATCATGCCTAGTCTCGTGGGCTCGGAGATGTGTATAAGAGACAG | 190 |
| 40 | CAAGCAGAAGACGGCATACGAGATGTAGAGAGGTCTCGTGGGCTCGGAGATGTGTATAAGAGACAG | 191 |
| 41 | CAAGCAGAAGACGGCATACGAGATCCTCTCTGGTCTCGTGGGCTCGGAGATGTGTATAAGAGACAG | 192 |
| 42 | CAAGCAGAAGACGGCATACGAGATAGCGTAGCGTCTCGTGGGCTCGGAGATGTGTATAAGAGACAG | 193 |
| 43 | CAAGCAGAAGACGGCATACGAGATTCCTCTACGTCTCGTGGGCTCGGAGATGTGTATAAGAGACAG | 194 |
| 44 | CAAGCAGAAGACGGCATACGAGATGACGTACAGTCTCGTGGGCTCGGAGATGTGTATAAGAGACAG | 195 |
| 45 | CAAGCAGAAGACGGCATACGAGATGACTGTAGGTCTCGTGGGCTCGGAGATGTGTATAAGAGACAG | 196 |
| 46 | CAAGCAGAAGACGGCATACGAGATTCAGTACAGTCTCGTGGGCTCGGAGATGTGTATAAGAGACAG | 197 |
| 47 | CAAGCAGAAGACGGCATACGAGATCATGATAGGTCTCGTGGGCTCGGAGATGTGTATAAGAGACAG | 198 |
| 48 | CAAGCAGAAGACGGCATACGAGATGCATCTCGGTCTCGTGGGCTCGGAGATGTGTATAAGAGACAG | 199 |
| 49 | CAAGCAGAAGACGGCATACGAGATTGCACAGAGTCTCGTGGGCTCGGAGATGTGTATAAGAGACAG | 200 |
| 50 | CAAGCAGAAGACGGCATACGAGATGAGCTATAGTCTCGTGGGCTCGGAGATGTGTATAAGAGACAG | 201 |
| 51 | CAAGCAGAAGACGGCATACGAGATAGTCTGCAGTCTCGTGGGCTCGGAGATGTGTATAAGAGACAG | 202 |
| 52 | CAAGCAGAAGACGGCATACGAGATCGCTGTGAGTCTCGTGGGCTCGGAGATGTGTATAAGAGACAG | 203 |
| 53 | CAAGCAGAAGACGGCATACGAGATCTGATGTGGTCTCGTGGGCTCGGAGATGTGTATAAGAGACAG | 204 |
| 54 | CAAGCAGAAGACGGCATACGAGATGCACTCTAGTCTCGTGGGCTCGGAGATGTGTATAAGAGACAG | 205 |
| 55 | CAAGCAGAAGACGGCATACGAGATTCTGCTCAGTCTCGTGGGCTCGGAGATGTGTATAAGAGACAG | 206 |
| 56 | CAAGCAGAAGACGGCATACGAGATTGTATCTAGTCTCGTGGGCTCGGAGATGTGTATAAGAGACAG | 207 |
| 57 | CAAGCAGAAGACGGCATACGAGATACAGTGAGGTCTCGTGGGCTCGGAGATGTGTATAAGAGACAG | 208 |
| 58 | CAAGCAGAAGACGGCATACGAGATATGCGATAGTCTCGTGGGCTCGGAGATGTGTATAAGAGACAG | 209 |
| 59 | CAAGCAGAAGACGGCATACGAGATGAGACATGGTCTCGTGGGCTCGGAGATGTGTATAAGAGACAG | 210 |

TABLE 12-continued

| No | Forward (5' → 3') | SEQ ID NO: |
|---|---|---|
| 60 | CAAGCAGAAGACGGCATACGAGATGTCATGTGGTCTCGTGGGCTCGGAGATGTGTATAAGAGACAG | 211 |
| 61 | CAAGCAGAAGACGGCATACGAGATTCATGATAGTCTCGTGGGCTCGGAGATGTGTATAAGAGACAG | 212 |
| 62 | CAAGCAGAAGACGGCATACGAGATGTCATCTCGTCTCGTGGGCTCGGAGATGTGTATAAGAGACAG | 213 |
| 63 | CAAGCAGAAGACGGCATACGAGATTATCTCTAGTCTCGTGGGCTCGGAGATGTGTATAAGAGACAG | 214 |
| 64 | CAAGCAGAAGACGGCATACGAGATCTGATATAGTCTCGTGGGCTCGGAGATGTGTATAAGAGACAG | 215 |
| 65 | CAAGCAGAAGACGGCATACGAGATTACGCATGGTCTCGTGGGCTCGGAGATGTGTATAAGAGACAG | 216 |
| 66 | CAAGCAGAAGACGGCATACGAGATCGTGAGTGGTCTCGTGGGCTCGGAGATGTGTATAAGAGACAG | 217 |
| 67 | CAAGCAGAAGACGGCATACGAGATGACACATGGTCTCGTGGGCTCGGAGATGTGTATAAGAGACAG | 218 |
| 68 | CAAGCAGAAGACGGCATACGAGATACATGACGGTCTCGTGGGCTCGGAGATGTGTATAAGAGACAG | 219 |
| 69 | CAAGCAGAAGACGGCATACGAGATGCGTCTAGGTCTCGTGGGCTCGGAGATGTGTATAAGAGACAG | 220 |
| 70 | CAAGCAGAAGACGGCATACGAGATTCACGCTGGTCTCGTGGGCTCGGAGATGTGTATAAGAGACAG | 221 |
| 71 | CAAGCAGAAGACGGCATACGAGATTCATGTACGTCTCGTGGGCTCGGAGATGTGTATAAGAGACAG | 222 |
| 72 | CAAGCAGAAGACGGCATACGAGATTAGTGACGGTCTCGTGGGCTCGGAGATGTGTATAAGAGACAG | 223 |
| 73 | CAAGCAGAAGACGGCATACGAGATCACGATAGGTCTCGTGGGCTCGGAGATGTGTATAAGAGACAG | 224 |
| 74 | CAAGCAGAAGACGGCATACGAGATACACACTGGTCTCGTGGGCTCGGAGATGTGTATAAGAGACAG | 225 |
| 75 | CAAGCAGAAGACGGCATACGAGATAGCATCACGTCTCGTGGGCTCGGAGATGTGTATAAGAGACAG | 226 |
| 76 | CAAGCAGAAGACGGCATACGAGATTAGTCGTAGTCTCGTGGGCTCGGAGATGTGTATAAGAGACAG | 227 |
| 77 | CAAGCAGAAGACGGCATACGAGATGCATCGCGGTCTCGTGGGCTCGGAGATGTGTATAAGAGACAG | 228 |
| 78 | CAAGCAGAAGACGGCATACGAGATATCATGTCGTCTCGTGGGCTCGGAGATGTGTATAAGAGACAG | 229 |
| 79 | CAAGCAGAAGACGGCATACGAGATGTACTCTAGTCTCGTGGGCTCGGAGATGTGTATAAGAGACAG | 230 |
| 80 | CAAGCAGAAGACGGCATACGAGATAGTGCATAGTCTCGTGGGCTCGGAGATGTGTATAAGAGACAG | 231 |
| 81 | CAAGCAGAAGACGGCATACGAGATCGCATCAGGTCTCGTGGGCTCGGAGATGTGTATAAGAGACAG | 232 |
| 82 | CAAGCAGAAGACGGCATACGAGATCGCTATAGGTCTCGTGGGCTCGGAGATGTGTATAAGAGACAG | 233 |
| 83 | CAAGCAGAAGACGGCATACGAGATGTCGATAGGTCTCGTGGGCTCGGAGATGTGTATAAGAGACAG | 234 |
| 84 | CAAGCAGAAGACGGCATACGAGATACACAGTAGTCTCGTGGGCTCGGAGATGTGTATAAGAGACAG | 235 |
| 85 | CAAGCAGAAGACGGCATACGAGATCAGATGTAGTCTCGTGGGCTCGGAGATGTGTATAAGAGACAG | 236 |
| 86 | CAAGCAGAAGACGGCATACGAGATCTCTACAGGTCTCGTGGGCTCGGAGATGTGTATAAGAGACAG | 237 |
| 87 | CAAGCAGAAGACGGCATACGAGATGTCACTAGGTCTCGTGGGCTCGGAGATGTGTATAAGAGACAG | 238 |
| 88 | CAAGCAGAAGACGGCATACGAGATTGTACTAGGTCTCGTGGGCTCGGAGATGTGTATAAGAGACAG | 239 |
| 89 | CAAGCAGAAGACGGCATACGAGATACGCTATGGTCTCGTGGGCTCGGAGATGTGTATAAGAGACAG | 240 |
| 90 | CAAGCAGAAGACGGCATACGAGATATGTATAGGTCTCGTGGGCTCGGAGATGTGTATAAGAGACAG | 241 |
| 91 | CAAGCAGAAGACGGCATACGAGATTGTGACAGGTCTCGTGGGCTCGGAGATGTGTATAAGAGACAG | 242 |

Figure 19:
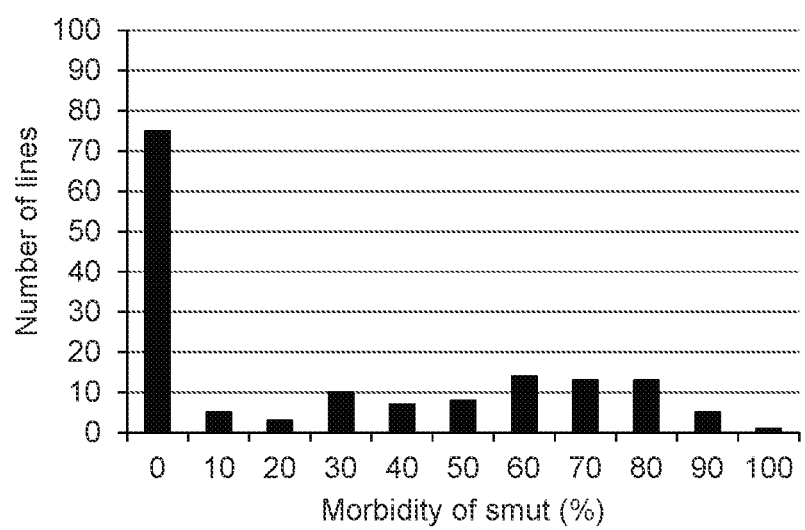
FIG. 19 shows a characteristic diagram showing the results of calculation of the morbidity of smut for progeny lines resulting from crossing between "KY09-6092" and "KY08-129."

Among them, 2,936 genotypes of KY09-6092 and 1,877 genotypes of KY08-129 were obtained. The genetic map data comprising 117 linkage groups derived from "KY09-6092" and the genetic map data comprising 123 linkage groups derived from "KY08-129" were obtained. In addition, the smut resistance test data of the 154 progeny lines resulting from crossbreeding between "KY09-6092" and "KY08-129" were obtained under the same conditions as in Example 1, and the results of calculation of the morbidity of smut were shown in FIG. 19. Based on the genetic map data and the smut resistance test data, QTL analysis was carried out by the composite interval mapping (CIM) method using the QTL Cartographer gene analysis software (statgen.ncs-u.edu/qtlcart/cartographer.html). The LOD threshold was determined to be 2.5.

As a result, the presence of QTL linked to sugarcane smut resistance was confirmed in a region of approximately 12.27 cM including the markers AMP0063683 to AMP0091501 in the 8th linkage group of "KY09-6092" (Table 13 and FIG.

20). When the value indicating the effect is negative, QTL is linked to a trait of improving smut resistance.

TABLE 13

| Linkage group | Position (cM) | Range (cM) | Adjacent marker | LOD value | Effects (%) |
|---|---|---|---|---|---|
| 8 | 83.8 | 12.27 | AMP0063683-AMP0091501 | 68.7 | −54.2 |

Figure 20:
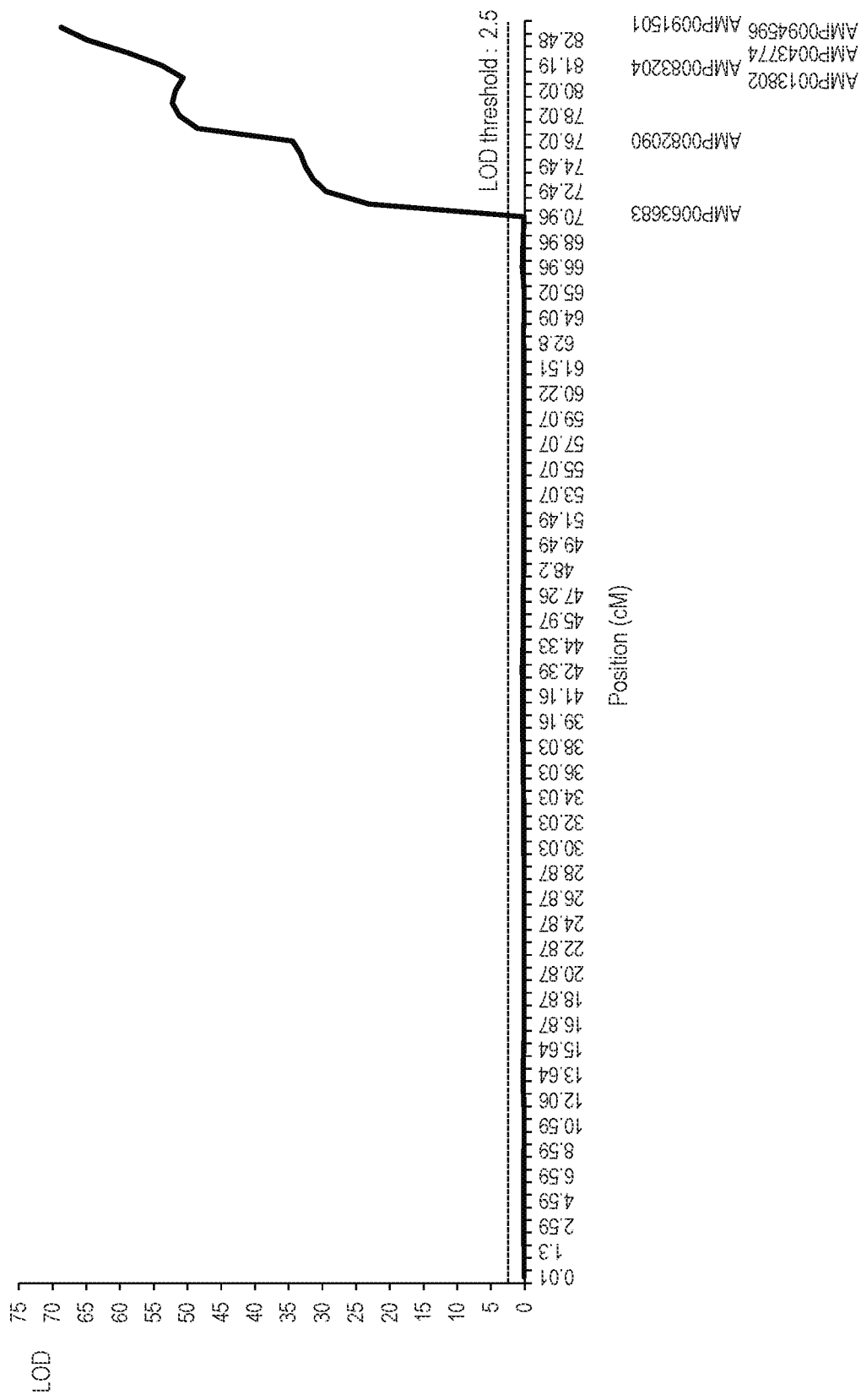
FIG. 20 shows a characteristic diagram showing the results of QTL analysis of smut resistance performed in Example 3.
Figure 21:
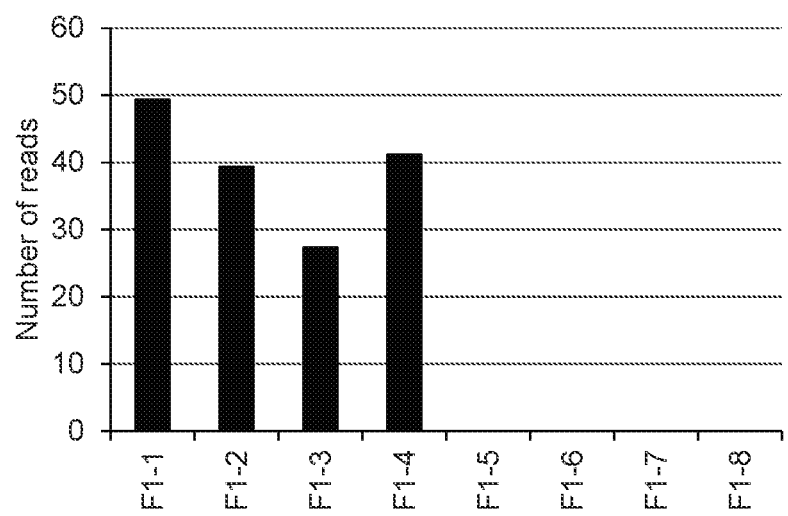
FIG. 21 shows a characteristic diagram showing the number of reads of AMP0063683 in each line.
Figure 22:
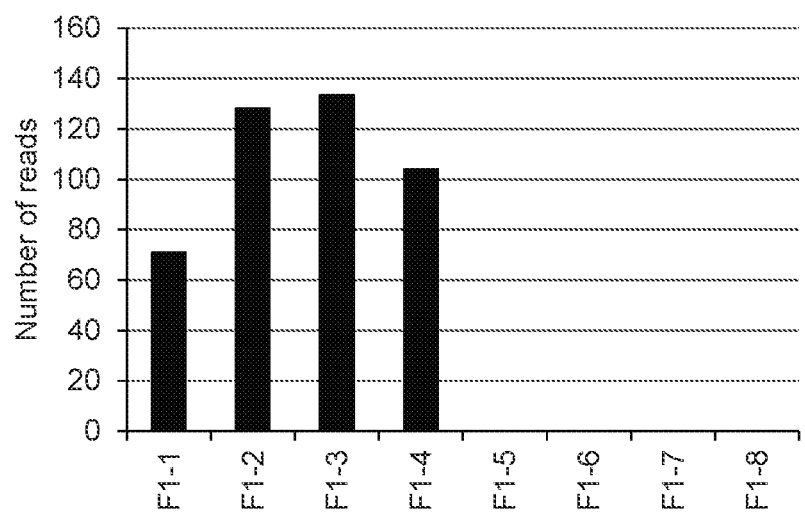
FIG. 22 shows a characteristic diagram showing the number of reads of AMP0082090 in each line.
Figure 23:
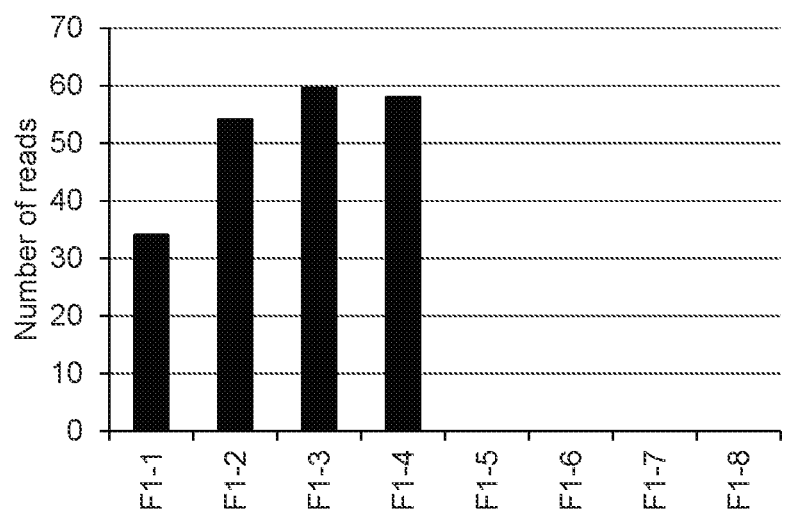
FIG. 23 shows a characteristic diagram showing the number of reads of AMP0013802 in each line.
Figure 24:
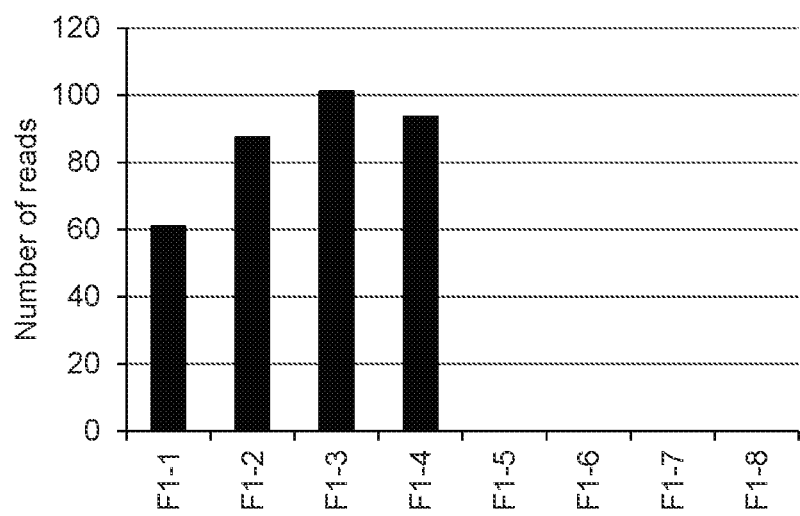
FIG. 24 shows a characteristic diagram showing the number of reads of AMP0083204 in each line.
Figure 25:
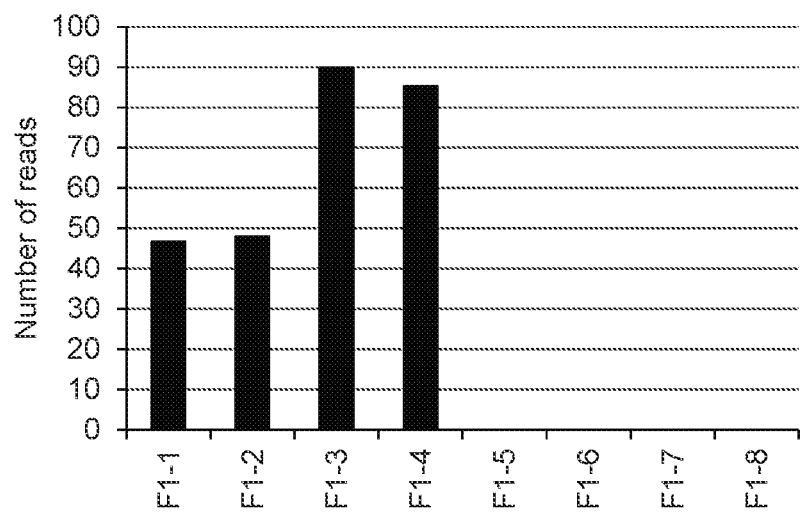
FIG. 25 shows a characteristic diagram showing the number of reads of AMP0043774 in each line.
Figure 26:
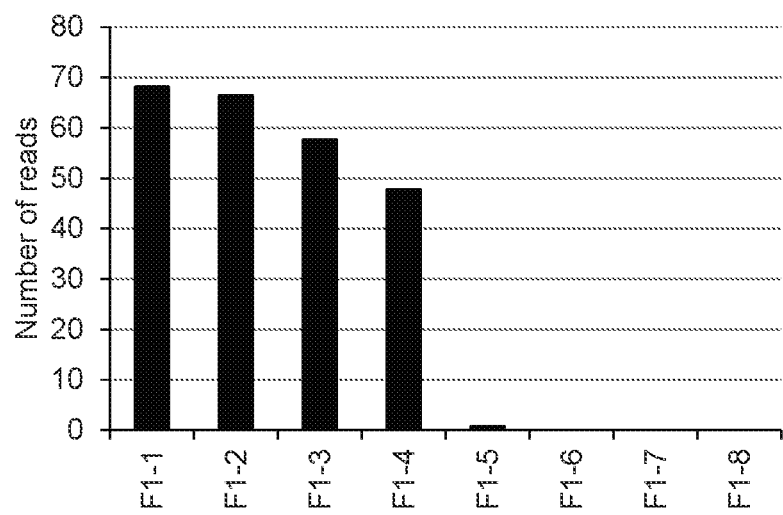
FIG. 26 shows a characteristic diagram showing the number of reads of AMP0094596 in each line.
Figure 27:
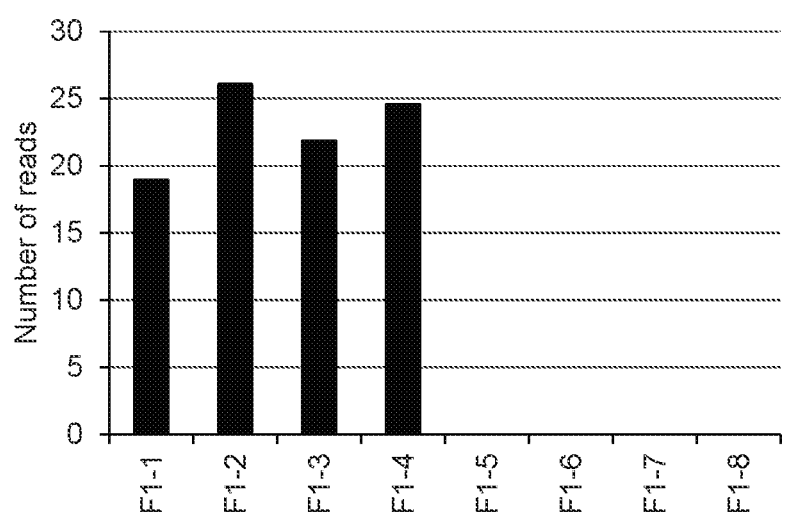
FIG. 27 shows a characteristic diagram showing the number of reads of AMP0091501 in each line.

As shown in Table 13 and FIG. 20, the range including the markers AMP0063683 to AMP0091501 in the 8th linkage group observed in this example was found to exhibit a significantly higher LOD value and significantly improved effects, compared with those described in WO 2012/147635. The markers included in the QTL region linked to sugarcane smut resistance confirmed in this example (i.e., AMP0063683, AMP0082090, AMP0013802, AMP0083204, AMP0043774, AMP0094596, and AMP0091501) were selected as selection markers (Table 14).

TABLE 14

| Varity | Linkage group | Marker | PCR amplicon sequence | SEQ ID NO: |
|---|---|---|---|---|
| Iriomote 8 | 8 | AMP0063683 | Read 1 (5'→3') GATCCCGGAGGAAGTTCAGGA CCGGCCAGAGCAGCCAGAGGT ACCAACCGGCGACGAAGCTCC TGCCGAAGATCTACCCGAGTG TCCTGACCACCGGCCC (SEQ ID NO: 144) Read 2 (5'→3') TACAATGCAGCAAGTGTTTTC ATATAACTCCTAGAACTTAAT GCAATAAACAATTAAAAGTAC TCAAGATAGATTTATAAAAAT GATGGGTTCAGCATGC (SEQ ID NO: 145) | SEQ ID NOs: 144, 145 |
| Iriomote 8 | 8 | AMP0082090 | GCGGAAAATAGACCAATGTAT TAGGCTATCCATTGCCGATAT GCAAAAGAATGAATCCATAAT GATAGCCGCCGCTCACTTCTG GTCAGACACCACAAATACCTT TATGTTTGGTCATGGTCCATC CGCCCCTACTCTTGCCGATGT ATACATGCTCACCGACTTAGA TATCTCA | SEQ ID NO: 146 |
| Iriomote 8 | 8 | AMP0013802 | CAGGAACTTGCAAACAAGCTC GGGTGCACAGATCCAAATCAT TTGGTCGGTTGATGTGGACTC CGATGTGGACTCAAATGC | SEQ ID NO: 147 |
| Iriomote 8 | 8 | AMP0083204 | GCGTGGCAGAGGATGGGGGCA CGACAGGGATGGCACCGTGGC GAGGGGAGGAGCACGGTGTGG CAGGGAAAGGAGCGCGGCGAG CTTGACGCCGGGGCGCAACC AGGATGAGGATTGAGTCACGG ATGGTTGGAC | SEQ ID NO: 148 |
| Iriomote 8 | 8 | AMP0043774 | GAAAACAAGCTCTACCACTGG CACAACACGGGCTCACAGGTC ACAGCTCTGCTTGCTCAGTGG TACTACGAGTGCTAGCACGGG AGCGCTGTTGGACGGATCGCC AGCATGAAATGCCCACCGCGC ACGTACTGC | SEQ ID NO: 149 |
| Iriomote 8 | 8 | AMP0094596 | TACCCCACCAAAAAGCCTATC ATGATCCTTGGTGTCATTTTA TTTTTGGTTCTGTCAGGTAAG TCTAGCTGAGTACCTTCTCAT ACTCAGGGCTTTGTTCCCACT TGTTACAGATGGACAGATGTA CTATGGTTATTGTATCA | SEQ ID NO: 150 |
| Iriomote 8 | 8 | AMP0091501 | TAACCCACCAAAGATAGCCTT GCATGCTCCTTAGTGTCGCTT ATTTTGGTTTAAGACGGGTAA GTCTAGCTGAGTACCTTCTCG TACTCAGGGCGTTGTTCTCAT TGTTGTTGCAGATGGTTAGAT GTACTATGGATATTGCGTCA | SEQ ID NO: 151 |

Among the markers shown in Table 14, the PCR product of AMP0063683 is 200 bp or larger. Thus, AMP0063683 is defined as a nucleic acid region comprising Read 1 (SEQ ID NO: 144) and Read 2 (SEQ ID NO: 145) with the nucleotide sequences being determined using the next-generation sequencer at both ends.

Whether or not genotypes of the markers; i.e., the line samples, have the selection markers was determined by designating the threshold of each number of reads as 10, evaluating as "present" when the number of reads is 10 or more, and evaluating as "absent" when the number of reads is less than 10 (FIGS. 21 to 27, Table 15).

TABLE 15

| Marker | F1-1 | F1-2 | F1-3 | F1-4 | F1-5 | F1-6 | F1-7 | F1-8 |
|---|---|---|---|---|---|---|---|---|
| AMP0063683 | 49.4 | 39.4 | 27.4 | 41.2 | 0 | 0 | 0 | 0 |
| AMP0082090 | 70.9 | 128.1 | 133.4 | 104.1 | 0 | 0 | 0 | 0 |
| AMP0013802 | 34.1 | 54.2 | 59.6 | 58.1 | 0 | 0 | 0 | 0 |
| AMP0083204 | 61 | 87.5 | 101.2 | 93.7 | 0 | 0 | 0 | 0 |
| AMP0043774 | 46.7 | 48 | 89.9 | 85.3 | 0 | 0 | 0 | 0 |
| AMP0094596 | 68.2 | 66.5 | 57.7 | 47.8 | 0.8 | 0 | 0 | 0 |
| AMP0091501 | 19 | 26.1 | 21.9 | 24.6 | 0 | 0 | 0 | 0 |
| Incidence of smut (%) | 0 | 0 | 0 | 0 | 70.28 | 18.8 | 61.74 | 52.63 |

As shown in Table 15 and FIGS. 21 to 27, line samples with the low morbidity of smut have a significantly larger number of markers than line samples with the high morbidity of smut. This demonstrates that continuous nucleic acid regions selected from a region of approximately 12.27 cM comprising AMP0063683, AMP0082090, AMP0013802, AMP0083204, AMP0043774, AMP094596, and AMP0091501 can be used as the markers associated with sugarcane smut resistance.

Example 4

In this example, the nucleotide sequence of the region of approximately 8.4 cM comprising the marker associated with sugarcane smut resistance derived from JW90 identified in Example 1 was compared with the nucleotide sequence of the region of approximately 12.27 cM comprising the marker associated with sugarcane smut resistance derived from Iriomote 8 identified in Example 3. As a result, the adjacent region comprising AMP0121265 located at 0 cM among the markers associated with sugarcane smut resistance derived from JW90 identified in Example 1 and the adjacent region comprising AMP0091501 located at 83.76 cM among the markers associated with sugarcane smut resistance derived from Iriomote 8 identified in Example 3 were found to comprise a plurality of markers having the identical nucleotide sequence.

Table 16 summarizes markers included in the adjacent region comprising AMP0121265 located at 0 cM among the markers associated with sugarcane smut resistance derived from JW90 identified in Example 1. Table 17 summarizes markers included in the adjacent region comprising AMP0091501 located at 83.76 cM among the markers associated with sugarcane smut resistance derived from Iriomote 8 identified in Example 3. In Tables 16 and 17, the column indicating the nucleotide sequence information of markers shows the nucleotide sequences of contig sequences when the contig sequences can be led from a pair of read data obtained via analysis using a next-generation sequencer, or a pair of read sequences (the read sequence 1 and the read sequence 2) when the contig sequence cannot be led. Specifically, the markers shown in Tables 16 and 17 can be defined by the nucleotide sequences of the contig sequences or the nucleotide sequences of the read sequence 1 and the read sequence 2.

Among the markers shown in Table 16, concerning the markers having the identical nucleotide sequence with the markers included in the adjacent region including AMP0179276 shown in Table 17, the column indicating "Presence or absence of DNA marker derived from Iriomote 8 ( ): Iriomote 8 marker ID" shows "Present" and ID of the marker derived from Iriomote 8 having the identical nucleotide sequence. Similarly, among the markers shown in Table 17, concerning the markers having the identical nucleotide sequence with the markers included in the adjacent region including AMP0121265 shown in Table 16, the column indicating "Presence or absence of DNA marker derived from JW90 ( ): JW90 marker ID" shows "Present" and ID of the marker derived from JW90 having the identical nucleotide sequence.

TABLE 16

| Marker ID | Origin | Nucleotide sequence information SEQ ID NO: | Presence or absence of DNA marker derived from iriomote 8 (): Marker ID |
|---|---|---|---|
| AMP0129420 | JW90 | ACAGGGAAGTGAAAGAGAAGTGGCCATTGAA AAACCTAATATTGTTACGGAAGTGCCTCGCG TCCGCGTCGAAGCTCGTCCAAAGCCTCATGA GCTGGTCTGGTATGACTGGCGCATTCAGCTC GA SEQ ID NO: 243 | — |
| AMP0010186 | JW90 | CAAGCGCAGGAAAAGGAAACGCTGCCCGCAG TTCCTCACCCGGCTCCCCCGTTGTCGCCCTC AGCCGCTTCCGCCATCCTCGCTGTCAC SEQ ID NO: 244 | — |
| AMP0010846 | JW90 | CAATAAAATGGGAACATGATGGAAGGACAGG TTACCCGATGCATTATGAGCATACAGAACGG CCTACAAAACACCGATTGGAATGTCACCATA TCAACTTATCTATGGAAGA SEQ ID NO: 245 | — |

TABLE 16-continued

| Marker ID | Origin | Nucleotide sequence information | SEQ ID NO: | Presence or absence of DNA marker derived from iriomote 8 (): Marker ID |
|---|---|---|---|---|
| AMP0015478 | JW90 | CAGACAGATAGCCACGAGACGAGGACTCACA GAGCTTTCGGTGAGCCTCCATAGTCCAGAGA TAGTCTCTGTTGGTTCTTTTTCTTTCCTTTT TCGACGAGATCTTTTTTTCTTGGTCCCACAC GAACTGGCGTTGTGCTTCTATTATGCTGTCA C | SEQ ID NO: 246 | — |
| AMP0019992 | JW90 | CATCATGGTGCGAATCTTCGAGTTCAGACCC CTCATAAAACAAGCTTGCTTCTTTCGATCTG AGTTGATTTGGTCAGCTGCATACTATGATAA ATGATTGAACCTACCCACATATTGCATC | SEQ ID NO: 247 | — |
| AMP0020554 | JW90 | CATGAAAGCTCACAAACCCGCTCGAGCTCTG GGTCGATGGCTCATCCCATTTGCCTCGAGAA TGCCCCTCCTCCGCTGCGCAGGTGCCGCCTC TCCTTACATCACGCGTCACCATGCCATGCCC GC | SEQ ID NO: 248 | Present (AMP0016471) |
| AMP0022987 | JW90 | Read 1 (5'→3') CTAATGCTTGGTAGCTCATACATGAACCTTA TAGTCGTCCTGCATTTAACAACTGTCAAGGA CAGGTTCGAGTGCACATGTATAATGCTATCA ACGTTTT (SEQ ID NO: 249) Read 2 (5'→3') TAGCCACATAACTTTCCCACAATGTAAAGGT ATTTTCAATAAAGAATCTAGGAGTACTAATT CTATGTTTTCAATCTATACAATCATTGGCAT ATTGATG (SEQ ID NO: 250) | SEQ ID NOs: 249, 250 | — |
| AMP0130766 | JW90 | CTCGAAAATCTCTAACAAACTCATTCCAAGT AATAGGAGGAGCATTGTTAGGACGTGCAGCT TGATACGACTCCCACCAAGTCTGTGTTGTCC CCTGTAACTGACCAGTTGCATATAACACCTT TTCCATATCATTGCATTGAGCGATGTTCA | SEQ ID NO: 251 | — |
| AMP0030465 | JW90 | Read 1 (5'→3') CTCGAGCGATGTCCGATAGGAACAGGGGAAG TTGTCGAATGATGACCCGGTCGTCGGTGGCC CCACCCAACTGACTAGCCAAGCGGAAGTCAG CGAGCCA (SEQ ID NO: 252) Read 2 (5'→3') TCGGAGGATCGAAGCCCTTCACCCGAGCCAC CAGGCCCTCGGGTCTTTAGCAAAGCCATCCG CAAAACGTTACTCCCAGCTCGGTTCCTCCCC CATGACT (SEQ ID NO: 253) | SEQ ID NOs: 252, 253 | — |
| AMP0031132 | JW90 | Read 1 (5'→3') CTCGAGCGGTGTCAGAGAGGAACAGGGGGAG CTGCCGGATGATGTTCCGGTCGTCGGTGGCC CCGCCCAGCTGACACGCCAAGCGGAAATCGG CGAGCCA (SEQ ID NO: 254) Read 2 (5'→3') TCGGAGGATCGTAGCCCTTCACCCGAGCCTC CGGGCCCTCGGGTCTTCAGTAAGGCTATTCG TGAAATGATACTCCCGGCGCGGTTTCGCCCC CCCCCCA (SEQ ID NO: 255) | SEQ ID NOs: 254, 255 | — |

TABLE 16-continued

| Marker ID | Origin | Nucleotide sequence information | SEQ ID NO: | Presence or absence of DNA marker derived from iriomote 8 (): Marker ID |
|---|---|---|---|---|
| AMP0033330 | JW90 | Read 1 (5'→3')<br>CTCGAGCGGTGTCGAAGAGGAACAGAGGGAG<br>CTGTCGGATGATGACCTGGTCGTCGGTGGCC<br>CCACCCAGCTGACATGCCAAGCGGAAATCGG<br>CGAGCCA<br>(SEQ ID NO: 256)<br>Read 2 (5'→3')<br>TCGGAGGATCGCAGCCCATCACCCGAGCCTC<br>CAGGCCCTCGGGTCTTCAGTAAGGCTATCCG<br>CGAAACTATACTCCCGGCGCAGTTTCGCCCT<br>CCCACGA<br>(SEQ ID NO: 257) | SEQ ID NOs: 256, 257 | — |
| AMP0036149 | JW90 | Read 1 (5'→3')<br>CTCGAGCGGTGTCGGAGAGGAACAGGGGGAG<br>CTGTCGGATGATGACCCGGTCGTCGGTGGCC<br>CCACCCAGCTGACACGCCAAGCGGAAATCGG<br>CGAGCCA<br>(SEQ ID NO: 258)<br>Read 2 (5'→3')<br>TCGGAGGATCGTAGCCCTTCACCCGAGCCTC<br>CGGGCCCTCGGGTCTTCAGTAAGGCTATCCG<br>CGAAATAATACTCCCGGCGCGGTTTCGCCCT<br>CCCACGA<br>(SEQ ID NO: 259) | SEQ ID NOs: 258, 259 | — |
| AMP0036465 | JW90 | Read 1 (5'→3')<br>CTCGAGCGGTGTCGGAGAGGAACAGGGGGAG<br>CTGTCGGATGATGACCCGGTCGTCGGTGGCC<br>CCGCCCAGCTGACATGCCAAGCGGAAATCGG<br>CGAGCCA<br>(SEQ ID NO: 260)<br>Read 2 (5'→3')<br>TCGGAGGATCGAAGCCCTTCACCCGAGCCTC<br>CGGGCCCTCGGGTCTTCAGCAAGGCTATCCG<br>CGAAACGATACTCCTGGCGCGGTTTCGCCCT<br>CCCACGA<br>(SEQ ID NO: 261) | SEQ ID NOs: 260, 261 | — |
| AMP0039231 | JW90 | Read 1 (5'→3')<br>CTCGAGCGGTGTTAGAGAGGAACAGGGGGAG<br>CTGTCGGATGATGACCCGGTCGTCGGTGGCC<br>CCACCCAGCTGACATGCCAAGCGGAAATCGG<br>CAAGCCA<br>(SEQ ID NO: 262)<br>Read 2 (5'→3')<br>TCGGAGGATCGTAGCCCTTCACCCGAGCCTC<br>CGGGCCCTCGGGTCTTCAGTAAGGCTATCCG<br>CGAAACGATACTCCCGGCGCGGTTTCGCCCT<br>CCCACGA<br>(SEQ ID NO: 263) | SEQ ID NOs: 262, 263 | — |
| AMP0040432 | JW90 | Read 1 (5'→3')<br>CTCGGGCGGTATCGGAGAGGAATAGGGGGAG<br>TTGTCGGATGATGACCCGGTCGTCGGTGGCC<br>CCGCCTAGCTAACACGCCAAGCAGAAATCGG<br>CGAGCCA<br>(SEQ ID NO: 264)<br>Read 2 (5'→3')<br>TCAGAAGATCGTAGCCCTTCACCCGAGCCTC<br>CGGGCTCTCGGGTCTTTAGTAAGGCTATCCG<br>CGAGACGGTGCTCCCGGCTCGGTTTCGCCCT<br>CCCACGA<br>(SEQ ID NO: 265) | SEQ ID NOs: 264, 265 | — |
| AMP0041203 | JW90 | Read 1 (5'→3')<br>CTCGGGCGGTGTCGGAGAGGAACAGGGGGAG<br>TTATCGAATGATGACCCGGTCGTCGGTGGCC<br>CCGCCCAGCTGACACGCCAAGCGGAAATCGG<br>TGAGCCA<br>(SEQ ID NO: 266)<br>Read 2 (5'→3')<br>TCGGAAGATCGTAGTCCTTCACCCGAGCCTC<br>CGGGCCCTCTGGTCTTCTGTAAAGCTATCCG | SEQ ID NOs: 266, 267 | — |

TABLE 16-continued

| Marker ID | Origin | Nucleotide sequence information | SEQ ID NO: | Presence or absence of DNA marker derived from iriomote 8 (): Marker ID |
|---|---|---|---|---|
| | | TGAAATGGTGCTCCCGGCTCAGTTTCGCCCT<br>CCCACGA<br>(SEQ ID NO: 267) | | |
| AMP0041520 | JW90 | Read 1 (5'→3')<br>CTCGGGCGGTGTCGGAGAGGAACAGGGGGAG<br>TTGTCGAATGATAACCCGGTCGTCGGTGGCC<br>CCACCCAGCTGACATGCCAAGCGGAAATCAG<br>CAAGCCA<br>(SEQ ID NO: 268)<br>Read 2 (5'→3')<br>TCGAAAGATCGTAGTCCTTCACCCGAGCCTC<br>CGGGCCCTCGGGTCTTCAGTAAGGCTATCCG<br>TGAAACGGTGCTCCCATCTCGGTTTCGCCCT<br>CCCACGA<br>(SEQ ID NO: 269) | SEQ ID NOs: 268, 269 | — |
| AMP0045000 | JW90 | CTGAGTCTAGTAATAAGACTTTGATCAAGCT<br>TATCAAGAAGAAAATTGAGGAAAATTCAAGG<br>AGGTGGCATGAAGTTTTGTCTGAAGCTCTAT<br>GGGCACATCGTATTTCAAAACATGGTGCTAC<br>CAAAGTTATTCCTTTTAAGCTAGTATATGAC<br>CAAGAGGCCGTGTTA | SEQ ID NO: 270 | Present<br>(AMP0035426) |
| AMP0057239 | JW90 | GAAGCTACTGTTGGTTGGGAGCTAATCGGAA<br>TGACTATTTATCATTTTTTGAAAATAAAAAG<br>GGATGACTGATACTTATGCACA | SEQ ID NO: 271 | Present<br>(AMP0046626) |
| AMP0059273 | JW90 | GACAATGCATCACGCCGATGTAGCCGAGATC<br>ATCCCTTCGCTGCCCCTGGAGATCAGGTGGC<br>CACCGTTCCGTCTCCGCCATTAC | SEQ ID NO: 272 | — |
| AMP0062853 | JW90 | GACCACGCGGGCGACATCGACACCAGCAAGA<br>GCACGAGCGGGATTCTCTTCTTCCTCGGCAG<br>GTGCCTCGTTAGCTGGCAGTCGGTCAAGCAG<br>CAGGTGGTGGCCCTGTCCAGCTGCGAGGCCG<br>AGTACATAGCGGCTTCCACCGCTTCGACTTA<br>GGCGC | SEQ ID NO: 273 | Present<br>(AMP0052709) |
| AMP0064313 | JW90 | GACCTGGCAGGCGACGTGAATGACTGAAAGA<br>GCACCAGCGGGCTGATCTTCTTCCTGGCAGG<br>AGGCCCGATTGCTTGGCAGTCGGCAAAACAG<br>AGGGTGGTTGC | SEQ ID NO: 274 | — |
| AMP0132654 | JW90 | Read 1 (5'→3')<br>GAGATGAGAGGAGCGAGGAAAGGAGAGGAAG<br>GGAGGTGAGGTGTTGTAGTGTGGATACAGCT<br>AACAGCTTACATGGAGGTGGAGTATGGGGCC<br>TGGTTTA<br>(SEQ ID NO: 275)<br>Read 2 (5'→3')<br>GCGCAGGAAAGAGGTCGTGGACAAATCCAGG<br>GCGTGTTTAGTTGGGCTGATTTTGGACGTCC<br>AAAATCTGCACAGTGTAAGATTCCATACTGT<br>AGCATTT<br>(SEQ ID NO: 276) | SEQ ID NOs: 275, 276 | — |
| AMP0070602 | JW90 | Read 1 (5'→3')<br>GAGCGAGACGAGAGACAAACAAAAAGGTGGT<br>GACGATAAGAGGCGCCACGCACTAAACCCGC<br>ACCATGGTCATGGAGTAGCGTGTAAGGAACA<br>AGTAGCA<br>(SEQ ID NO: 277)<br>Read 2 (5'→3')<br>GCGAGAGGTGGTGGTACACGCCTACCTAGGT<br>GGTGGGCTCGTCGTCGTCAGACACCAGGCGT<br>CACAGGCCGTCGTCCGTTTCTGCCGCCCCAT<br>GCTCGCT<br>(SEQ ID NO: 278) | SEQ ID NOs: 277, 278 | — |

TABLE 16-continued

| Marker ID | Origin | Nucleotide sequence information | SEQ ID NO: | Presence or absence of DNA marker derived from iriomote 8 (): Marker ID |
|---|---|---|---|---|
| AMP0133317 | JW90 | Read 1 (5'→3')<br>GCACGACATGGTATGGCAGGGGACAAAGACG<br>GAGATGGGGTGCGCCGTGGGGGATGGCTTCA<br>GCGACATGCCAGAGTGGGCCACGGCGCGACA<br>GAGTGGG<br>(SEQ ID NO: 279)<br>Read 2 (5'→3')<br>GCTGCTCCCTTCTCCGGCGCGAGGCTCCTCG<br>TCGTGGCCTTCTCTAGCGCGGTGGCACCGCA<br>TCCGCTCCCATCCCGCGCTGCTCCACACTCC<br>GCGCGCG<br>(SEQ ID NO: 280) | SEQ ID NOs: 279, 280 | — |
| AMP0090028 | JW90 | Read 1 (5'→3')<br>GCCACCGGCCTCGTGGTCGTGAGACCGAGGA<br>GACCGGTACCTGGGATGGGCTGGTAGTCCTC<br>ATCTGTGCTGTCAGAAGTCACATCCTCAGGT<br>ATATCAG<br>(SEQ ID NO: 281)<br>Read 2 (5'→3')<br>GTGAGCGCCCAGACGTTCCTGAGACAGCAGC<br>TGAGCAGGATGCCAGAGTTGACGAGCTTGCT<br>GAGGCAGAGCTTGCGGACCTTGAGGCTCAGA<br>CTGCTGA<br>(SEQ ID NO: 282) | SEQ ID NOs: 281, 282 | — |
| AMP0100461 | JW90 | GCGGTTGTGTGTTGTGGCCGGGCCATTGGCG<br>GATGAGCGAGCGAGTGCAACCAGAGGCGAAC<br>GTACCCAACCCAGCGACAGCAAGTCAGCAAC<br>ATATATTCTCACTCGATCACGTCCCCACG<br>GGCCTA | SEQ ID NO: 283 | — |
| AMP0134140 | JW90 | GCTAAGAACATTCGGTGTCTGCAATGTGAGA<br>AGTGAACACTCTAGTAACTTAAGAAATGCTA<br>TCAACAAAATGAGCCATCTTGTTCATCTAGA<br>CATTGCGGCTCTAGGGGAGAGCGAAGTGTTG<br>CAGCTAGAGGGACTTCATTTGCCTCCA | SEQ ID NO: 284 | — |
| AMP0103131 | JW90 | Read 1 (5'→3')<br>GGCAGAGGGAGCCAAGCAACTAATCAAACTC<br>AAAGCGCCTCCTACCAACCGAAAAGGCGAGA<br>AAAAGCTAAGCCAAGGTGGGGATCGGAAGAA<br>TTATCCA<br>(SEQ ID NO: 285)<br>Read 2 (5'→3')<br>TAGCAAGTGCGGCTGCTATCTTGAGAGGTTG<br>GCGCTGTGGTGCTAGGCTTTTTGCCGTGCTG<br>GGTGCCTGGGTGGTGGAGATGGATGGATGTA<br>TATATAG<br>(SEQ ID NO: 286) | SEQ ID NOs: 285, 286 | — |
| AMP0105230 | JW90 | GTATGTCACCTTTGAGGGTTTTGACTTTTAA<br>TGAATTTGCAACTATGGCACCCAATTTTTGC<br>AGCTGTAGTGTTGCTTCCATCATCAGTCAGG<br>TCTACACCTACCAAATAATTCTAGTGTTCCA<br>TGGCTCCAATGAAATGTGGATTGAAAGTTAA<br>TCTTAATTGCATTA | SEQ ID NO: 287 | — |
| AMP0107179 | JW90 | GTGAGCGCCCAGATGTTCCTGAGACAGCAGC<br>TGAGCAGGACGCTACAGTTGACGAGCTTGCT<br>GAGGCAGAGCTCGCAGACCTTGAGACTCAGA<br>CTGCTGACATACCTGAGGATGTCACTTCAGA<br>TAGCACAGATGAGGACTACCAGCCCATTCCC<br>AGGTA | SEQ ID NO: 288 | — |
| AMP0107330 | JW90 | GTGAGCGCCCAGATGTTCGTGAGACAGCAGC<br>TGAGCAGGACGCTACAGTTGACGAGCTTGCT<br>GAGGCAGAGCTCGCGGATCTTGAGGCTCAGA<br>CTGCTGACATACCTGAGGATGCCACTTCTGA<br>TAGCACAGATGAGGACTACCAGCCCATTCCC<br>AGGTA | SEQ ID NO: 289 | — |

TABLE 16-continued

| Marker ID | Origin | Nucleotide sequence information | SEQ ID NO: | Presence or absence of DNA marker derived from iriomote 8 (): Marker ID |
|---|---|---|---|---|
| AMP0108751 | JW90 | Read 1 (5'→3')<br>GTGGGGCGTGTGTCTCACCCAACGAAGTAGT<br>GGCCAAGTAAGGTAGCCAGCGGTGGGCGAGC<br>TCCTTATTTGATGACGTGGTCCAGAAAATGG<br>TTCTCTT<br>(SEQ ID NO: 290)<br>Read 2 (5'→3')<br>TCATGTCCAAGTACTCGCAAGCTGATGCTTG<br>GGGGCTACAACCACTGGGGTCTCCTGAGCGC<br>AAATTGTCAGGATCGCGCGCTGATTCTACCA<br>CGCGGCC<br>(SEQ ID NO: 291) | SEQ ID NOs: 290, 291 | — |
| AMP0111891 | JW90 | TAACCCACCAAAGATAGCCTTGCATGCTCCT<br>TAGTGTCGCTTATTTTGGTTTAAGACGGGTA<br>AGTCTAGCTGAGTACCTTCTCGTACTCAGGG<br>CGTTGTTCTCATTGTTGTTGCAGATGGTTAG<br>ATGTACTATGGATATTGCGTCA | SEQ ID NO: 292 | Present<br>(AMP0091501) |
| AMP0121265 | JW90 | TAGCCCACTAAAAGAAAGCCTTGCATAACCC<br>TTGATGTCACTTTATTTTGGTTTAAGACAGA<br>TAAGTCTAGCTGAGTACCTTCTCGTACTTAG<br>GGCGTTGTTCCCATTGTTGTTGTAGATGATT<br>AGATGTACTACGGCTATTGCGTCA | SEQ ID NO: 293 | — |
| AMP0135444 | JW90 | TCAAATGAAGGCCAAGCGTCAAGCAGTGAGC<br>ATTCTTTCAATTTCTTGGCAACCCA | SEQ ID NO: 294 | — |

TABLE 17

| Marker ID | Origin | Nucleotide sequence information | SEQ ID NO: | Presence or absence of JW90DNA marker (): Marker ID |
|---|---|---|---|---|
| AMP0007142 | Iriomote 8 | CAAAGTCTAGTAGGTACTCTCGAGACCCTCA<br>TACGCTCTGATGGCGGCGAACATAGCACTCA<br>TTGCCTGGTTGTCGCTAG | SEQ ID NO: 295 | — |
| AMP0008511 | Iriomote 8 | Read 1 (5'→3')<br>CAAGCACTGGGTTGATTCTGGCAACTACGGC<br>ATCAAATTTGTTCCTCTGGGACCGGGCTTCT<br>TGCTCCAGCACATCGAACTGTGCCTTGACCC<br>TCTGATG<br>(SEQ ID NO: 296)<br>Read 2 (5'→3')<br>GCGAGCGAACAAACTGACCGAGGAGCTTAAC<br>GGTAAGTATCCACTGGTCGGGTTTTCTGCTG<br>TAGCGATTGTCTTGCCTGATGGAACTTCAAA<br>ATGCATG<br>(SEQ ID NO: 297) | SEQ ID NOs: 296, 297 | — |
| AMP0016471 | Iriomote 8 | CATGAAAGCTCACAAACCCGCTCGAGCTCTG<br>GGTCGATGGCTCATCCCATTTGCCTCGAGAA<br>TGCCCCTCCTCCGCTGCGCAGGTGCCGCCTC<br>TCCTTACATCACGCGTCACCATGCCATGCCC<br>GC | SEQ ID NO: 298 | Present<br>(AMP0020554) |
| AMP0017797 | Iriomote 8 | Read 1 (5'→3')<br>CTAAAGGAAGAAACCAACACGACAAAAAACA<br>GAAAAGGTACGTACCAGCGTGGAAGTTCTCA<br>AGGGTGGAGAATTCCTCGGCCTGCCGAGCCA<br>CCTGCTC<br>(SEQ ID NO: 299)<br>Read 2 (5'→3')<br>GCGGAGCACCTTGGTGTCGGAGCAGAACGCC<br>TTGGAGTTGGCTTGGAATGCCCTGGAGTCAA<br>AGCGAAATGCCTGGTCAGAGGCGGACCAGGA<br>GGTGCTC<br>(SEQ ID NO: 300) | SEQ ID NOs: 299, 300 | — |

TABLE 17-continued

| Marker ID | Origin | Nucleotide sequence information | SEQ ID NO: | Presence or absence of JW90DNA marker (): Marker ID |
|---|---|---|---|---|
| AMP0033151 | Iriomote 8 | Read 1 (5'→3')<br>CTCGGGCGGTGTCGGAGAGGAACAGGGGGAG<br>TTGTCGAATGATAACCCGGTCGTCGGTGGCC<br>CCACCCAGCTGACATGCCAAGCGGAAATCGG<br>CAAGCCA<br>(SEQ ID NO: 301)<br>Read 2 (5'→3')<br>TCGAAAGATCGTAGTCCTTCACCCGAGCCTC<br>CGGGCCCTCGGGTCTTCAGTAAGGCTATCCG<br>TGAAACGGTGCTCCCGGCTCGGTTTCGCCCT<br>CCCACGA<br>(SEQ ID NO: 302) | SEQ ID NOs: 301, 302 | — |
| AMP0036426 | Iriomote 8 | CTGAGTCTAGTAATAAGACTTTGATCAAGCT<br>TATCAAGAAGAAAATTGAGGAAAATTCAAGG<br>AGGTGGCATGAAGTTTTGTCTGAAGCTCTAT<br>GGGCACATCGTATTTCAAAACATGGTGCTAC<br>CAAAGTTATTCCTTTTAAGCTAGTATATGAC<br>CAAGAGGCCGTGTTA | SEQ ID NO: 303 | Present (AMP0045000) |
| AMP0038963 | Iriomote 8 | Read 1 (5'→3')<br>CTGGAAGGGTGATTTAGTCTCTGATCGGAAG<br>GCCTAGCTAAGGAGGAACAACGCTCGCTTGC<br>GACTCTGACCTGCCTCTCCGACCGGAAGGCC<br>TGGCCAA<br>(SEQ ID NO: 304)<br>Read 2 (5'→3')<br>TCGGAGTCAGAATCGAGCGTCGTTCCTCCTT<br>GGCTAGGCCTTTTGGTTGGAGAGGCGGGTCA<br>GAGTTAGAAGCGAGCATCGTTCCTCCTTGGC<br>CAGGCCT<br>(SEQ ID NO: 305) | SEQ ID NOs: 304, 305 | — |
| AMP0039429 | Iriomote 8 | CTGGCACCTCCTCCAAACTCTTTCCTTCTCT<br>CCTCTCTCTATTTCTAAAGACTAGATCCTAA<br>TAAGGACTAATCTTCTCTCGATA | SEQ ID NO: 306 | — |
| AMP0090720 | Iriomote 8 | GAAGCTACTGTTGGTTGGGAGCTAATCGGAA<br>TGACTATTTATCATTTTTTGAAAATAAAAAG<br>GGATGACTGATACTTATGCACA | SEQ ID NO: 307 | Present (AMP0057239) |
| AMP0047005 | Iriomote 8 | Read 1 (5'→3')<br>GAAGGGTGGTAGGTGGGCATCGAACGGACCT<br>GGTACATGGGCTTGGGAAAGCCATAGAAGTC<br>GTAGATGGTGTCGTTGCTGCCGCGGATAACG<br>TTGACCG<br>(SEQ ID NO: 308)<br>Read 2 (5'→3')<br>GCGGGCAGACCCAAACCAGAGACGCGGCACG<br>CGACGCGGGAGGGCGAGGAGCAGCGGCGGCG<br>CGGCGACATCGCGAGGCCAGGGCCAGACGCA<br>ACGGCCG<br>(SEQ ID NO: 309) | SEQ ID NOs: 308, 309 | — |
| AMP0048243 | Iriomote 8 | GACACACGACACGAGAGTTTGGCCATGGCAA<br>CGGTCTCCTCGCTCGCTCGCTCCTCACTGGC<br>GGCCGTCACACCTGGAGAGTGACCGACTGGC<br>AGTAGCTGTAGCAGCCCTCAGCCTCACGCGA<br>CGCAGCGCAGGCCTCTGGATGC | SEQ ID NO: 310 | — |
| AMP0052709 | Iriomote 8 | GACCACGCGGGCGACATCGACACCAGCAAGA<br>GCACGAGCGGGATTCTCTTCTTCCTCGGCAG<br>GTGCCTCGTTAGCTGGCAGTCGGTCAAGCAG<br>CAGGTGGTGGCCCTGTCCAGCTGCGAGGCCG<br>AGTACATAGCGGCTTCCACCGCTTCGACTTA<br>GGCGC | SEQ ID NO: 311 | Present (AMP0062853) |

TABLE 17-continued

| Marker ID | Origin | Nucleotide sequence information | SEQ ID NO: | Presence or absence of JW90DNA marker (): Marker ID |
|---|---|---|---|---|
| AMP0054926 | Iriomote 8 | Read 1 (5'→3')<br>GACGCGGCGATCAGGCCGGAAGGAGTCGTGG<br>CGCCGCCGTCCGTGAGCTTACCTGATTGATT<br>TGATTGATTGTTGCATTGGTTAATTATTATT<br>AGTTACT<br>(SEQ ID NO: 312)<br>Read 2 (5'→3')<br>GAGAATGCCGGTGAGCAGGATCGCCGTGGGC<br>GCTCCGGGCGAGCTGTCCCACCCCGACACCG<br>CCAAGGCCGCCGTCGCCGAGTTCATCTCCAT<br>GCTCATC<br>(SEQ ID NO: 313) | SEQ ID NOs: 312, 313 | — |
| AMP0059174 | Iriomote 8 | GAGCGGCGGCGACGGCGGAAATGGAGAGGGC<br>GGTGGGGGAAAGCGGCCTAGGGTTCGAGGG<br>GAGAGGGAATGGATACGATTGAGGGGTGAGG<br>GGCGCGGGGATGGGGCGA | SEQ ID NO: 314 | — |
| AMP0059536 | Iriomote 8 | GAGGACAGCGACCAGAGCTGGAGGAGGATCG<br>ATCGGCGGAGGGTGGTCTGTTATGTTCCGTG<br>ACCAGGCGTGACTCCGTGTCGCATATGATTA<br>GGGAAAGGATATGAACCGTGAGCTCCGTGGC<br>GCTGAAGTTGCGCCGGTTAGCTGGTCACTGA | SEQ ID NO: 315 | — |
| AMP0091501 | Iriomote 8 | TAACCCACCAAAGATAGCCTTGCATGCTCCT<br>TAGTGTCGCTTATTTTGGTTTAAGACGGGTA<br>AGTCTAGCTGAGTACCTTCTCGTACTCAGGG<br>CGTTGTTCTCATTGTTGTTGCAGATGGTTAG<br>ATGTACTATGGATATTGCGTCA | SEQ ID NO: 316 | Present<br>(AMP0111891) |
| AMP0101156 | Iriomote 8 | TAGCCCACTAAAATAAAACCTTGCATACTCC<br>TTGGTGTCACTTTATTTCTGTTTAAGGCGGG<br>TAAGTCTAGCTGAGTACCCTCTCGTACTCAG<br>GGCTTTGTTCCTATTGTTGTTGCAGATGGCC<br>AGATGTACTATGGTTATTGCATCA | SEQ ID NO: 317 | — |
| AMP0107476 | Iriomote 8 | TCGGAACGTCAAGGCCAAGTACATGAGCTCT<br>GGAGCACTCAGAAGCCAGACATCGATCAACT<br>CATGTTGAGCCATCAGCGAGCCGTGTCGATC<br>CATCAAACAAGCCGTCCGA | SEQ ID NO: 318 | — |

As shown in Table 16, the adjacent region comprising AMP0121265 located at 0 cM among the markers associated with sugarcane smut resistance derived from JW90 was found to comprise 36 markers. As shown in Table 17, the adjacent region comprising AMP0091501 located at 83.76 cM among the markers associated with sugarcane smut resistance derived from Iriomote 8 was found to comprise 18 markers. Among them, 5 markers were found to comprise the identical nucleotide sequence. On the basis of such results, the region comprising the 36 markers shown in Table 16 and the region comprising the 18 markers shown in Table 17 can be regarded as QTLs that are highly correlated with sugarcane smut resistance. In particular, both JW90 and Iriomote 8 have the QTL of sugarcane smut resistance identified in this example. Accordingly, such QTL is considered to be present in an extensive range of sugarcane varieties without particular limitation.

In particular, this example demonstrates that the 36 markers shown in Table 16 and the 18 markers shown in Table 17 can be used as particularly excellent markers associated with sugarcane smut resistance.

Among the 36 markers shown in Table 16 and the 18 markers shown in Table 17, in addition, 5 markers that were found to have the identical nucleotide sequence (i.e., AMP0016471 (SEQ ID NO: 298)=AMP0020554 (SEQ ID NO: 248), AMP0036426 (SEQ ID NO: 303)=AMP0045000 (SEQ ID NO: 270), AMP0046626 (SEQ ID NO: 307)=AMP0057239 (SEQ ID NO: 271), AMP0052709 (SEQ ID NO: 311)=AMP0062853 (SEQ ID NO: 273), and AMP0091501 (SEQ ID NO: 316)=AMP0111891 (SEQ ID NO: 292)) were found to be usable as the most excellent markers associated with sugarcane smut resistance.

All publications, patents, and patent applications cited herein are incorporated herein by reference in their entirety.

The invention claimed is:

1. A method for producing a sugarcane line having improved smut resistance, the method comprising:
   a step of breeding parent plants to obtain a progeny plant, wherein at least one of said parent plants is a sugarcane plant;
   a step of extracting a genomic DNA of the progeny plant;
   a step of determining the presence or absence of a marker associated with sugarcane smut resistance in the obtained genomic DNA;
   a step of selecting a progeny plant having the marker associated with sugarcane smut resistance, and
   a step of breeding only the selected progeny plant;
   wherein the marker associated with sugarcane smut resistance comprises any nucleotide sequence selected from the group consisting of the nucleotide sequences of SEQ ID NOs:1 to 6, or at least 15 consecutive nucleotides of SEQ ID NOs:1 to 6.

2. The method for producing a sugarcane line according to claim 1, wherein the step of determination involves the use of a DNA chip comprising a probe corresponding to the marker associated with sugarcane smut resistance.

3. The method for producing a sugarcane line according to claim 1, wherein the progeny plant is a seed or young seedling and the genomic DNA is extracted from the seed or young seedling.

4. The method for producing a sugarcane line according to claim 1, wherein the nucleic acid region comprises the nucleotide sequence of SEQ ID NO:1 or 2 or at least 15 consecutive nucleotides of SEQ ID NOs: 1 or 2.

5. The method for producing a sugarcane line according to claim 1, wherein the at least one of said parent plants is a smut-resistant strain of sugarcane.

6. The method for producing a sugarcane line according to claim 5, wherein the smut-resistant strain of sugarcane is selected from the group consisting of JW90, Iriomote 15, and Iriomote 8.

* * * * *

SEQUENCE LISTING

<160> NUMBER OF SEQ ID NOS: 318

<210> SEQ ID NO 1
<211> LENGTH: 148
<212> TYPE: DNA
<213> ORGANISM: Saccharum spontaneum

<400> SEQUENCE: 1

```
tagcccacta aaagaaagcc ttgcataacc cttgatgtca ctttattttg gtttaagaca      60
gataagtcta gctgagtacc ttctcgtact tagggcgttg ttcccattgt tgttgtagat     120
gattagatgt actacggcta ttgcgtca                                        148
```

<210> SEQ ID NO 2
<211> LENGTH: 169
<212> TYPE: DNA
<213> ORGANISM: Saccharum spontaneum

<400> SEQUENCE: 2

```
tagagcggag ggcgttggag cgtctaggaa tagatcgcgt tctctccagt ggcgagccga      60
tctgagtggg aggacgtgga tggggctcac gcggcgagga ggatgtggat gcggcgccgt     120
cctggttcct gctcaaccac agcgacgctg gcggctactg cacggtgga               169
```

<210> SEQ ID NO 3
<211> LENGTH: 237
<212> TYPE: DNA
<213> ORGANISM: Saccharum spontaneum

<400> SEQUENCE: 3

```
ctcgagcggt gtcggagagg aacaggggga gctgccggat gatgacccgg tcgtcggtgg      60
ccccacccag ctgacacgcc aagcggaaat cggcgagcca agttcgggt ttggtctcgc      120 tgttgtactt ggtgagagtc gtgggggcg aaaccgcgcc gggagtatca tttcacgaat     180
agccttactg aagacccgag ggcccggagg ctcgggtgaa gggctacgat cctccga       237
```

<210> SEQ ID NO 4
<211> LENGTH: 142
<212> TYPE: DNA
<213> ORGANISM: Saccharum spontaneum

<400> SEQUENCE: 4

```
taccccacca aaaagcctat catgatcctt ggtgtcattt tattttggtt ctgtcgggta      60
agtctagctg agtaccttct cgtactcagg gctttgttcc cacttgttgc agatggacag     120
atgtagtatg gttattgtat ca                                              142
```

<210> SEQ ID NO 5
<211> LENGTH: 197
<212> TYPE: DNA
<213> ORGANISM: Saccharum spontaneum

<400> SEQUENCE: 5

```
gccaccggcc tcgtggtcgt gagaccgagg agaacggtac ctgggtatgg gctggtagtc      60
ctcatccgtg ctgtcagaag tcacatcctc aggaagatca gcaggctgag cgtcaagatc     120
ggcaagctct gcctctgcaa gctcatcaac tgtggcgtct tgctcagctg ctgtctcagg     180
aacctcaggt cgctcac                                                    197
```

<210> SEQ ID NO 6
<211> LENGTH: 167

<212> TYPE: DNA
<213> ORGANISM: Saccharum spontaneum

<400> SEQUENCE: 6

```
gcggtgaata acgcgcaaag ggtgagaagg ctcacaccgg atctacgggt tacacagagg    60
tacacatcca tcgattctaa cacgggcgtc cggctcggcg ccggggcgcg gcgaggggtg   120
gagtggatag aactcgcaga agaagacgtg ttactgtctg tccgcac                167
```

<210> SEQ ID NO 7
<211> LENGTH: 13
<212> TYPE: DNA
<213> ORGANISM: Artificial
<220> FEATURE:
<223> OTHER INFORMATION: Synthetic DNA

<400> SEQUENCE: 7

```
taagagacag aga                                                      13
```

<210> SEQ ID NO 8
<211> LENGTH: 13
<212> TYPE: DNA
<213> ORGANISM: Artificial
<220> FEATURE:
<223> OTHER INFORMATION: Synthetic DNA

<400> SEQUENCE: 8

```
taagagacag agc                                                      13
```

<210> SEQ ID NO 9
<211> LENGTH: 13
<212> TYPE: DNA
<213> ORGANISM: Artificial
<220> FEATURE:
<223> OTHER INFORMATION: Synthetic DNA

<400> SEQUENCE: 9

```
taagagacag cgt                                                      13
```

<210> SEQ ID NO 10
<211> LENGTH: 13
<212> TYPE: DNA
<213> ORGANISM: Artificial
<220> FEATURE:
<223> OTHER INFORMATION: Synthetic DNA

<400> SEQUENCE: 10

```
taagagacag cta                                                      13
```

<210> SEQ ID NO 11
<211> LENGTH: 13
<212> TYPE: DNA
<213> ORGANISM: Artificial
<220> FEATURE:
<223> OTHER INFORMATION: Synthetic DNA

<400> SEQUENCE: 11

```
taagagacag ctc                                                      13
```

<210> SEQ ID NO 12
<211> LENGTH: 13
<212> TYPE: DNA
<213> ORGANISM: Artificial
<220> FEATURE:
<223> OTHER INFORMATION: Synthetic DNA

```
<400> SEQUENCE: 12
taagagacag gct                                                          13

<210> SEQ ID NO 13
<211> LENGTH: 13
<212> TYPE: DNA
<213> ORGANISM: Artificial
<220> FEATURE:
<223> OTHER INFORMATION: Synthetic DNA

<400> SEQUENCE: 13
taagagacag gta                                                          13

<210> SEQ ID NO 14
<211> LENGTH: 13
<212> TYPE: DNA
<213> ORGANISM: Artificial
<220> FEATURE:
<223> OTHER INFORMATION: Synthetic DNA

<400> SEQUENCE: 14
taagagacag gtc                                                          13

<210> SEQ ID NO 15
<211> LENGTH: 13
<212> TYPE: DNA
<213> ORGANISM: Artificial
<220> FEATURE:
<223> OTHER INFORMATION: Synthetic DNA

<400> SEQUENCE: 15
taagagacag tac                                                          13

<210> SEQ ID NO 16
<211> LENGTH: 13
<212> TYPE: DNA
<213> ORGANISM: Artificial
<220> FEATURE:
<223> OTHER INFORMATION: Synthetic DNA

<400> SEQUENCE: 16
taagagacag tca                                                          13

<210> SEQ ID NO 17
<211> LENGTH: 13
<212> TYPE: DNA
<213> ORGANISM: Artificial
<220> FEATURE:
<223> OTHER INFORMATION: Synthetic DNA

<400> SEQUENCE: 17
taagagacag tga                                                          13

<210> SEQ ID NO 18
<211> LENGTH: 13
<212> TYPE: DNA
<213> ORGANISM: Artificial
<220> FEATURE:
<223> OTHER INFORMATION: Synthetic DNA

<400> SEQUENCE: 18
taagagacag ttg                                                          13

<210> SEQ ID NO 19
<211> LENGTH: 66
```

<212> TYPE: DNA
<213> ORGANISM: Artificial
<220> FEATURE:
<223> OTHER INFORMATION: Synthetic DNA

<400> SEQUENCE: 19
caagcagaag acggcatacg agattcgtca gagtctcgtg ggctcggaga tgtgtataag    60
agacag                                                               66

<210> SEQ ID NO 20
<211> LENGTH: 66
<212> TYPE: DNA
<213> ORGANISM: Artificial
<220> FEATURE:
<223> OTHER INFORMATION: Synthetic DNA

<400> SEQUENCE: 20
caagcagaag acggcatacg agatcgctag cggtctcgtg ggctcggaga tgtgtataag    60
agacag                                                               66

<210> SEQ ID NO 21
<211> LENGTH: 66
<212> TYPE: DNA
<213> ORGANISM: Artificial
<220> FEATURE:
<223> OTHER INFORMATION: Synthetic DNA

<400> SEQUENCE: 21
caagcagaag acggcatacg agattctcag tagtctcgtg ggctcggaga tgtgtataag    60
agacag                                                               66

<210> SEQ ID NO 22
<211> LENGTH: 66
<212> TYPE: DNA
<213> ORGANISM: Artificial
<220> FEATURE:
<223> OTHER INFORMATION: Synthetic DNA

<400> SEQUENCE: 22
caagcagaag acggcatacg agatcgtaga tagtctcgtg ggctcggaga tgtgtataag    60
agacag                                                               66

<210> SEQ ID NO 23
<211> LENGTH: 66
<212> TYPE: DNA
<213> ORGANISM: Artificial
<220> FEATURE:
<223> OTHER INFORMATION: Synthetic DNA

<400> SEQUENCE: 23
caagcagaag acggcatacg agatacgagc aggtctcgtg ggctcggaga tgtgtataag    60
agacag                                                               66

<210> SEQ ID NO 24
<211> LENGTH: 66
<212> TYPE: DNA
<213> ORGANISM: Artificial
<220> FEATURE:
<223> OTHER INFORMATION: Synthetic DNA

<400> SEQUENCE: 24
caagcagaag acggcatacg agatatacgt gagtctcgtg ggctcggaga tgtgtataag    60

-continued agacag 66

<210> SEQ ID NO 25
<211> LENGTH: 66
<212> TYPE: DNA
<213> ORGANISM: Artificial
<220> FEATURE:
<223> OTHER INFORMATION: Synthetic DNA

<400> SEQUENCE: 25
caagcagaag acggcatacg agatgtctag aggtctcgtg ggctcggaga tgtgtataag     60
agacag                                                                66

<210> SEQ ID NO 26
<211> LENGTH: 66
<212> TYPE: DNA
<213> ORGANISM: Artificial
<220> FEATURE:
<223> OTHER INFORMATION: Synthetic DNA

<400> SEQUENCE: 26
caagcagaag acggcatacg agatagtcga cagtctcgtg ggctcggaga tgtgtataag     60
agacag                                                                66

<210> SEQ ID NO 27
<211> LENGTH: 66
<212> TYPE: DNA
<213> ORGANISM: Artificial
<220> FEATURE:
<223> OTHER INFORMATION: Synthetic DNA

<400> SEQUENCE: 27
caagcagaag acggcatacg agatctcaca gagtctcgtg ggctcggaga tgtgtataag     60
agacag                                                                66

<210> SEQ ID NO 28
<211> LENGTH: 66
<212> TYPE: DNA
<213> ORGANISM: Artificial
<220> FEATURE:
<223> OTHER INFORMATION: Synthetic DNA

<400> SEQUENCE: 28
caagcagaag acggcatacg agatagacat aggtctcgtg ggctcggaga tgtgtataag     60
agacag                                                                66

<210> SEQ ID NO 29
<211> LENGTH: 66
<212> TYPE: DNA
<213> ORGANISM: Artificial
<220> FEATURE:
<223> OTHER INFORMATION: Synthetic DNA

<400> SEQUENCE: 29
caagcagaag acggcatacg agatagcgac gcgtctcgtg ggctcggaga tgtgtataag     60
agacag                                                                66

<210> SEQ ID NO 30
<211> LENGTH: 66
<212> TYPE: DNA
<213> ORGANISM: Artificial
<220> FEATURE:
<223> OTHER INFORMATION: Synthetic DNA

<400> SEQUENCE: 30
caagcagaag acggcatacg agattgatag aggtctcgtg ggctcggaga tgtgtataag    60
agacag                                                               66

<210> SEQ ID NO 31
<211> LENGTH: 66
<212> TYPE: DNA
<213> ORGANISM: Artificial
<220> FEATURE:
<223> OTHER INFORMATION: Synthetic DNA

<400> SEQUENCE: 31
caagcagaag acggcatacg agatgacgac tggtctcgtg ggctcggaga tgtgtataag    60
agacag                                                               66

<210> SEQ ID NO 32
<211> LENGTH: 66
<212> TYPE: DNA
<213> ORGANISM: Artificial
<220> FEATURE:
<223> OTHER INFORMATION: Synthetic DNA

<400> SEQUENCE: 32
caagcagaag acggcatacg agattgtgct cagtctcgtg ggctcggaga tgtgtataag    60
agacag                                                               66

<210> SEQ ID NO 33
<211> LENGTH: 66
<212> TYPE: DNA
<213> ORGANISM: Artificial
<220> FEATURE:
<223> OTHER INFORMATION: Synthetic DNA

<400> SEQUENCE: 33
caagcagaag acggcatacg agatatgagc tggtctcgtg ggctcggaga tgtgtataag    60
agacag                                                               66

<210> SEQ ID NO 34
<211> LENGTH: 66
<212> TYPE: DNA
<213> ORGANISM: Artificial
<220> FEATURE:
<223> OTHER INFORMATION: Synthetic DNA

<400> SEQUENCE: 34
caagcagaag acggcatacg agattctctc acgtctcgtg ggctcggaga tgtgtataag    60
agacag                                                               66

<210> SEQ ID NO 35
<211> LENGTH: 66
<212> TYPE: DNA
<213> ORGANISM: Artificial
<220> FEATURE:
<223> OTHER INFORMATION: Synthetic DNA

<400> SEQUENCE: 35
caagcagaag acggcatacg agatgcagat cagtctcgtg ggctcggaga tgtgtataag    60
agacag                                                               66

<210> SEQ ID NO 36

```
<211> LENGTH: 66
<212> TYPE: DNA
<213> ORGANISM: Artificial
<220> FEATURE:
<223> OTHER INFORMATION: Synthetic DNA

<400> SEQUENCE: 36
caagcagaag acggcatacg agattctgca gagtctcgtg ggctcggaga tgtgtataag    60
agacag                                                               66

<210> SEQ ID NO 37
<211> LENGTH: 66
<212> TYPE: DNA
<213> ORGANISM: Artificial
<220> FEATURE:
<223> OTHER INFORMATION: Synthetic DNA

<400> SEQUENCE: 37
caagcagaag acggcatacg agatacgtga gcgtctcgtg ggctcggaga tgtgtataag    60
agacag                                                               66

<210> SEQ ID NO 38
<211> LENGTH: 66
<212> TYPE: DNA
<213> ORGANISM: Artificial
<220> FEATURE:
<223> OTHER INFORMATION: Synthetic DNA

<400> SEQUENCE: 38
caagcagaag acggcatacg agatcgcgtg aggtctcgtg ggctcggaga tgtgtataag    60
agacag                                                               66

<210> SEQ ID NO 39
<211> LENGTH: 66
<212> TYPE: DNA
<213> ORGANISM: Artificial
<220> FEATURE:
<223> OTHER INFORMATION: Synthetic DNA

<400> SEQUENCE: 39
caagcagaag acggcatacg agatcatact acgtctcgtg ggctcggaga tgtgtataag    60
agacag                                                               66

<210> SEQ ID NO 40
<211> LENGTH: 66
<212> TYPE: DNA
<213> ORGANISM: Artificial
<220> FEATURE:
<223> OTHER INFORMATION: Synthetic DNA

<400> SEQUENCE: 40
caagcagaag acggcatacg agattctaca cagtctcgtg ggctcggaga tgtgtataag    60
agacag                                                               66

<210> SEQ ID NO 41
<211> LENGTH: 66
<212> TYPE: DNA
<213> ORGANISM: Artificial
<220> FEATURE:
<223> OTHER INFORMATION: Synthetic DNA

<400> SEQUENCE: 41
caagcagaag acggcatacg agatgataga tcgtctcgtg ggctcggaga tgtgtataag    60
```

-continued agacag                                                              66

<210> SEQ ID NO 42
<211> LENGTH: 66
<212> TYPE: DNA
<213> ORGANISM: Artificial
<220> FEATURE:
<223> OTHER INFORMATION: Synthetic DNA

<400> SEQUENCE: 42
caagcagaag acggcatacg agatgagcgt acgtctcgtg ggctcggaga tgtgtataag    60
agacag                                                              66

<210> SEQ ID NO 43
<211> LENGTH: 66
<212> TYPE: DNA
<213> ORGANISM: Artificial
<220> FEATURE:
<223> OTHER INFORMATION: Synthetic DNA

<400> SEQUENCE: 43
caagcagaag acggcatacg agatcagaga cagtctcgtg ggctcggaga tgtgtataag    60
agacag                                                              66

<210> SEQ ID NO 44
<211> LENGTH: 66
<212> TYPE: DNA
<213> ORGANISM: Artificial
<220> FEATURE:
<223> OTHER INFORMATION: Synthetic DNA

<400> SEQUENCE: 44
caagcagaag acggcatacg agatcataga tggtctcgtg ggctcggaga tgtgtataag    60
agacag                                                              66

<210> SEQ ID NO 45
<211> LENGTH: 66
<212> TYPE: DNA
<213> ORGANISM: Artificial
<220> FEATURE:
<223> OTHER INFORMATION: Synthetic DNA

<400> SEQUENCE: 45
caagcagaag acggcatacg agatagatgc tagtctcgtg ggctcggaga tgtgtataag    60
agacag                                                              66

<210> SEQ ID NO 46
<211> LENGTH: 66
<212> TYPE: DNA
<213> ORGANISM: Artificial
<220> FEATURE:
<223> OTHER INFORMATION: Synthetic DNA

<400> SEQUENCE: 46
caagcagaag acggcatacg agatctcatc tcgtctcgtg ggctcggaga tgtgtataag    60
agacag                                                              66

<210> SEQ ID NO 47
<211> LENGTH: 66
<212> TYPE: DNA
<213> ORGANISM: Artificial
<220> FEATURE:

<223> OTHER INFORMATION: Synthetic DNA

<400> SEQUENCE: 47
caagcagaag acggcatacg agattatcta tggtctcgtg ggctcggaga tgtgtataag    60
agacag    66

<210> SEQ ID NO 48
<211> LENGTH: 66
<212> TYPE: DNA
<213> ORGANISM: Artificial
<220> FEATURE:
<223> OTHER INFORMATION: Synthetic DNA

<400> SEQUENCE: 48
caagcagaag acggcatacg agatagagta tcgtctcgtg ggctcggaga tgtgtataag    60
agacag    66

<210> SEQ ID NO 49
<211> LENGTH: 66
<212> TYPE: DNA
<213> ORGANISM: Artificial
<220> FEATURE:
<223> OTHER INFORMATION: Synthetic DNA

<400> SEQUENCE: 49
caagcagaag acggcatacg agatgtgact aggtctcgtg ggctcggaga tgtgtataag    60
agacag    66

<210> SEQ ID NO 50
<211> LENGTH: 66
<212> TYPE: DNA
<213> ORGANISM: Artificial
<220> FEATURE:
<223> OTHER INFORMATION: Synthetic DNA

<400> SEQUENCE: 50
caagcagaag acggcatacg agatctatgc tcgtctcgtg ggctcggaga tgtgtataag    60
agacag    66

<210> SEQ ID NO 51
<211> LENGTH: 66
<212> TYPE: DNA
<213> ORGANISM: Artificial
<220> FEATURE:
<223> OTHER INFORMATION: Synthetic DNA

<400> SEQUENCE: 51
caagcagaag acggcatacg agatctgact acgtctcgtg ggctcggaga tgtgtataag    60
agacag    66

<210> SEQ ID NO 52
<211> LENGTH: 66
<212> TYPE: DNA
<213> ORGANISM: Artificial
<220> FEATURE:
<223> OTHER INFORMATION: Synthetic DNA

<400> SEQUENCE: 52
caagcagaag acggcatacg agattatcag tagtctcgtg ggctcggaga tgtgtataag    60
agacag    66

```
<210> SEQ ID NO 53
<211> LENGTH: 66
<212> TYPE: DNA
<213> ORGANISM: Artificial
<220> FEATURE:
<223> OTHER INFORMATION: Synthetic DNA

<400> SEQUENCE: 53
caagcagaag acggcatacg agatgagtct gcgtctcgtg ggctcggaga tgtgtataag    60
agacag                                                              66

<210> SEQ ID NO 54
<211> LENGTH: 66
<212> TYPE: DNA
<213> ORGANISM: Artificial
<220> FEATURE:
<223> OTHER INFORMATION: Synthetic DNA

<400> SEQUENCE: 54
caagcagaag acggcatacg agatcagtcg cagtctcgtg ggctcggaga tgtgtataag    60
agacag                                                              66

<210> SEQ ID NO 55
<211> LENGTH: 66
<212> TYPE: DNA
<213> ORGANISM: Artificial
<220> FEATURE:
<223> OTHER INFORMATION: Synthetic DNA

<400> SEQUENCE: 55
caagcagaag acggcatacg agatgacatc tagtctcgtg ggctcggaga tgtgtataag    60
agacag                                                              66

<210> SEQ ID NO 56
<211> LENGTH: 66
<212> TYPE: DNA
<213> ORGANISM: Artificial
<220> FEATURE:
<223> OTHER INFORMATION: Synthetic DNA

<400> SEQUENCE: 56
caagcagaag acggcatacg agatctgtga cggtctcgtg ggctcggaga tgtgtataag    60
agacag                                                              66

<210> SEQ ID NO 57
<211> LENGTH: 66
<212> TYPE: DNA
<213> ORGANISM: Artificial
<220> FEATURE:
<223> OTHER INFORMATION: Synthetic DNA

<400> SEQUENCE: 57
caagcagaag acggcatacg agataagagg cagtctcgtg ggctcggaga tgtgtataag    60
agacag                                                              66

<210> SEQ ID NO 58
<211> LENGTH: 66
<212> TYPE: DNA
<213> ORGANISM: Artificial
<220> FEATURE:
<223> OTHER INFORMATION: Synthetic DNA

<400> SEQUENCE: 58
```

```
caagcagaag acggcatacg agatctagta cggtctcgtg ggctcggaga tgtgtataag    60
agacag                                                               66

<210> SEQ ID NO 59
<211> LENGTH: 66
<212> TYPE: DNA
<213> ORGANISM: Artificial
<220> FEATURE:
<223> OTHER INFORMATION: Synthetic DNA

<400> SEQUENCE: 59
caagcagaag acggcatacg agataggagt ccgtctcgtg ggctcggaga tgtgtataag    60
agacag                                                               66

<210> SEQ ID NO 60
<211> LENGTH: 66
<212> TYPE: DNA
<213> ORGANISM: Artificial
<220> FEATURE:
<223> OTHER INFORMATION: Synthetic DNA

<400> SEQUENCE: 60
caagcagaag acggcatacg agatcatgcc tagtctcgtg ggctcggaga tgtgtataag    60
agacag                                                               66

<210> SEQ ID NO 61
<211> LENGTH: 66
<212> TYPE: DNA
<213> ORGANISM: Artificial
<220> FEATURE:
<223> OTHER INFORMATION: Synthetic DNA

<400> SEQUENCE: 61
caagcagaag acggcatacg agatgtagag aggtctcgtg ggctcggaga tgtgtataag    60
agacag                                                               66

<210> SEQ ID NO 62
<211> LENGTH: 66
<212> TYPE: DNA
<213> ORGANISM: Artificial
<220> FEATURE:
<223> OTHER INFORMATION: Synthetic DNA

<400> SEQUENCE: 62
caagcagaag acggcatacg agatcctctc tggtctcgtg ggctcggaga tgtgtataag    60
agacag                                                               66

<210> SEQ ID NO 63
<211> LENGTH: 66
<212> TYPE: DNA
<213> ORGANISM: Artificial
<220> FEATURE:
<223> OTHER INFORMATION: Synthetic DNA

<400> SEQUENCE: 63
caagcagaag acggcatacg agatagcgta gcgtctcgtg ggctcggaga tgtgtataag    60
agacag                                                               66

<210> SEQ ID NO 64
<211> LENGTH: 66
<212> TYPE: DNA
<213> ORGANISM: Artificial
```

```
<220> FEATURE:
<223> OTHER INFORMATION: Synthetic DNA

<400> SEQUENCE: 64
caagcagaag acggcatacg agattcctct acgtctcgtg ggctcggaga tgtgtataag    60
agacag                                                              66

<210> SEQ ID NO 65
<211> LENGTH: 66
<212> TYPE: DNA
<213> ORGANISM: Artificial
<220> FEATURE:
<223> OTHER INFORMATION: Synthetic DNA

<400> SEQUENCE: 65
caagcagaag acggcatacg agatgacgta cagtctcgtg ggctcggaga tgtgtataag    60
agacag                                                              66

<210> SEQ ID NO 66
<211> LENGTH: 66
<212> TYPE: DNA
<213> ORGANISM: Artificial
<220> FEATURE:
<223> OTHER INFORMATION: Synthetic DNA

<400> SEQUENCE: 66
caagcagaag acggcatacg agatgactgt aggtctcgtg ggctcggaga tgtgtataag    60
agacag                                                              66

<210> SEQ ID NO 67
<211> LENGTH: 66
<212> TYPE: DNA
<213> ORGANISM: Artificial
<220> FEATURE:
<223> OTHER INFORMATION: Synthetic DNA

<400> SEQUENCE: 67
caagcagaag acggcatacg agattcagta cagtctcgtg ggctcggaga tgtgtataag    60
agacag                                                              66

<210> SEQ ID NO 68
<211> LENGTH: 66
<212> TYPE: DNA
<213> ORGANISM: Artificial
<220> FEATURE:
<223> OTHER INFORMATION: Synthetic DNA

<400> SEQUENCE: 68
caagcagaag acggcatacg agatcatgat aggtctcgtg ggctcggaga tgtgtataag    60
agacag                                                              66

<210> SEQ ID NO 69
<211> LENGTH: 66
<212> TYPE: DNA
<213> ORGANISM: Artificial
<220> FEATURE:
<223> OTHER INFORMATION: Synthetic DNA

<400> SEQUENCE: 69
caagcagaag acggcatacg agatgcatct cggtctcgtg ggctcggaga tgtgtataag    60
agacag                                                              66
```

<210> SEQ ID NO 70
<211> LENGTH: 66
<212> TYPE: DNA
<213> ORGANISM: Artificial
<220> FEATURE:
<223> OTHER INFORMATION: Synthetic DNA

<400> SEQUENCE: 70
caagcagaag acggcatacg agattgcaca gagtctcgtg ggctcggaga tgtgtataag    60
agacag    66

<210> SEQ ID NO 71
<211> LENGTH: 66
<212> TYPE: DNA
<213> ORGANISM: Artificial
<220> FEATURE:
<223> OTHER INFORMATION: Synthetic DNA

<400> SEQUENCE: 71
caagcagaag acggcatacg agatgagcta tagtctcgtg ggctcggaga tgtgtataag    60
agacag    66

<210> SEQ ID NO 72
<211> LENGTH: 66
<212> TYPE: DNA
<213> ORGANISM: Artificial
<220> FEATURE:
<223> OTHER INFORMATION: Synthetic DNA

<400> SEQUENCE: 72
caagcagaag acggcatacg agatagtctg cagtctcgtg ggctcggaga tgtgtataag    60
agacag    66

<210> SEQ ID NO 73
<211> LENGTH: 66
<212> TYPE: DNA
<213> ORGANISM: Artificial
<220> FEATURE:
<223> OTHER INFORMATION: Synthetic DNA

<400> SEQUENCE: 73
caagcagaag acggcatacg agatcgctgt gagtctcgtg ggctcggaga tgtgtataag    60
agacag    66

<210> SEQ ID NO 74
<211> LENGTH: 66
<212> TYPE: DNA
<213> ORGANISM: Artificial
<220> FEATURE:
<223> OTHER INFORMATION: Synthetic DNA

<400> SEQUENCE: 74
caagcagaag acggcatacg agatctgatg tggtctcgtg ggctcggaga tgtgtataag    60
agacag    66

<210> SEQ ID NO 75
<211> LENGTH: 66
<212> TYPE: DNA
<213> ORGANISM: Artificial
<220> FEATURE:
<223> OTHER INFORMATION: Synthetic DNA

<400> SEQUENCE: 75

```
caagcagaag acggcatacg agatgcactc tagtctcgtg ggctcggaga tgtgtataag    60
agacag                                                              66
```

<210> SEQ ID NO 76
<211> LENGTH: 66
<212> TYPE: DNA
<213> ORGANISM: Artificial
<220> FEATURE:
<223> OTHER INFORMATION: Synthetic DNA

<400> SEQUENCE: 76

```
caagcagaag acggcatacg agattctgct cagtctcgtg ggctcggaga tgtgtataag    60
agacag                                                              66
```

<210> SEQ ID NO 77
<211> LENGTH: 66
<212> TYPE: DNA
<213> ORGANISM: Artificial
<220> FEATURE:
<223> OTHER INFORMATION: Synthetic DNA

<400> SEQUENCE: 77

```
caagcagaag acggcatacg agattgtatc tagtctcgtg ggctcggaga tgtgtataag    60
agacag                                                              66
```

<210> SEQ ID NO 78
<211> LENGTH: 66
<212> TYPE: DNA
<213> ORGANISM: Artificial
<220> FEATURE:
<223> OTHER INFORMATION: Synthetic DNA

<400> SEQUENCE: 78

```
caagcagaag acggcatacg agatacagtg aggtctcgtg ggctcggaga tgtgtataag    60
agacag                                                              66
```

<210> SEQ ID NO 79
<211> LENGTH: 66
<212> TYPE: DNA
<213> ORGANISM: Artificial
<220> FEATURE:
<223> OTHER INFORMATION: Synthetic DNA

<400> SEQUENCE: 79

```
caagcagaag acggcatacg agatatgcga tagtctcgtg ggctcggaga tgtgtataag    60
agacag                                                              66
```

<210> SEQ ID NO 80
<211> LENGTH: 66
<212> TYPE: DNA
<213> ORGANISM: Artificial
<220> FEATURE:
<223> OTHER INFORMATION: Synthetic DNA

<400> SEQUENCE: 80

```
caagcagaag acggcatacg agatgagaca tggtctcgtg ggctcggaga tgtgtataag    60
agacag                                                              66
```

<210> SEQ ID NO 81
<211> LENGTH: 66
<212> TYPE: DNA

```
<213> ORGANISM: Artificial
<220> FEATURE:
<223> OTHER INFORMATION: Synthetic DNA

<400> SEQUENCE: 81
caagcagaag acggcatacg agatgtcatg tggtctcgtg ggctcggaga tgtgtataag    60
agacag                                                               66

<210> SEQ ID NO 82
<211> LENGTH: 66
<212> TYPE: DNA
<213> ORGANISM: Artificial
<220> FEATURE:
<223> OTHER INFORMATION: Synthetic DNA

<400> SEQUENCE: 82
caagcagaag acggcatacg agattcatga tagtctcgtg ggctcggaga tgtgtataag    60
agacag                                                               66

<210> SEQ ID NO 83
<211> LENGTH: 66
<212> TYPE: DNA
<213> ORGANISM: Artificial
<220> FEATURE:
<223> OTHER INFORMATION: Synthetic DNA

<400> SEQUENCE: 83
caagcagaag acggcatacg agatgtcatc tcgtctcgtg ggctcggaga tgtgtataag    60
agacag                                                               66

<210> SEQ ID NO 84
<211> LENGTH: 66
<212> TYPE: DNA
<213> ORGANISM: Artificial
<220> FEATURE:
<223> OTHER INFORMATION: Synthetic DNA

<400> SEQUENCE: 84
caagcagaag acggcatacg agattatctc tagtctcgtg ggctcggaga tgtgtataag    60
agacag                                                               66

<210> SEQ ID NO 85
<211> LENGTH: 66
<212> TYPE: DNA
<213> ORGANISM: Artificial
<220> FEATURE:
<223> OTHER INFORMATION: Synthetic DNA

<400> SEQUENCE: 85
caagcagaag acggcatacg agatctgata tagtctcgtg ggctcggaga tgtgtataag    60
agacag                                                               66

<210> SEQ ID NO 86
<211> LENGTH: 66
<212> TYPE: DNA
<213> ORGANISM: Artificial
<220> FEATURE:
<223> OTHER INFORMATION: Synthetic DNA

<400> SEQUENCE: 86
caagcagaag acggcatacg agattacgca tggtctcgtg ggctcggaga tgtgtataag    60
agacag                                                               66
```

<210> SEQ ID NO 87
<211> LENGTH: 66
<212> TYPE: DNA
<213> ORGANISM: Artificial
<220> FEATURE:
<223> OTHER INFORMATION: Synthetic DNA

<400> SEQUENCE: 87
caagcagaag acggcatacg agatcgtgag tggtctcgtg ggctcggaga tgtgtataag    60
agacag                                                              66

<210> SEQ ID NO 88
<211> LENGTH: 66
<212> TYPE: DNA
<213> ORGANISM: Artificial
<220> FEATURE:
<223> OTHER INFORMATION: Synthetic DNA

<400> SEQUENCE: 88
caagcagaag acggcatacg agatgacaca tggtctcgtg ggctcggaga tgtgtataag    60
agacag                                                              66

<210> SEQ ID NO 89
<211> LENGTH: 66
<212> TYPE: DNA
<213> ORGANISM: Artificial
<220> FEATURE:
<223> OTHER INFORMATION: Synthetic DNA

<400> SEQUENCE: 89
caagcagaag acggcatacg agatacatga cggtctcgtg ggctcggaga tgtgtataag    60
agacag                                                              66

<210> SEQ ID NO 90
<211> LENGTH: 66
<212> TYPE: DNA
<213> ORGANISM: Artificial
<220> FEATURE:
<223> OTHER INFORMATION: Synthetic DNA

<400> SEQUENCE: 90
caagcagaag acggcatacg agatgcgtct aggtctcgtg ggctcggaga tgtgtataag    60
agacag                                                              66

<210> SEQ ID NO 91
<211> LENGTH: 66
<212> TYPE: DNA
<213> ORGANISM: Artificial
<220> FEATURE:
<223> OTHER INFORMATION: Synthetic DNA

<400> SEQUENCE: 91
caagcagaag acggcatacg agattcacgc tggtctcgtg ggctcggaga tgtgtataag    60
agacag                                                              66

<210> SEQ ID NO 92
<211> LENGTH: 66
<212> TYPE: DNA
<213> ORGANISM: Artificial
<220> FEATURE:
<223> OTHER INFORMATION: Synthetic DNA

```
<400> SEQUENCE: 92
caagcagaag acggcatacg agattcatgt acgtctcgtg ggctcggaga tgtgtataag      60
agacag                                                                 66

<210> SEQ ID NO 93
<211> LENGTH: 66
<212> TYPE: DNA
<213> ORGANISM: Artificial
<220> FEATURE:
<223> OTHER INFORMATION: Synthetic DNA

<400> SEQUENCE: 93
caagcagaag acggcatacg agattagtga cggtctcgtg ggctcggaga tgtgtataag      60
agacag                                                                 66

<210> SEQ ID NO 94
<211> LENGTH: 66
<212> TYPE: DNA
<213> ORGANISM: Artificial
<220> FEATURE:
<223> OTHER INFORMATION: Synthetic DNA

<400> SEQUENCE: 94
caagcagaag acggcatacg agatcacgat aggtctcgtg ggctcggaga tgtgtataag      60
agacag                                                                 66

<210> SEQ ID NO 95
<211> LENGTH: 66
<212> TYPE: DNA
<213> ORGANISM: Artificial
<220> FEATURE:
<223> OTHER INFORMATION: Synthetic DNA

<400> SEQUENCE: 95
caagcagaag acggcatacg agatacacac tggtctcgtg ggctcggaga tgtgtataag      60
agacag                                                                 66

<210> SEQ ID NO 96
<211> LENGTH: 66
<212> TYPE: DNA
<213> ORGANISM: Artificial
<220> FEATURE:
<223> OTHER INFORMATION: Synthetic DNA

<400> SEQUENCE: 96
caagcagaag acggcatacg agatagcatc acgtctcgtg ggctcggaga tgtgtataag      60
agacag                                                                 66

<210> SEQ ID NO 97
<211> LENGTH: 66
<212> TYPE: DNA
<213> ORGANISM: Artificial
<220> FEATURE:
<223> OTHER INFORMATION: Synthetic DNA

<400> SEQUENCE: 97
caagcagaag acggcatacg agattagtcg tagtctcgtg ggctcggaga tgtgtataag      60
agacag                                                                 66

<210> SEQ ID NO 98
<211> LENGTH: 66
```

```
<212> TYPE: DNA
<213> ORGANISM: Artificial
<220> FEATURE:
<223> OTHER INFORMATION: Synthetic DNA

<400> SEQUENCE: 98
caagcagaag acggcatacg agatgcatcg cggtctcgtg ggctcggaga tgtgtataag    60
agacag                                                               66

<210> SEQ ID NO 99
<211> LENGTH: 66
<212> TYPE: DNA
<213> ORGANISM: Artificial
<220> FEATURE:
<223> OTHER INFORMATION: Synthetic DNA

<400> SEQUENCE: 99
caagcagaag acggcatacg agatatcatg tcgtctcgtg ggctcggaga tgtgtataag    60
agacag                                                               66

<210> SEQ ID NO 100
<211> LENGTH: 66
<212> TYPE: DNA
<213> ORGANISM: Artificial
<220> FEATURE:
<223> OTHER INFORMATION: Synthetic DNA

<400> SEQUENCE: 100
caagcagaag acggcatacg agatgtactc tagtctcgtg ggctcggaga tgtgtataag    60
agacag                                                               66

<210> SEQ ID NO 101
<211> LENGTH: 66
<212> TYPE: DNA
<213> ORGANISM: Artificial
<220> FEATURE:
<223> OTHER INFORMATION: Synthetic DNA

<400> SEQUENCE: 101
caagcagaag acggcatacg agatagtgca tagtctcgtg ggctcggaga tgtgtataag    60
agacag                                                               66

<210> SEQ ID NO 102
<211> LENGTH: 66
<212> TYPE: DNA
<213> ORGANISM: Artificial
<220> FEATURE:
<223> OTHER INFORMATION: Synthetic DNA

<400> SEQUENCE: 102
caagcagaag acggcatacg agatcgcatc aggtctcgtg ggctcggaga tgtgtataag    60
agacag                                                               66

<210> SEQ ID NO 103
<211> LENGTH: 66
<212> TYPE: DNA
<213> ORGANISM: Artificial
<220> FEATURE:
<223> OTHER INFORMATION: Synthetic DNA

<400> SEQUENCE: 103
caagcagaag acggcatacg agatcgctat aggtctcgtg ggctcggaga tgtgtataag    60
``` agacag 66

<210> SEQ ID NO 104
<211> LENGTH: 66
<212> TYPE: DNA
<213> ORGANISM: Artificial
<220> FEATURE:
<223> OTHER INFORMATION: Synthetic DNA

<400> SEQUENCE: 104
caagcagaag acggcatacg agattagctc tagtctcgtg ggctcggaga tgtgtataag    60
agacag    66

<210> SEQ ID NO 105
<211> LENGTH: 66
<212> TYPE: DNA
<213> ORGANISM: Artificial
<220> FEATURE:
<223> OTHER INFORMATION: Synthetic DNA

<400> SEQUENCE: 105
caagcagaag acggcatacg agatgtcgat aggtctcgtg ggctcggaga tgtgtataag    60
agacag    66

<210> SEQ ID NO 106
<211> LENGTH: 66
<212> TYPE: DNA
<213> ORGANISM: Artificial
<220> FEATURE:
<223> OTHER INFORMATION: Synthetic DNA

<400> SEQUENCE: 106
caagcagaag acggcatacg agatagctcg tagtctcgtg ggctcggaga tgtgtataag    60
agacag    66

<210> SEQ ID NO 107
<211> LENGTH: 66
<212> TYPE: DNA
<213> ORGANISM: Artificial
<220> FEATURE:
<223> OTHER INFORMATION: Synthetic DNA

<400> SEQUENCE: 107
caagcagaag acggcatacg agatacacag tagtctcgtg ggctcggaga tgtgtataag    60
agacag    66

<210> SEQ ID NO 108
<211> LENGTH: 66
<212> TYPE: DNA
<213> ORGANISM: Artificial
<220> FEATURE:
<223> OTHER INFORMATION: Synthetic DNA

<400> SEQUENCE: 108
caagcagaag acggcatacg agatcagatg tagtctcgtg ggctcggaga tgtgtataag    60
agacag    66

<210> SEQ ID NO 109
<211> LENGTH: 66
<212> TYPE: DNA
<213> ORGANISM: Artificial
<220> FEATURE:
<223> OTHER INFORMATION: Synthetic DNA

<400> SEQUENCE: 109
caagcagaag acggcatacg agatctctac aggtctcgtg ggctcggaga tgtgtataag    60
agacag                                                                66

<210> SEQ ID NO 110
<211> LENGTH: 66
<212> TYPE: DNA
<213> ORGANISM: Artificial
<220> FEATURE:
<223> OTHER INFORMATION: Synthetic DNA

<400> SEQUENCE: 110
caagcagaag acggcatacg agatgtcact aggtctcgtg ggctcggaga tgtgtataag    60
agacag                                                                66

<210> SEQ ID NO 111
<211> LENGTH: 66
<212> TYPE: DNA
<213> ORGANISM: Artificial
<220> FEATURE:
<223> OTHER INFORMATION: Synthetic DNA

<400> SEQUENCE: 111
caagcagaag acggcatacg agattgtact aggtctcgtg ggctcggaga tgtgtataag    60
agacag                                                                66

<210> SEQ ID NO 112
<211> LENGTH: 66
<212> TYPE: DNA
<213> ORGANISM: Artificial
<220> FEATURE:
<223> OTHER INFORMATION: Synthetic DNA

<400> SEQUENCE: 112
caagcagaag acggcatacg agatacgcta tggtctcgtg ggctcggaga tgtgtataag    60
agacag                                                                66

<210> SEQ ID NO 113
<211> LENGTH: 66
<212> TYPE: DNA
<213> ORGANISM: Artificial
<220> FEATURE:
<223> OTHER INFORMATION: Synthetic DNA

<400> SEQUENCE: 113
caagcagaag acggcatacg agatatgtat aggtctcgtg ggctcggaga tgtgtataag    60
agacag                                                                66

<210> SEQ ID NO 114
<211> LENGTH: 66
<212> TYPE: DNA
<213> ORGANISM: Artificial
<220> FEATURE:
<223> OTHER INFORMATION: Synthetic DNA

<400> SEQUENCE: 114
caagcagaag acggcatacg agattgtgac aggtctcgtg ggctcggaga tgtgtataag    60
agacag                                                                66

<210> SEQ ID NO 115

```
<211> LENGTH: 66
<212> TYPE: DNA
<213> ORGANISM: Artificial
<220> FEATURE:
<223> OTHER INFORMATION: Synthetic DNA

<400> SEQUENCE: 115
caagcagaag acggcatacg agatgacgtc aggtctcgtg ggctcggaga tgtgtataag      60
agacag                                                                66

<210> SEQ ID NO 116
<211> LENGTH: 66
<212> TYPE: DNA
<213> ORGANISM: Artificial
<220> FEATURE:
<223> OTHER INFORMATION: Synthetic DNA

<400> SEQUENCE: 116
caagcagaag acggcatacg agatagatcg aggtctcgtg ggctcggaga tgtgtataag      60
agacag                                                                66

<210> SEQ ID NO 117
<211> LENGTH: 66
<212> TYPE: DNA
<213> ORGANISM: Artificial
<220> FEATURE:
<223> OTHER INFORMATION: Synthetic DNA

<400> SEQUENCE: 117
caagcagaag acggcatacg agatatagta gagtctcgtg ggctcggaga tgtgtataag      60
agacag                                                                66

<210> SEQ ID NO 118
<211> LENGTH: 66
<212> TYPE: DNA
<213> ORGANISM: Artificial
<220> FEATURE:
<223> OTHER INFORMATION: Synthetic DNA

<400> SEQUENCE: 118
caagcagaag acggcatacg agattatgac tagtctcgtg ggctcggaga tgtgtataag      60
agacag                                                                66

<210> SEQ ID NO 119
<211> LENGTH: 66
<212> TYPE: DNA
<213> ORGANISM: Artificial
<220> FEATURE:
<223> OTHER INFORMATION: Synthetic DNA

<400> SEQUENCE: 119
caagcagaag acggcatacg agattagaga tggtctcgtg ggctcggaga tgtgtataag      60
agacag                                                                66

<210> SEQ ID NO 120
<211> LENGTH: 66
<212> TYPE: DNA
<213> ORGANISM: Artificial
<220> FEATURE:
<223> OTHER INFORMATION: Synthetic DNA

<400> SEQUENCE: 120
caagcagaag acggcatacg agatagctga gagtctcgtg ggctcggaga tgtgtataag      60
``` agacag 66

<210> SEQ ID NO 121
<211> LENGTH: 66
<212> TYPE: DNA
<213> ORGANISM: Artificial
<220> FEATURE:
<223> OTHER INFORMATION: Synthetic DNA

<400> SEQUENCE: 121
caagcagaag acggcatacg agatacatct gagtctcgtg ggctcggaga tgtgtataag    60
agacag                                                               66

<210> SEQ ID NO 122
<211> LENGTH: 66
<212> TYPE: DNA
<213> ORGANISM: Artificial
<220> FEATURE:
<223> OTHER INFORMATION: Synthetic DNA

<400> SEQUENCE: 122
caagcagaag acggcatacg agatgcgtgc tagtctcgtg ggctcggaga tgtgtataag    60
agacag                                                               66

<210> SEQ ID NO 123
<211> LENGTH: 66
<212> TYPE: DNA
<213> ORGANISM: Artificial
<220> FEATURE:
<223> OTHER INFORMATION: Synthetic DNA

<400> SEQUENCE: 123
caagcagaag acggcatacg agatacatgt aggtctcgtg ggctcggaga tgtgtataag    60
agacag                                                               66

<210> SEQ ID NO 124
<211> LENGTH: 66
<212> TYPE: DNA
<213> ORGANISM: Artificial
<220> FEATURE:
<223> OTHER INFORMATION: Synthetic DNA

<400> SEQUENCE: 124
caagcagaag acggcatacg agatatagag aggtctcgtg ggctcggaga tgtgtataag    60
agacag                                                               66

<210> SEQ ID NO 125
<211> LENGTH: 66
<212> TYPE: DNA
<213> ORGANISM: Artificial
<220> FEATURE:
<223> OTHER INFORMATION: Synthetic DNA

<400> SEQUENCE: 125
caagcagaag acggcatacg agatgtatct aggtctcgtg ggctcggaga tgtgtataag    60
agacag                                                               66

<210> SEQ ID NO 126
<211> LENGTH: 66
<212> TYPE: DNA
<213> ORGANISM: Artificial
<220> FEATURE:

<223> OTHER INFORMATION: Synthetic DNA

<400> SEQUENCE: 126
caagcagaag acggcatacg agatatactg tagtctcgtg ggctcggaga tgtgtataag    60
agacag    66

<210> SEQ ID NO 127
<211> LENGTH: 66
<212> TYPE: DNA
<213> ORGANISM: Artificial
<220> FEATURE:
<223> OTHER INFORMATION: Synthetic DNA

<400> SEQUENCE: 127
caagcagaag acggcatacg agatgcacat aggtctcgtg ggctcggaga tgtgtataag    60
agacag    66

<210> SEQ ID NO 128
<211> LENGTH: 66
<212> TYPE: DNA
<213> ORGANISM: Artificial
<220> FEATURE:
<223> OTHER INFORMATION: Synthetic DNA

<400> SEQUENCE: 128
caagcagaag acggcatacg agatatgatg aggtctcgtg ggctcggaga tgtgtataag    60
agacag    66

<210> SEQ ID NO 129
<211> LENGTH: 66
<212> TYPE: DNA
<213> ORGANISM: Artificial
<220> FEATURE:
<223> OTHER INFORMATION: Synthetic DNA

<400> SEQUENCE: 129
caagcagaag acggcatacg agatagtagt aggtctcgtg ggctcggaga tgtgtataag    60
agacag    66

<210> SEQ ID NO 130
<211> LENGTH: 66
<212> TYPE: DNA
<213> ORGANISM: Artificial
<220> FEATURE:
<223> OTHER INFORMATION: Synthetic DNA

<400> SEQUENCE: 130
caagcagaag acggcatacg agattatgtc aggtctcgtg ggctcggaga tgtgtataag    60
agacag    66

<210> SEQ ID NO 131
<211> LENGTH: 66
<212> TYPE: DNA
<213> ORGANISM: Artificial
<220> FEATURE:
<223> OTHER INFORMATION: Synthetic DNA

<400> SEQUENCE: 131
caagcagaag acggcatacg agatgtgtgt gagtctcgtg ggctcggaga tgtgtataag    60
agacag    66

```
<210> SEQ ID NO 132
<211> LENGTH: 66
<212> TYPE: DNA
<213> ORGANISM: Artificial
<220> FEATURE:
<223> OTHER INFORMATION: Synthetic DNA

<400> SEQUENCE: 132
caagcagaag acggcatacg agattacgac aggtctcgtg ggctcggaga tgtgtataag    60
agacag                                                              66

<210> SEQ ID NO 133
<211> LENGTH: 66
<212> TYPE: DNA
<213> ORGANISM: Artificial
<220> FEATURE:
<223> OTHER INFORMATION: Synthetic DNA

<400> SEQUENCE: 133
caagcagaag acggcatacg agatatgtga tggtctcgtg ggctcggaga tgtgtataag    60
agacag                                                              66

<210> SEQ ID NO 134
<211> LENGTH: 70
<212> TYPE: DNA
<213> ORGANISM: Artificial
<220> FEATURE:
<223> OTHER INFORMATION: Synthetic DNA

<400> SEQUENCE: 134
aatgatacgg cgaccaccga gatctacacc gcgcagatcg tcggcagcgt cagatgtgta    60
taagagacag                                                          70

<210> SEQ ID NO 135
<211> LENGTH: 162
<212> TYPE: DNA
<213> ORGANISM: Saccharum spontaneum

<400> SEQUENCE: 135
cagaacgtgg tcgccgtcgc catgctcctt cgtaacatgc ctgagccatc gaatcctgac    60
actcgtcaag cccgagatga aatccgagga ctcatcgaga ccgctgctat gcagcaaacc   120
gagagttctg ccttgaggtg acgcgggcct acctcggagc ag                     162

<210> SEQ ID NO 136
<211> LENGTH: 128
<212> TYPE: DNA
<213> ORGANISM: Saccharum spontaneum

<400> SEQUENCE: 136
ctctggcgaa cgcggtgagg agcacaccca tggtctgccc cggcgagatg accagcgtgg    60
tggccgctgt agacccccac acgccgccct gcactctgcc tccttccgag gagttcgacc   120
tcttcggc                                                           128

<210> SEQ ID NO 137
<211> LENGTH: 216
<212> TYPE: DNA
<213> ORGANISM: Saccharum spontaneum

<400> SEQUENCE: 137
gagcacttga tgtcacctaa tatactggtt ctgagccatt acccgtttgg ggtccaatta    60
```

```
atttatgaaa tgacttgttg tcaattaccc tgagtttttg tccactctga agctgaactg    120
aacattgtgt gctccggtag ctgaaaatcc taccottagc actcagactg agtccattgt    180
tcttatcata gccttatggt tgttcatttt gtatgc                              216
```

<210> SEQ ID NO 138
<211> LENGTH: 238
<212> TYPE: DNA
<213> ORGANISM: Saccharum spontaneum

<400> SEQUENCE: 138

```
ctcgagcggt gtccgacagg aacaggggga gttgtcgtat gatgacccgg tcgtcagtgg    60
ccccacccaa ctgacaagcc aagtggaagt cagcgagcca agtttgggt ttggtttcgc     120 cgttatactt ggtaagagtc gtgggggggc ggaaccgagc cgggagtaac atttcatgaa    180
tggccttgct aaagacccga ggtcccggtg gctcgggtga agggctttga tcctccga     238
```

<210> SEQ ID NO 139
<211> LENGTH: 212
<212> TYPE: DNA
<213> ORGANISM: Saccharum spontaneum

<400> SEQUENCE: 139

```
cagtaagctc catcgaggga caagcatcta gtgagtcaat accaaagtgg cgtggggcat    60
aaccatacag agcctgaaat ggggaacgat ccagagtgga atgccaactt gaattgtacc    120
aaaactcggc aagatggatc caattatgcc acttgtgggg taccgcattg acaaaacagc    180
gtaagaaggt ctccatgcac tggttgacgc gc                                  212
```

<210> SEQ ID NO 140
<211> LENGTH: 239
<212> TYPE: DNA
<213> ORGANISM: Saccharum spontaneum

<400> SEQUENCE: 140

```
acagtgaaca gtggtactat atacagtacc cgctacagca acacacgtcg tggtctcctt    60
aggcagcaga aatggtataa aaaaacgtac ataaaggtac atggcagata ggagtatatt    120
ctataaggag cacgtaacgc gtgacgggtc acgcgttcca gcgtcgtcta cctcgtgaca    180
ggcctcctcc cttgccccct ctccctccc cgtgcccctc ctcctctgcc ccctccctc     239
```

<210> SEQ ID NO 141
<211> LENGTH: 124
<212> TYPE: DNA
<213> ORGANISM: Saccharum spontaneum

<400> SEQUENCE: 141

```
caaaacaggg acaatatata tcctttgtct gcttaatcaa agcatgcctt ttagctgctt    60
gaataaaacc attcacatct tgtatgtaga aagcttcata tcttcgtttc gtgtacatcc    120
atga                                                                 124
```

<210> SEQ ID NO 142
<211> LENGTH: 197
<212> TYPE: DNA
<213> ORGANISM: Saccharum spontaneum

<400> SEQUENCE: 142

```
gccaccggcc tcgtggtcgt gagaccgagg agaccggtac ctggggatgg gctggtagtc    60
ctcatcagtg ctgtctgaag tgacatcctc aggtatatca gcagtctgag tctcaaggtc    120
```

```
cgcgagctct gcctcggcaa gctcgtcaac tctggcgtcc tgctcagctg ctgtctcagg    180
aacatctggg cgctcac                                                   197

<210> SEQ ID NO 143
<211> LENGTH: 140
<212> TYPE: DNA
<213> ORGANISM: Saccharum spontaneum

<400> SEQUENCE: 143
cagaggccct tgaaagcaca gctggttttc atcgtcaccc agtgaagaat gacatttcga    60
ggaaggcttt aggctacttg aatcccacga acatttctac agtaatattg gtaatatgcg   120
cagagggtcc ttggctactc                                                140

<210> SEQ ID NO 144
<211> LENGTH: 100
<212> TYPE: DNA
<213> ORGANISM: Saccharum spontaneum

<400> SEQUENCE: 144
gatcccggag gaagttcagg accggccaga gcagccagag gtaccaaccg gcgacgaagc    60
tcctgccgaa gatctacccg agtgtcctga ccaccggccc                          100

<210> SEQ ID NO 145
<211> LENGTH: 100
<212> TYPE: DNA
<213> ORGANISM: Saccharum spontaneum

<400> SEQUENCE: 145
tacaatgcag caagtgtttt catataactc ctagaactta atgcaataaa caattaaaag    60
tactcaagat agatttataa aaatgatggg ttcagcatgc                          100

<210> SEQ ID NO 146
<211> LENGTH: 175
<212> TYPE: DNA
<213> ORGANISM: Saccharum spontaneum

<400> SEQUENCE: 146
gcggaaaata gaccaatgta ttaggctatc cattgccgat atgcaaaaga atgaatccat    60
aatgatagcc gccgctcact tctggtcaga caccacaaat acctttatgt ttggtcatgg   120
tccatccgcc cctactcttg ccgatgtata catgctcacc gacttagata tctca         175

<210> SEQ ID NO 147
<211> LENGTH: 81
<212> TYPE: DNA
<213> ORGANISM: Saccharum spontaneum

<400> SEQUENCE: 147
caggaacttg caaacaagct cgggtgcaca gatccaaatc atttggtcgg ttgatgtgga    60
ctccgatgtg gactcaaatg c                                              81

<210> SEQ ID NO 148
<211> LENGTH: 136
<212> TYPE: DNA
<213> ORGANISM: Saccharum spontaneum

<400> SEQUENCE: 148
gcgtggcaga ggatgggggc acgacaggga tggcaccgtg gcgaggggag gagcacggtg    60
```

```
tggcagggaa aggagcgcgg cgagcttgac gccggggggcg caaccaggat gaggattgag    120
tcacggatgg ttggac                                                    136

<210> SEQ ID NO 149
<211> LENGTH: 135
<212> TYPE: DNA
<213> ORGANISM: Saccharum spontaneum

<400> SEQUENCE: 149
gaaaacaagc tctaccactg gcacaaacacg ggctcacagg tcacagctct gcttgctcag    60
tggtactacg agtgctagca cgggagcgct gttggacgga tcgccagcat gaaatgccca    120
ccgcgcacgt actgc                                                     135

<210> SEQ ID NO 150
<211> LENGTH: 143
<212> TYPE: DNA
<213> ORGANISM: Saccharum spontaneum

<400> SEQUENCE: 150
taccccacca aaaagcctat catgatcctt ggtgtcattt tattttttggt tctgtcaggt    60 aagtctagct gagtaccttc tcatactcag ggctttgttc ccacttgtta cagatggaca    120
gatgtactat ggttattgta tca                                            143

<210> SEQ ID NO 151
<211> LENGTH: 146
<212> TYPE: DNA
<213> ORGANISM: Saccharum spontaneum

<400> SEQUENCE: 151
taacccacca aagatagcct tgcatgctcc ttagtgtcgc ttattttggt ttaagacggg    60
taagtctagc tgagtacctt ctcgtactca gggcgttgtt ctcattgttg ttgcagatgg    120
ttagatgtac tatggatatt gcgtca                                         146

<210> SEQ ID NO 152
<211> LENGTH: 66
<212> TYPE: DNA
<213> ORGANISM: Artificial
<220> FEATURE:
<223> OTHER INFORMATION: Synthetic DNA

<400> SEQUENCE: 152
caagcagaag acggcatacg agattcgtca gagtctcgtg ggctcggaga tgtgtataag    60
agacag                                                               66

<210> SEQ ID NO 153
<211> LENGTH: 66
<212> TYPE: DNA
<213> ORGANISM: Artificial
<220> FEATURE:
<223> OTHER INFORMATION: Synthetic DNA

<400> SEQUENCE: 153
caagcagaag acggcatacg agatcgctag cggtctcgtg ggctcggaga tgtgtataag    60
agacag                                                               66

<210> SEQ ID NO 154
<211> LENGTH: 66
<212> TYPE: DNA
<213> ORGANISM: Artificial
```

```
<220> FEATURE:
<223> OTHER INFORMATION: Synthetic DNA

<400> SEQUENCE: 154
caagcagaag acggcatacg agattctcag tagtctcgtg ggctcggaga tgtgtataag      60
agacag                                                                 66

<210> SEQ ID NO 155
<211> LENGTH: 66
<212> TYPE: DNA
<213> ORGANISM: Artificial
<220> FEATURE:
<223> OTHER INFORMATION: Synthetic DNA

<400> SEQUENCE: 155
caagcagaag acggcatacg agatcgtaga tagtctcgtg ggctcggaga tgtgtataag      60
agacag                                                                 66

<210> SEQ ID NO 156
<211> LENGTH: 66
<212> TYPE: DNA
<213> ORGANISM: Artificial
<220> FEATURE:
<223> OTHER INFORMATION: Synthetic DNA

<400> SEQUENCE: 156
caagcagaag acggcatacg agatatacgt gagtctcgtg ggctcggaga tgtgtataag      60
agacag                                                                 66

<210> SEQ ID NO 157
<211> LENGTH: 66
<212> TYPE: DNA
<213> ORGANISM: Artificial
<220> FEATURE:
<223> OTHER INFORMATION: Synthetic DNA

<400> SEQUENCE: 157
caagcagaag acggcatacg agatgtctag aggtctcgtg ggctcggaga tgtgtataag      60
agacag                                                                 66

<210> SEQ ID NO 158
<211> LENGTH: 66
<212> TYPE: DNA
<213> ORGANISM: Artificial
<220> FEATURE:
<223> OTHER INFORMATION: Synthetic DNA

<400> SEQUENCE: 158
caagcagaag acggcatacg agatagtcga cagtctcgtg ggctcggaga tgtgtataag      60
agacag                                                                 66

<210> SEQ ID NO 159
<211> LENGTH: 66
<212> TYPE: DNA
<213> ORGANISM: Artificial
<220> FEATURE:
<223> OTHER INFORMATION: Synthetic DNA

<400> SEQUENCE: 159
caagcagaag acggcatacg agatagcgac gcgtctcgtg ggctcggaga tgtgtataag      60
agacag                                                                 66
```

<210> SEQ ID NO 160
<211> LENGTH: 66
<212> TYPE: DNA
<213> ORGANISM: Artificial
<220> FEATURE:
<223> OTHER INFORMATION: Synthetic DNA

<400> SEQUENCE: 160
caagcagaag acggcatacg agattgatag aggtctcgtg ggctcggaga tgtgtataag    60
agacag                                                              66

<210> SEQ ID NO 161
<211> LENGTH: 66
<212> TYPE: DNA
<213> ORGANISM: Artificial
<220> FEATURE:
<223> OTHER INFORMATION: Synthetic DNA

<400> SEQUENCE: 161
caagcagaag acggcatacg agatgacgac tggtctcgtg ggctcggaga tgtgtataag    60
agacag                                                              66

<210> SEQ ID NO 162
<211> LENGTH: 66
<212> TYPE: DNA
<213> ORGANISM: Artificial
<220> FEATURE:
<223> OTHER INFORMATION: Synthetic DNA

<400> SEQUENCE: 162
caagcagaag acggcatacg agattgtgct cagtctcgtg ggctcggaga tgtgtataag    60
agacag                                                              66

<210> SEQ ID NO 163
<211> LENGTH: 66
<212> TYPE: DNA
<213> ORGANISM: Artificial
<220> FEATURE:
<223> OTHER INFORMATION: Synthetic DNA

<400> SEQUENCE: 163
caagcagaag acggcatacg agatatgagc tggtctcgtg ggctcggaga tgtgtataag    60
agacag                                                              66

<210> SEQ ID NO 164
<211> LENGTH: 66
<212> TYPE: DNA
<213> ORGANISM: Artificial
<220> FEATURE:
<223> OTHER INFORMATION: Synthetic DNA

<400> SEQUENCE: 164
caagcagaag acggcatacg agattctctc acgtctcgtg ggctcggaga tgtgtataag    60
agacag                                                              66

<210> SEQ ID NO 165
<211> LENGTH: 66
<212> TYPE: DNA
<213> ORGANISM: Artificial
<220> FEATURE:
<223> OTHER INFORMATION: Synthetic DNA

<400> SEQUENCE: 165

```
caagcagaag acggcatacg agatgcagat cagtctcgtg ggctcggaga tgtgtataag    60
agacag                                                               66

<210> SEQ ID NO 166
<211> LENGTH: 66
<212> TYPE: DNA
<213> ORGANISM: Artificial
<220> FEATURE:
<223> OTHER INFORMATION: Synthetic DNA

<400> SEQUENCE: 166
caagcagaag acggcatacg agattctgca gagtctcgtg ggctcggaga tgtgtataag    60
agacag                                                               66

<210> SEQ ID NO 167
<211> LENGTH: 66
<212> TYPE: DNA
<213> ORGANISM: Artificial
<220> FEATURE:
<223> OTHER INFORMATION: Synthetic DNA

<400> SEQUENCE: 167
caagcagaag acggcatacg agatacgtga gcgtctcgtg ggctcggaga tgtgtataag    60
agacag                                                               66

<210> SEQ ID NO 168
<211> LENGTH: 66
<212> TYPE: DNA
<213> ORGANISM: Artificial
<220> FEATURE:
<223> OTHER INFORMATION: Synthetic DNA

<400> SEQUENCE: 168
caagcagaag acggcatacg agatcgcgtg aggtctcgtg ggctcggaga tgtgtataag    60
agacag                                                               66

<210> SEQ ID NO 169
<211> LENGTH: 66
<212> TYPE: DNA
<213> ORGANISM: Artificial
<220> FEATURE:
<223> OTHER INFORMATION: Synthetic DNA

<400> SEQUENCE: 169
caagcagaag acggcatacg agatcatact acgtctcgtg ggctcggaga tgtgtataag    60
agacag                                                               66

<210> SEQ ID NO 170
<211> LENGTH: 66
<212> TYPE: DNA
<213> ORGANISM: Artificial
<220> FEATURE:
<223> OTHER INFORMATION: Synthetic DNA

<400> SEQUENCE: 170
caagcagaag acggcatacg agattctaca cagtctcgtg ggctcggaga tgtgtataag    60
agacag                                                               66

<210> SEQ ID NO 171
<211> LENGTH: 66
<212> TYPE: DNA
```

```
<213> ORGANISM: Artificial
<220> FEATURE:
<223> OTHER INFORMATION: Synthetic DNA

<400> SEQUENCE: 171
caagcagaag acggcatacg agatgataga tcgtctcgtg ggctcggaga tgtgtataag    60
agacag                                                               66

<210> SEQ ID NO 172
<211> LENGTH: 66
<212> TYPE: DNA
<213> ORGANISM: Artificial
<220> FEATURE:
<223> OTHER INFORMATION: Synthetic DNA

<400> SEQUENCE: 172
caagcagaag acggcatacg agatgagcgt acgtctcgtg ggctcggaga tgtgtataag    60
agacag                                                               66

<210> SEQ ID NO 173
<211> LENGTH: 66
<212> TYPE: DNA
<213> ORGANISM: Artificial
<220> FEATURE:
<223> OTHER INFORMATION: Synthetic DNA

<400> SEQUENCE: 173
caagcagaag acggcatacg agatcagaga cagtctcgtg ggctcggaga tgtgtataag    60
agacag                                                               66

<210> SEQ ID NO 174
<211> LENGTH: 66
<212> TYPE: DNA
<213> ORGANISM: Artificial
<220> FEATURE:
<223> OTHER INFORMATION: Synthetic DNA

<400> SEQUENCE: 174
caagcagaag acggcatacg agatcataga tggtctcgtg ggctcggaga tgtgtataag    60
agacag                                                               66

<210> SEQ ID NO 175
<211> LENGTH: 66
<212> TYPE: DNA
<213> ORGANISM: Artificial
<220> FEATURE:
<223> OTHER INFORMATION: Synthetic DNA

<400> SEQUENCE: 175
caagcagaag acggcatacg agatagatgc tagtctcgtg ggctcggaga tgtgtataag    60
agacag                                                               66

<210> SEQ ID NO 176
<211> LENGTH: 66
<212> TYPE: DNA
<213> ORGANISM: Artificial
<220> FEATURE:
<223> OTHER INFORMATION: Synthetic DNA

<400> SEQUENCE: 176
caagcagaag acggcatacg agatctcatc tcgtctcgtg ggctcggaga tgtgtataag    60
agacag                                                               66
```

<210> SEQ ID NO 177
<211> LENGTH: 66
<212> TYPE: DNA
<213> ORGANISM: Artificial
<220> FEATURE:
<223> OTHER INFORMATION: Synthetic DNA

<400> SEQUENCE: 177
caagcagaag acggcatacg agattatcta tggtctcgtg ggctcggaga tgtgtataag    60
agacag                                                              66

<210> SEQ ID NO 178
<211> LENGTH: 66
<212> TYPE: DNA
<213> ORGANISM: Artificial
<220> FEATURE:
<223> OTHER INFORMATION: Synthetic DNA

<400> SEQUENCE: 178
caagcagaag acggcatacg agatagagta tcgtctcgtg ggctcggaga tgtgtataag    60
agacag                                                              66

<210> SEQ ID NO 179
<211> LENGTH: 66
<212> TYPE: DNA
<213> ORGANISM: Artificial
<220> FEATURE:
<223> OTHER INFORMATION: Synthetic DNA

<400> SEQUENCE: 179
caagcagaag acggcatacg agatgtgact aggtctcgtg ggctcggaga tgtgtataag    60
agacag                                                              66

<210> SEQ ID NO 180
<211> LENGTH: 66
<212> TYPE: DNA
<213> ORGANISM: Artificial
<220> FEATURE:
<223> OTHER INFORMATION: Synthetic DNA

<400> SEQUENCE: 180
caagcagaag acggcatacg agatctatgc tcgtctcgtg ggctcggaga tgtgtataag    60
agacag                                                              66

<210> SEQ ID NO 181
<211> LENGTH: 66
<212> TYPE: DNA
<213> ORGANISM: Artificial
<220> FEATURE:
<223> OTHER INFORMATION: Synthetic DNA

<400> SEQUENCE: 181
caagcagaag acggcatacg agatctgact acgtctcgtg ggctcggaga tgtgtataag    60
agacag                                                              66

<210> SEQ ID NO 182
<211> LENGTH: 66
<212> TYPE: DNA
<213> ORGANISM: Artificial
<220> FEATURE:
<223> OTHER INFORMATION: Synthetic DNA

<400> SEQUENCE: 182
caagcagaag acggcatacg agattatcag tagtctcgtg ggctcggaga tgtgtataag    60
agacag                                                               66

<210> SEQ ID NO 183
<211> LENGTH: 66
<212> TYPE: DNA
<213> ORGANISM: Artificial
<220> FEATURE:
<223> OTHER INFORMATION: Synthetic DNA

<400> SEQUENCE: 183
caagcagaag acggcatacg agatgagtct gcgtctcgtg ggctcggaga tgtgtataag    60
agacag                                                               66

<210> SEQ ID NO 184
<211> LENGTH: 66
<212> TYPE: DNA
<213> ORGANISM: Artificial
<220> FEATURE:
<223> OTHER INFORMATION: Synthetic DNA

<400> SEQUENCE: 184
caagcagaag acggcatacg agatcagtcg cagtctcgtg ggctcggaga tgtgtataag    60
agacag                                                               66

<210> SEQ ID NO 185
<211> LENGTH: 66
<212> TYPE: DNA
<213> ORGANISM: Artificial
<220> FEATURE:
<223> OTHER INFORMATION: Synthetic DNA

<400> SEQUENCE: 185
caagcagaag acggcatacg agatgacatc tagtctcgtg ggctcggaga tgtgtataag    60
agacag                                                               66

<210> SEQ ID NO 186
<211> LENGTH: 66
<212> TYPE: DNA
<213> ORGANISM: Artificial
<220> FEATURE:
<223> OTHER INFORMATION: Synthetic DNA

<400> SEQUENCE: 186
caagcagaag acggcatacg agatctgtga cggtctcgtg ggctcggaga tgtgtataag    60
agacag                                                               66

<210> SEQ ID NO 187
<211> LENGTH: 66
<212> TYPE: DNA
<213> ORGANISM: Artificial
<220> FEATURE:
<223> OTHER INFORMATION: Synthetic DNA

<400> SEQUENCE: 187
caagcagaag acggcatacg agataagagg cagtctcgtg ggctcggaga tgtgtataag    60
agacag                                                               66

<210> SEQ ID NO 188
<211> LENGTH: 66

```
<212> TYPE: DNA
<213> ORGANISM: Artificial
<220> FEATURE:
<223> OTHER INFORMATION: Synthetic DNA

<400> SEQUENCE: 188
caagcagaag acggcatacg agatctagta cggtctcgtg ggctcggaga tgtgtataag    60
agacag                                                                66

<210> SEQ ID NO 189
<211> LENGTH: 66
<212> TYPE: DNA
<213> ORGANISM: Artificial
<220> FEATURE:
<223> OTHER INFORMATION: Synthetic DNA

<400> SEQUENCE: 189
caagcagaag acggcatacg agataggagt ccgtctcgtg ggctcggaga tgtgtataag    60
agacag                                                                66

<210> SEQ ID NO 190
<211> LENGTH: 66
<212> TYPE: DNA
<213> ORGANISM: Artificial
<220> FEATURE:
<223> OTHER INFORMATION: Synthetic DNA

<400> SEQUENCE: 190
caagcagaag acggcatacg agatcatgcc tagtctcgtg ggctcggaga tgtgtataag    60
agacag                                                                66

<210> SEQ ID NO 191
<211> LENGTH: 66
<212> TYPE: DNA
<213> ORGANISM: Artificial
<220> FEATURE:
<223> OTHER INFORMATION: Synthetic DNA

<400> SEQUENCE: 191
caagcagaag acggcatacg agatgtagag aggtctcgtg ggctcggaga tgtgtataag    60
agacag                                                                66

<210> SEQ ID NO 192
<211> LENGTH: 66
<212> TYPE: DNA
<213> ORGANISM: Artificial
<220> FEATURE:
<223> OTHER INFORMATION: Synthetic DNA

<400> SEQUENCE: 192
caagcagaag acggcatacg agatcctctc tggtctcgtg ggctcggaga tgtgtataag    60
agacag                                                                66

<210> SEQ ID NO 193
<211> LENGTH: 66
<212> TYPE: DNA
<213> ORGANISM: Artificial
<220> FEATURE:
<223> OTHER INFORMATION: Synthetic DNA

<400> SEQUENCE: 193
caagcagaag acggcatacg agatagcgta gcgtctcgtg ggctcggaga tgtgtataag    60
``` agacag 66

<210> SEQ ID NO 194
<211> LENGTH: 66
<212> TYPE: DNA
<213> ORGANISM: Artificial
<220> FEATURE:
<223> OTHER INFORMATION: Synthetic DNA

<400> SEQUENCE: 194
caagcagaag acggcatacg agattcctct acgtctcgtg ggctcggaga tgtgtataag    60
agacag                                                              66

<210> SEQ ID NO 195
<211> LENGTH: 66
<212> TYPE: DNA
<213> ORGANISM: Artificial
<220> FEATURE:
<223> OTHER INFORMATION: Synthetic DNA

<400> SEQUENCE: 195
caagcagaag acggcatacg agatgacgta cagtctcgtg ggctcggaga tgtgtataag    60
agacag                                                              66

<210> SEQ ID NO 196
<211> LENGTH: 66
<212> TYPE: DNA
<213> ORGANISM: Artificial
<220> FEATURE:
<223> OTHER INFORMATION: Synthetic DNA

<400> SEQUENCE: 196
caagcagaag acggcatacg agatgactgt aggtctcgtg ggctcggaga tgtgtataag    60
agacag                                                              66

<210> SEQ ID NO 197
<211> LENGTH: 66
<212> TYPE: DNA
<213> ORGANISM: Artificial
<220> FEATURE:
<223> OTHER INFORMATION: Synthetic DNA

<400> SEQUENCE: 197
caagcagaag acggcatacg agattcagta cagtctcgtg ggctcggaga tgtgtataag    60
agacag                                                              66

<210> SEQ ID NO 198
<211> LENGTH: 66
<212> TYPE: DNA
<213> ORGANISM: Artificial
<220> FEATURE:
<223> OTHER INFORMATION: Synthetic DNA

<400> SEQUENCE: 198
caagcagaag acggcatacg agatcatgat aggtctcgtg ggctcggaga tgtgtataag    60
agacag                                                              66

<210> SEQ ID NO 199
<211> LENGTH: 66
<212> TYPE: DNA
<213> ORGANISM: Artificial
<220> FEATURE:
<223> OTHER INFORMATION: Synthetic DNA

```
<400> SEQUENCE: 199
caagcagaag acggcatacg agatgcatct cggtctcgtg ggctcggaga tgtgtataag    60
agacag                                                              66

<210> SEQ ID NO 200
<211> LENGTH: 66
<212> TYPE: DNA
<213> ORGANISM: Artificial
<220> FEATURE:
<223> OTHER INFORMATION: Synthetic DNA

<400> SEQUENCE: 200
caagcagaag acggcatacg agattgcaca gagtctcgtg ggctcggaga tgtgtataag    60
agacag                                                              66

<210> SEQ ID NO 201
<211> LENGTH: 66
<212> TYPE: DNA
<213> ORGANISM: Artificial
<220> FEATURE:
<223> OTHER INFORMATION: Synthetic DNA

<400> SEQUENCE: 201
caagcagaag acggcatacg agatgagcta tagtctcgtg ggctcggaga tgtgtataag    60
agacag                                                              66

<210> SEQ ID NO 202
<211> LENGTH: 66
<212> TYPE: DNA
<213> ORGANISM: Artificial
<220> FEATURE:
<223> OTHER INFORMATION: Synthetic DNA

<400> SEQUENCE: 202
caagcagaag acggcatacg agatagtctg cagtctcgtg ggctcggaga tgtgtataag    60
agacag                                                              66

<210> SEQ ID NO 203
<211> LENGTH: 66
<212> TYPE: DNA
<213> ORGANISM: Artificial
<220> FEATURE:
<223> OTHER INFORMATION: Synthetic DNA

<400> SEQUENCE: 203
caagcagaag acggcatacg agatcgctgt gagtctcgtg ggctcggaga tgtgtataag    60
agacag                                                              66

<210> SEQ ID NO 204
<211> LENGTH: 66
<212> TYPE: DNA
<213> ORGANISM: Artificial
<220> FEATURE:
<223> OTHER INFORMATION: Synthetic DNA

<400> SEQUENCE: 204
caagcagaag acggcatacg agatctgatg tggtctcgtg ggctcggaga tgtgtataag    60
agacag                                                              66

<210> SEQ ID NO 205
```

```
<211> LENGTH: 66
<212> TYPE: DNA
<213> ORGANISM: Artificial
<220> FEATURE:
<223> OTHER INFORMATION: Synthetic DNA

<400> SEQUENCE: 205
caagcagaag acggcatacg agatgcactc tagtctcgtg ggctcggaga tgtgtataag      60
agacag                                                                66

<210> SEQ ID NO 206
<211> LENGTH: 66
<212> TYPE: DNA
<213> ORGANISM: Artificial
<220> FEATURE:
<223> OTHER INFORMATION: Synthetic DNA

<400> SEQUENCE: 206
caagcagaag acggcatacg agattctgct cagtctcgtg ggctcggaga tgtgtataag      60
agacag                                                                66

<210> SEQ ID NO 207
<211> LENGTH: 66
<212> TYPE: DNA
<213> ORGANISM: Artificial
<220> FEATURE:
<223> OTHER INFORMATION: Synthetic DNA

<400> SEQUENCE: 207
caagcagaag acggcatacg agattgtatc tagtctcgtg ggctcggaga tgtgtataag      60
agacag                                                                66

<210> SEQ ID NO 208
<211> LENGTH: 66
<212> TYPE: DNA
<213> ORGANISM: Artificial
<220> FEATURE:
<223> OTHER INFORMATION: Synthetic DNA

<400> SEQUENCE: 208
caagcagaag acggcatacg agatacagtg aggtctcgtg ggctcggaga tgtgtataag      60
agacag                                                                66

<210> SEQ ID NO 209
<211> LENGTH: 66
<212> TYPE: DNA
<213> ORGANISM: Artificial
<220> FEATURE:
<223> OTHER INFORMATION: Synthetic DNA

<400> SEQUENCE: 209
caagcagaag acggcatacg agatatgcga tagtctcgtg ggctcggaga tgtgtataag      60
agacag                                                                66

<210> SEQ ID NO 210
<211> LENGTH: 66
<212> TYPE: DNA
<213> ORGANISM: Artificial
<220> FEATURE:
<223> OTHER INFORMATION: Synthetic DNA

<400> SEQUENCE: 210
caagcagaag acggcatacg agatgagaca tggtctcgtg ggctcggaga tgtgtataag      60
```

-continued agacag                                                              66

<210> SEQ ID NO 211
<211> LENGTH: 66
<212> TYPE: DNA
<213> ORGANISM: Artificial
<220> FEATURE:
<223> OTHER INFORMATION: Synthetic DNA

<400> SEQUENCE: 211
caagcagaag acggcatacg agatgtcatg tggtctcgtg ggctcggaga tgtgtataag    60
agacag                                                              66

<210> SEQ ID NO 212
<211> LENGTH: 66
<212> TYPE: DNA
<213> ORGANISM: Artificial
<220> FEATURE:
<223> OTHER INFORMATION: Synthetic DNA

<400> SEQUENCE: 212
caagcagaag acggcatacg agattcatga tagtctcgtg ggctcggaga tgtgtataag    60
agacag                                                              66

<210> SEQ ID NO 213
<211> LENGTH: 66
<212> TYPE: DNA
<213> ORGANISM: Artificial
<220> FEATURE:
<223> OTHER INFORMATION: Synthetic DNA

<400> SEQUENCE: 213
caagcagaag acggcatacg agatgtcatc tcgtctcgtg ggctcggaga tgtgtataag    60
agacag                                                              66

<210> SEQ ID NO 214
<211> LENGTH: 66
<212> TYPE: DNA
<213> ORGANISM: Artificial
<220> FEATURE:
<223> OTHER INFORMATION: Synthetic DNA

<400> SEQUENCE: 214
caagcagaag acggcatacg agattatctc tagtctcgtg ggctcggaga tgtgtataag    60
agacag                                                              66

<210> SEQ ID NO 215
<211> LENGTH: 66
<212> TYPE: DNA
<213> ORGANISM: Artificial
<220> FEATURE:
<223> OTHER INFORMATION: Synthetic DNA

<400> SEQUENCE: 215
caagcagaag acggcatacg agatctgata tagtctcgtg ggctcggaga tgtgtataag    60
agacag                                                              66

<210> SEQ ID NO 216
<211> LENGTH: 66
<212> TYPE: DNA
<213> ORGANISM: Artificial
<220> FEATURE:

<223> OTHER INFORMATION: Synthetic DNA

<400> SEQUENCE: 216

```
caagcagaag acggcatacg agattacgca tggtctcgtg ggctcggaga tgtgtataag    60
agacag                                                               66
```

<210> SEQ ID NO 217
<211> LENGTH: 66
<212> TYPE: DNA
<213> ORGANISM: Artificial
<220> FEATURE:
<223> OTHER INFORMATION: Synthetic DNA

<400> SEQUENCE: 217

```
caagcagaag acggcatacg agatcgtgag tggtctcgtg ggctcggaga tgtgtataag    60
agacag                                                               66
```

<210> SEQ ID NO 218
<211> LENGTH: 66
<212> TYPE: DNA
<213> ORGANISM: Artificial
<220> FEATURE:
<223> OTHER INFORMATION: Synthetic DNA

<400> SEQUENCE: 218

```
caagcagaag acggcatacg agatgacaca tggtctcgtg ggctcggaga tgtgtataag    60
agacag                                                               66
```

<210> SEQ ID NO 219
<211> LENGTH: 66
<212> TYPE: DNA
<213> ORGANISM: Artificial
<220> FEATURE:
<223> OTHER INFORMATION: Synthetic DNA

<400> SEQUENCE: 219

```
caagcagaag acggcatacg agatacatga cggtctcgtg ggctcggaga tgtgtataag    60
agacag                                                               66
```

<210> SEQ ID NO 220
<211> LENGTH: 66
<212> TYPE: DNA
<213> ORGANISM: Artificial
<220> FEATURE:
<223> OTHER INFORMATION: Synthetic DNA

<400> SEQUENCE: 220

```
caagcagaag acggcatacg agatgcgtct aggtctcgtg ggctcggaga tgtgtataag    60
agacag                                                               66
```

<210> SEQ ID NO 221
<211> LENGTH: 66
<212> TYPE: DNA
<213> ORGANISM: Artificial
<220> FEATURE:
<223> OTHER INFORMATION: Synthetic DNA

<400> SEQUENCE: 221

```
caagcagaag acggcatacg agattcacgc tggtctcgtg ggctcggaga tgtgtataag    60
agacag                                                               66
```

```
<210> SEQ ID NO 222
<211> LENGTH: 66
<212> TYPE: DNA
<213> ORGANISM: Artificial
<220> FEATURE:
<223> OTHER INFORMATION: Synthetic DNA

<400> SEQUENCE: 222
caagcagaag acggcatacg agattcatgt acgtctcgtg ggctcggaga tgtgtataag      60
agacag                                                                66

<210> SEQ ID NO 223
<211> LENGTH: 66
<212> TYPE: DNA
<213> ORGANISM: Artificial
<220> FEATURE:
<223> OTHER INFORMATION: Synthetic DNA

<400> SEQUENCE: 223
caagcagaag acggcatacg agattagtga cggtctcgtg ggctcggaga tgtgtataag      60
agacag                                                                66

<210> SEQ ID NO 224
<211> LENGTH: 66
<212> TYPE: DNA
<213> ORGANISM: Artificial
<220> FEATURE:
<223> OTHER INFORMATION: Synthetic DNA

<400> SEQUENCE: 224
caagcagaag acggcatacg agatcacgat aggtctcgtg ggctcggaga tgtgtataag      60
agacag                                                                66

<210> SEQ ID NO 225
<211> LENGTH: 66
<212> TYPE: DNA
<213> ORGANISM: Artificial
<220> FEATURE:
<223> OTHER INFORMATION: Synthetic DNA

<400> SEQUENCE: 225
caagcagaag acggcatacg agatacacac tggtctcgtg ggctcggaga tgtgtataag      60
agacag                                                                66

<210> SEQ ID NO 226
<211> LENGTH: 66
<212> TYPE: DNA
<213> ORGANISM: Artificial
<220> FEATURE:
<223> OTHER INFORMATION: Synthetic DNA

<400> SEQUENCE: 226
caagcagaag acggcatacg agatagcatc acgtctcgtg ggctcggaga tgtgtataag      60
agacag                                                                66

<210> SEQ ID NO 227
<211> LENGTH: 66
<212> TYPE: DNA
<213> ORGANISM: Artificial
<220> FEATURE:
<223> OTHER INFORMATION: Synthetic DNA

<400> SEQUENCE: 227
```

```
caagcagaag acggcatacg agattagtcg tagtctcgtg ggctcggaga tgtgtataag    60
agacag                                                               66

<210> SEQ ID NO 228
<211> LENGTH: 66
<212> TYPE: DNA
<213> ORGANISM: Artificial
<220> FEATURE:
<223> OTHER INFORMATION: Synthetic DNA

<400> SEQUENCE: 228
caagcagaag acggcatacg agatgcatcg cggtctcgtg ggctcggaga tgtgtataag    60
agacag                                                               66

<210> SEQ ID NO 229
<211> LENGTH: 66
<212> TYPE: DNA
<213> ORGANISM: Artificial
<220> FEATURE:
<223> OTHER INFORMATION: Synthetic DNA

<400> SEQUENCE: 229
caagcagaag acggcatacg agatatcatg tcgtctcgtg ggctcggaga tgtgtataag    60
agacag                                                               66

<210> SEQ ID NO 230
<211> LENGTH: 66
<212> TYPE: DNA
<213> ORGANISM: Artificial
<220> FEATURE:
<223> OTHER INFORMATION: Synthetic DNA

<400> SEQUENCE: 230
caagcagaag acggcatacg agatgtactc tagtctcgtg ggctcggaga tgtgtataag    60
agacag                                                               66

<210> SEQ ID NO 231
<211> LENGTH: 66
<212> TYPE: DNA
<213> ORGANISM: Artificial
<220> FEATURE:
<223> OTHER INFORMATION: Synthetic DNA

<400> SEQUENCE: 231
caagcagaag acggcatacg agatagtgca tagtctcgtg ggctcggaga tgtgtataag    60
agacag                                                               66

<210> SEQ ID NO 232
<211> LENGTH: 66
<212> TYPE: DNA
<213> ORGANISM: Artificial
<220> FEATURE:
<223> OTHER INFORMATION: Synthetic DNA

<400> SEQUENCE: 232
caagcagaag acggcatacg agatcgcatc aggtctcgtg ggctcggaga tgtgtataag    60
agacag                                                               66

<210> SEQ ID NO 233
<211> LENGTH: 66
<212> TYPE: DNA
<213> ORGANISM: Artificial
```

```
<220> FEATURE:
<223> OTHER INFORMATION: Synthetic DNA

<400> SEQUENCE: 233
caagcagaag acggcatacg agatcgctat aggtctcgtg ggctcggaga tgtgtataag    60
agacag                                                                66

<210> SEQ ID NO 234
<211> LENGTH: 66
<212> TYPE: DNA
<213> ORGANISM: Artificial
<220> FEATURE:
<223> OTHER INFORMATION: Synthetic DNA

<400> SEQUENCE: 234
caagcagaag acggcatacg agatgtcgat aggtctcgtg ggctcggaga tgtgtataag    60
agacag                                                                66

<210> SEQ ID NO 235
<211> LENGTH: 66
<212> TYPE: DNA
<213> ORGANISM: Artificial
<220> FEATURE:
<223> OTHER INFORMATION: Synthetic DNA

<400> SEQUENCE: 235
caagcagaag acggcatacg agatacacag tagtctcgtg ggctcggaga tgtgtataag    60
agacag                                                                66

<210> SEQ ID NO 236
<211> LENGTH: 66
<212> TYPE: DNA
<213> ORGANISM: Artificial
<220> FEATURE:
<223> OTHER INFORMATION: Synthetic DNA

<400> SEQUENCE: 236
caagcagaag acggcatacg agatcagatg tagtctcgtg ggctcggaga tgtgtataag    60
agacag                                                                66

<210> SEQ ID NO 237
<211> LENGTH: 66
<212> TYPE: DNA
<213> ORGANISM: Artificial
<220> FEATURE:
<223> OTHER INFORMATION: Synthetic DNA

<400> SEQUENCE: 237
caagcagaag acggcatacg agatctctac aggtctcgtg ggctcggaga tgtgtataag    60
agacag                                                                66

<210> SEQ ID NO 238
<211> LENGTH: 66
<212> TYPE: DNA
<213> ORGANISM: Artificial
<220> FEATURE:
<223> OTHER INFORMATION: Synthetic DNA

<400> SEQUENCE: 238
caagcagaag acggcatacg agatgtcact aggtctcgtg ggctcggaga tgtgtataag    60
agacag                                                                66
```

```
<210> SEQ ID NO 239
<211> LENGTH: 66
<212> TYPE: DNA
<213> ORGANISM: Artificial
<220> FEATURE:
<223> OTHER INFORMATION: Synthetic DNA

<400> SEQUENCE: 239
caagcagaag acggcatacg agattgtact aggtctcgtg ggctcggaga tgtgtataag     60
agacag                                                                66

<210> SEQ ID NO 240
<211> LENGTH: 66
<212> TYPE: DNA
<213> ORGANISM: Artificial
<220> FEATURE:
<223> OTHER INFORMATION: Synthetic DNA

<400> SEQUENCE: 240
caagcagaag acggcatacg agatacgcta tggtctcgtg ggctcggaga tgtgtataag     60
agacag                                                                66

<210> SEQ ID NO 241
<211> LENGTH: 66
<212> TYPE: DNA
<213> ORGANISM: Artificial
<220> FEATURE:
<223> OTHER INFORMATION: Synthetic DNA

<400> SEQUENCE: 241
caagcagaag acggcatacg agatatgtat aggtctcgtg ggctcggaga tgtgtataag     60
agacag                                                                66

<210> SEQ ID NO 242
<211> LENGTH: 66
<212> TYPE: DNA
<213> ORGANISM: Artificial
<220> FEATURE:
<223> OTHER INFORMATION: Synthetic DNA

<400> SEQUENCE: 242
caagcagaag acggcatacg agattgtgac aggtctcgtg ggctcggaga tgtgtataag     60
agacag                                                                66

<210> SEQ ID NO 243
<211> LENGTH: 126
<212> TYPE: DNA
<213> ORGANISM: Saccharum spontaneum

<400> SEQUENCE: 243
acagggaagt gaaagagaag tggccattga aaaacctaat attgttacgg aagtgcctcg     60
cgtccgcgtc gaagctcgtc caaagcctca tgagctggtc tggtatgact ggcgcattca    120
gctcga                                                               126

<210> SEQ ID NO 244
<211> LENGTH: 89
<212> TYPE: DNA
<213> ORGANISM: Saccharum spontaneum

<400> SEQUENCE: 244
caagcgcagg aaaaggaaac gctgcccgca gttcctcacc cggctccccc gttgtcgccc     60
```

```
tcagccgctt ccgccatcct cgctgtcac                                       89
```

<210> SEQ ID NO 245
<211> LENGTH: 112
<212> TYPE: DNA
<213> ORGANISM: Saccharum spontaneum

<400> SEQUENCE: 245

```
caataaaatg ggaacatgat ggaaggacag gttacccgat gcattatgag catacagaac    60
ggcctacaaa acaccgattg gaatgtcacc atatcaactt atctatggaa ga           112
```

<210> SEQ ID NO 246
<211> LENGTH: 156
<212> TYPE: DNA
<213> ORGANISM: Saccharum spontaneum

<400> SEQUENCE: 246

```
cagacagata gccacgagac gaggactcac agagctttcg gtgagcctcc atagtccaga    60
gatagtctct gttggttctt tttctttcct ttttcgacga gatctttttt tcttggtccc   120
acacgaactg gcgttgtgct tctattatgc tgtcac                             156
```

<210> SEQ ID NO 247
<211> LENGTH: 121
<212> TYPE: DNA
<213> ORGANISM: Saccharum spontaneum

<400> SEQUENCE: 247

```
catcatggtg cgaatcttcg agttcagacc cctcataaaa caagcttgct tctttcgatc    60
tgagttgatt tggtcagctg catactatga taaatgattg aacctaccca catattgcat   120
c                                                                   121
```

<210> SEQ ID NO 248
<211> LENGTH: 126
<212> TYPE: DNA
<213> ORGANISM: Saccharum spontaneum

<400> SEQUENCE: 248

```
catgaaagct cacaaacccg ctcgagctct gggtcgatgg ctcatcccat ttgcctcgag    60
aatgcccctc ctccgctgcg caggtgccgc ctctccttac atcacgcgtc accatgccat   120
gcccgc                                                              126
```

<210> SEQ ID NO 249
<211> LENGTH: 100
<212> TYPE: DNA
<213> ORGANISM: Saccharum spontaneum

<400> SEQUENCE: 249

```
ctaatgcttg gtagctcata catgaacctt atagtcgtcc tgcatttaac aactgtcaag    60
gacaggttcg agtgcacatg tataatgcta tcaacgtttt                         100
```

<210> SEQ ID NO 250
<211> LENGTH: 100
<212> TYPE: DNA
<213> ORGANISM: Saccharum spontaneum

<400> SEQUENCE: 250

```
tagccacata actttcccac aatgtaaagg tattttcaat aaagaatcta ggagtactaa    60
```

```
<210> SEQ ID NO 251
<211> LENGTH: 153
<212> TYPE: DNA
<213> ORGANISM: Saccharum spontaneum

<400> SEQUENCE: 251
ctcgaaaatc tctaacaaac tcattccaag taataggagg agcattgtta ggacgtgcag    60
cttgatacga ctcccaccaa gtctgtgttg tccctgtaa ctgaccagtt gcatataaca   120
cctttccat atcattgcat tgagcgatgt tca                                153

<210> SEQ ID NO 252
<211> LENGTH: 100
<212> TYPE: DNA
<213> ORGANISM: Saccharum spontaneum

<400> SEQUENCE: 252
ctcgagcgat gtccgatagg aacaggggaa gttgtcgaat gatgacccgg tcgtcggtgg    60
ccccacccaa ctgactagcc aagcggaagt cagcgagcca                         100

<210> SEQ ID NO 253
<211> LENGTH: 100
<212> TYPE: DNA
<213> ORGANISM: Saccharum spontaneum

<400> SEQUENCE: 253
tcggaggatc gaagcccttc acccgagcca ccaggccctc gggtctttag caaagccatc    60
cgcaaaacgt tactcccagc tcggttcctc ccccatgact                         100

<210> SEQ ID NO 254
<211> LENGTH: 100
<212> TYPE: DNA
<213> ORGANISM: Saccharum spontaneum

<400> SEQUENCE: 254
ctcgagcggt gtcagagagg aacagggga gctgccggat gatgttccgg tcgtcggtgg    60
ccccgcccag ctgacacgcc aagcggaaat cggcgagcca                         100

<210> SEQ ID NO 255
<211> LENGTH: 100
<212> TYPE: DNA
<213> ORGANISM: Saccharum spontaneum

<400> SEQUENCE: 255
tcggaggatc gtagcccttc acccgagcct ccgggccctc gggtcttcag taaggctatt    60
cgtgaaatga tactcccggc gcggtttcgc ccccccccca                         100

<210> SEQ ID NO 256
<211> LENGTH: 100
<212> TYPE: DNA
<213> ORGANISM: Saccharum spontaneum

<400> SEQUENCE: 256
ctcgagcggt gtcgaagagg aacagaggga gctgtcggat gatgacctgg tcgtcggtgg    60
ccccacccag ctgacatgcc aagcggaaat cggcgagcca                         100

<210> SEQ ID NO 257
<211> LENGTH: 100
```

```
<212> TYPE: DNA
<213> ORGANISM: Saccharum spontaneum

<400> SEQUENCE: 257
tcggaggatc gcagcccatc acccgagcct ccaggccctc gggtcttcag taaggctatc      60
cgcgaaacta tactcccggc gcagtttcgc cctcccacga                           100

<210> SEQ ID NO 258
<211> LENGTH: 100
<212> TYPE: DNA
<213> ORGANISM: Saccharum spontaneum

<400> SEQUENCE: 258
ctcgagcggt gtcggagagg aacaggggga gctgtcggat gatgacccgg tcgtcggtgg      60
ccccacccag ctgacacgcc aagcggaaat cggcgagcca                           100

<210> SEQ ID NO 259
<211> LENGTH: 100
<212> TYPE: DNA
<213> ORGANISM: Saccharum spontaneum

<400> SEQUENCE: 259
tcggaggatc gtagcccttc acccgagcct ccgggccctc gggtcttcag taaggctatc      60
cgcgaaataa tactcccggc gcggtttcgc cctcccacga                           100

<210> SEQ ID NO 260
<211> LENGTH: 100
<212> TYPE: DNA
<213> ORGANISM: Saccharum spontaneum

<400> SEQUENCE: 260
ctcgagcggt gtcggagagg aacaggggga gctgtcggat gatgacccgg tcgtcggtgg      60
ccccgcccag ctgacatgcc aagcggaaat cggcgagcca                           100

<210> SEQ ID NO 261
<211> LENGTH: 100
<212> TYPE: DNA
<213> ORGANISM: Saccharum spontaneum

<400> SEQUENCE: 261
tcggaggatc gaagcccttc acccgagcct ccgggccctc gggtcttcag caaggctatc      60
cgcgaaacga tactcctggc gcggtttcgc cctcccacga                           100

<210> SEQ ID NO 262
<211> LENGTH: 100
<212> TYPE: DNA
<213> ORGANISM: Saccharum spontaneum

<400> SEQUENCE: 262
ctcgagcggt gttagagagg aacaggggga gctgtcggat gatgacccgg tcgtcggtgg      60
ccccacccag ctgacatgcc aagcggaaat cggcaagcca                           100

<210> SEQ ID NO 263
<211> LENGTH: 100
<212> TYPE: DNA
<213> ORGANISM: Saccharum spontaneum

<400> SEQUENCE: 263
tcggaggatc gtagcccttc acccgagcct ccgggccctc gggtcttcag taaggctatc      60
```
cgcgaaacga tactcccggc gcggtttcgc cctcccacga        100

<210> SEQ ID NO 264
<211> LENGTH: 100
<212> TYPE: DNA
<213> ORGANISM: Saccharum spontaneum

<400> SEQUENCE: 264
ctcgggcggt atcggagagg aatagggga gttgtcggat gatgacccgg tcgtcggtgg        60
ccccgcctag ctaacacgcc aagcagaaat cggcgagcca        100

<210> SEQ ID NO 265
<211> LENGTH: 100
<212> TYPE: DNA
<213> ORGANISM: Saccharum spontaneum

<400> SEQUENCE: 265
tcagaagatc gtagcccttc acccgagcct ccgggctctc gggtctttag taaggctatc        60
cgcgagacgg tgctcccggc tcggtttcgc cctcccacga        100

<210> SEQ ID NO 266
<211> LENGTH: 100
<212> TYPE: DNA
<213> ORGANISM: Saccharum spontaneum

<400> SEQUENCE: 266
ctcgggcggt gtcggagagg aacaggggga gttatcgaat gatgacccgg tcgtcggtgg        60
ccccgcccag ctgacacgcc aagcggaaat cggtgagcca        100

<210> SEQ ID NO 267
<211> LENGTH: 100
<212> TYPE: DNA
<213> ORGANISM: Saccharum spontaneum

<400> SEQUENCE: 267
tcggaagatc gtagtccttc acccgagcct ccgggccctc tggtcttctg taaagctatc        60
cgtgaaatgg tgctcccggc tcagtttcgc cctcccacga        100

<210> SEQ ID NO 268
<211> LENGTH: 100
<212> TYPE: DNA
<213> ORGANISM: Saccharum spontaneum

<400> SEQUENCE: 268
ctcgggcggt gtcggagagg aacaggggga gttgtcgaat gataacccgg tcgtcggtgg        60
ccccacccag ctgacatgcc aagcggaaat cagcaagcca        100

<210> SEQ ID NO 269
<211> LENGTH: 100
<212> TYPE: DNA
<213> ORGANISM: Saccharum spontaneum

<400> SEQUENCE: 269
tcgaaagatc gtagtccttc acccgagcct ccgggccctc gggtcttcag taaggctatc        60
cgtgaaacgg tgctcccatc tcggtttcgc cctcccacga        100

<210> SEQ ID NO 270
<211> LENGTH: 170
<212> TYPE: DNA
<213> ORGANISM: Saccharum spontaneum

<400> SEQUENCE: 270
ctgagtctag taataagact ttgatcaagc ttatcaagaa gaaaattgag gaaaattcaa    60
ggaggtggca tgaagttttg tctgaagctc tatgggcaca tcgtatttca aaacatggtg   120
ctaccaaagt tattcctttt aagctagtat atgaccaaga ggccgtgtta              170

<210> SEQ ID NO 271
<211> LENGTH: 84
<212> TYPE: DNA
<213> ORGANISM: Saccharum spontaneum

<400> SEQUENCE: 271
gaagctactg ttggttggga gctaatcgga atgactattt atcattttt gaaaataaaa    60 agggatgact gatacttatg caca                                           84

<210> SEQ ID NO 272
<211> LENGTH: 85
<212> TYPE: DNA
<213> ORGANISM: Saccharum spontaneum

<400> SEQUENCE: 272
gacaatgcat cacgccgatg tagccgagat catcccttcg ctgcccctgg agatcaggtg    60
gccaccgttc cgtctccgcc attac                                          85

<210> SEQ ID NO 273
<211> LENGTH: 160
<212> TYPE: DNA
<213> ORGANISM: Saccharum spontaneum

<400> SEQUENCE: 273
gaccacgcgg gcgacatcga caccagcaag agcacgagcg ggattctctt cttcctcggc    60
aggtgcctcg ttagctggca gtcggtcaag cagcaggtgg tggccctgtc cagctgcgag   120
gccgagtaca tagcggcttc caccgcttcg acttaggcgc                         160

<210> SEQ ID NO 274
<211> LENGTH: 104
<212> TYPE: DNA
<213> ORGANISM: Saccharum spontaneum

<400> SEQUENCE: 274
gacctggcag gcgacgtgaa tgactgaaag agcaccagcg ggctgatctt cttcctggca    60
ggaggcccga ttgcttggca gtcggcaaaa cagagggtgg ttgc                   104

<210> SEQ ID NO 275
<211> LENGTH: 100
<212> TYPE: DNA
<213> ORGANISM: Saccharum spontaneum

<400> SEQUENCE: 275
gagatgagag gagcgaggaa aggagaggaa gggaggtgag gtgttgtagt gtggatacag    60
ctaacagctt acatggaggt ggagtatggg gcctggttta                        100

<210> SEQ ID NO 276
<211> LENGTH: 100
<212> TYPE: DNA
<213> ORGANISM: Saccharum spontaneum

<400> SEQUENCE: 276

```
gcgcaggaaa gaggtcgtgg acaaatccag ggcgtgttta gttgggctga ttttggacgt    60
ccaaaatctg cacagtgtaa gattccatac tgtagcattt                         100

<210> SEQ ID NO 277
<211> LENGTH: 100
<212> TYPE: DNA
<213> ORGANISM: Saccharum spontaneum

<400> SEQUENCE: 277
gagcgagacg agagacaaac aaaaaggtgg tgacgataag aggcgccacg cactaaaccc    60
gcaccatggt catggagtag cgtgtaagga acaagtagca                        100

<210> SEQ ID NO 278
<211> LENGTH: 100
<212> TYPE: DNA
<213> ORGANISM: Saccharum spontaneum

<400> SEQUENCE: 278
gcgagaggtg gtggtacacg cctacctagg tggtgggctc gtcgtcgtca gacaccaggc    60
gtcacaggcc gtcgtccgtt tctgccgccc catgctcgct                        100

<210> SEQ ID NO 279
<211> LENGTH: 100
<212> TYPE: DNA
<213> ORGANISM: Saccharum spontaneum

<400> SEQUENCE: 279
gcacgacatg gtatggcagg ggacaaagac ggagatgggg tgcgccgtgg gggatggctt    60
cagcgacatg ccagagtggg ccacggcgcg acagagtggg                        100

<210> SEQ ID NO 280
<211> LENGTH: 100
<212> TYPE: DNA
<213> ORGANISM: Saccharum spontaneum

<400> SEQUENCE: 280
gctgctccct tctccggcgc gaggctcctc gtcgtggcct tctctagcgc ggtggcaccg    60
catccgctcc catcccgcgc tgctccacac tccgcgcgcg                        100

<210> SEQ ID NO 281
<211> LENGTH: 100
<212> TYPE: DNA
<213> ORGANISM: Saccharum spontaneum

<400> SEQUENCE: 281
gccaccggcc tcgtggtcgt gagaccgagg agaccggtac ctgggatggg ctggtagtcc    60
tcatctgtgc tgtcagaagt cacatcctca ggtatatcag                        100

<210> SEQ ID NO 282
<211> LENGTH: 100
<212> TYPE: DNA
<213> ORGANISM: Saccharum spontaneum

<400> SEQUENCE: 282
gtgagcgccc agacgttcct gagacagcag ctgagcagga tgccagagtt gacgagcttg    60
ctgaggcaga gcttgcggac cttgaggctc agactgctga                        100

<210> SEQ ID NO 283
<211> LENGTH: 130
```

<212> TYPE: DNA
<213> ORGANISM: Saccharum spontaneum

<400> SEQUENCE: 283

```
gcggttgtgt gttgtggccg ggccattggc ggatgagcga gcgagtgcaa ccagaggcga      60
acgtacccaa cccagcgaca gcaagtcagc aacatatatt ctctcactcg atcacgtccc     120
cacgggccta                                                            130
```

<210> SEQ ID NO 284
<211> LENGTH: 151
<212> TYPE: DNA
<213> ORGANISM: Saccharum spontaneum

<400> SEQUENCE: 284

```
gctaagaaca ttcggtgtct gcaatgtgag aagtgaacac tctagtaact taagaaatgc      60
tatcaacaaa atgagccatc ttgttcatct agacattgcg gctctagggg agagcgaagt     120
gttgcagcta gagggacttc atttgcctcc a                                    151
```

<210> SEQ ID NO 285
<211> LENGTH: 100
<212> TYPE: DNA
<213> ORGANISM: Saccharum spontaneum

<400> SEQUENCE: 285

```
ggcagaggga gccaagcaac taatcaaact caaagcgcct cctaccaacc gaaaaggcga      60
gaaaaagcta agccaaggtg gggatcggaa gaattatcca                           100
```

<210> SEQ ID NO 286
<211> LENGTH: 100
<212> TYPE: DNA
<213> ORGANISM: Saccharum spontaneum

<400> SEQUENCE: 286

```
tagcaagtgc ggctgctatc ttgagaggtt ggcgctgtgg tgctaggctt tttgccgtgc      60
tgggtgcctg ggtggtggag atggatggat gtatatatag                           100
```

<210> SEQ ID NO 287
<211> LENGTH: 169
<212> TYPE: DNA
<213> ORGANISM: Saccharum spontaneum

<400> SEQUENCE: 287

```
gtatgtcacc tttgagggtt ttgactttta atgaatttgc aactatggca cccaattttt      60
gcagctgtag tgttgcttcc atcatcagtc aggtctacac ctaccaaata attctagtgt     120
tccatggctc caatgaaatg tggattgaaa gttaatctta attgcatta                 169
```

<210> SEQ ID NO 288
<211> LENGTH: 160
<212> TYPE: DNA
<213> ORGANISM: Saccharum spontaneum

<400> SEQUENCE: 288

```
gtgagcgccc agatgttcct gagacagcag ctgagcagga cgctacagtt gacgagcttg      60
ctgaggcaga gctcgcagac cttgagactc agactgctga catacctgag gatgtcactt     120
cagatagcac agatgaggac taccagccca ttcccaggta                           160
```

<210> SEQ ID NO 289

<211> LENGTH: 160
<212> TYPE: DNA
<213> ORGANISM: Saccharum spontaneum

<400> SEQUENCE: 289

```
gtgagcgccc agatgttcct gagacagcag ctgagcagga cgctacagtt gacgagcttg    60
ctgaggcaga gctcgcggat cttgaggctc agactgctga catacctgag gatgccactt   120
ctgatagcac agatgaggac taccagccca ttcccaggta                         160
```

<210> SEQ ID NO 290
<211> LENGTH: 100
<212> TYPE: DNA
<213> ORGANISM: Saccharum spontaneum

<400> SEQUENCE: 290

```
gtggggcgtg tgtctcaccc aacgaagtag tggccaagta aggtagccag cggtgggcga    60
gctccttatt tgatgacgtg gtccagaaaa tggttctctt                         100
```

<210> SEQ ID NO 291
<211> LENGTH: 100
<212> TYPE: DNA
<213> ORGANISM: Saccharum spontaneum

<400> SEQUENCE: 291

```
tcatgtccaa gtactcgcaa gctgatgctt gggggctaca accactgggg tctcctgagc    60
gcaaattgtc aggatcgcgc gctgattcta ccacgcggcc                         100
```

<210> SEQ ID NO 292
<211> LENGTH: 146
<212> TYPE: DNA
<213> ORGANISM: Saccharum spontaneum

<400> SEQUENCE: 292

```
taacccacca aagatagcct tgcatgctcc ttagtgtcgc ttattttggt ttaagacggg    60
taagtctagc tgagtacctt ctcgtactca gggcgttgtt ctcattgttg ttgcagatgg   120
ttagatgtac tatggatatt gcgtca                                        146
```

<210> SEQ ID NO 293
<211> LENGTH: 148
<212> TYPE: DNA
<213> ORGANISM: Saccharum spontaneum

<400> SEQUENCE: 293

```
tagcccacta aagaaagcc ttgcataacc cttgatgtca ctttattttg gtttaagaca    60
gataagtcta gctgagtacc ttctcgtact tagggcgttg ttcccattgt tgttgtagat   120
gattagatgt actacggcta ttgcgtca                                      148
```

<210> SEQ ID NO 294
<211> LENGTH: 56
<212> TYPE: DNA
<213> ORGANISM: Saccharum spontaneum

<400> SEQUENCE: 294

```
tcaaatgaag gccaagcgtc aagcagtgag cattctttca atttcttggc aaccca        56
```

<210> SEQ ID NO 295
<211> LENGTH: 80
<212> TYPE: DNA
<213> ORGANISM: Saccharum spontaneum

<400> SEQUENCE: 295
caaagtctag taggtactct cgagaccctc atacgctctg atggcggcga acatagcact    60
cattgcctgg ttgtcgctag                                                80

<210> SEQ ID NO 296
<211> LENGTH: 100
<212> TYPE: DNA
<213> ORGANISM: Saccharum spontaneum

<400> SEQUENCE: 296
caagcactgg gttgattctg gcaactacgg catcaaattt gttcctctgg gaccgggctt    60
cttgctccag cacatcgaac tgtgccttga ccctctgatg                         100

<210> SEQ ID NO 297
<211> LENGTH: 100
<212> TYPE: DNA
<213> ORGANISM: Saccharum spontaneum

<400> SEQUENCE: 297
gcgagcgaac aaactgaccg aggagcttaa cggtaagtat ccactggtcg ggttttctgc    60
tgtagcgatt gtcttgcctg atggaacttc aaaatgcatg                         100

<210> SEQ ID NO 298
<211> LENGTH: 126
<212> TYPE: DNA
<213> ORGANISM: Saccharum spontaneum

<400> SEQUENCE: 298
catgaaagct cacaaacccg ctcgagctct gggtcgatgg ctcatcccat ttgcctcgag    60
aatgcccctc ctccgctgcg caggtgccgc ctctccttac atcacgcgtc accatgccat   120
gcccgc                                                              126

<210> SEQ ID NO 299
<211> LENGTH: 100
<212> TYPE: DNA
<213> ORGANISM: Saccharum spontaneum

<400> SEQUENCE: 299
ctaaaggaag aaaccaacac gacaaaaaac agaaaaggta cgtaccagcg tggaagttct    60
caagggtgga gaattcctcg gcctgccgag ccacctgctc                         100

<210> SEQ ID NO 300
<211> LENGTH: 100
<212> TYPE: DNA
<213> ORGANISM: Saccharum spontaneum

<400> SEQUENCE: 300
gcggagcacc ttggtgtcgg agcagaacgc cttggagttg gcttggaatg ccctggagtc    60
aaagcgaaat gcctggtcag aggcggacca ggaggtgctc                         100

<210> SEQ ID NO 301
<211> LENGTH: 100
<212> TYPE: DNA
<213> ORGANISM: Saccharum spontaneum

<400> SEQUENCE: 301
ctcgggcggt gtcggagagg aacaggggga gttgtcgaat gataacccgg tcgtcggtgg    60

```
ccccacccag ctgacatgcc aagcggaaat cggcaagcca                  100
```

<210> SEQ ID NO 302
<211> LENGTH: 100
<212> TYPE: DNA
<213> ORGANISM: Saccharum spontaneum

<400> SEQUENCE: 302

```
tcgaaagatc gtagtccttc acccgagcct ccgggccctc gggtcttcag taaggctatc    60
cgtgaaacgg tgctcccggc tcggtttcgc cctcccacga                         100
```

<210> SEQ ID NO 303
<211> LENGTH: 170
<212> TYPE: DNA
<213> ORGANISM: Saccharum spontaneum

<400> SEQUENCE: 303

```
ctgagtctag taataagact ttgatcaagc ttatcaagaa gaaaattgag gaaaattcaa    60
ggaggtggca tgaagttttg tctgaagctc tatgggcaca tcgtatttca aaacatggtg  120
ctaccaaagt tattccttttt aagctagtat atgaccaaga ggccgtgtta             170
```

<210> SEQ ID NO 304
<211> LENGTH: 100
<212> TYPE: DNA
<213> ORGANISM: Saccharum spontaneum

<400> SEQUENCE: 304

```
ctggaagggt gatttagtct ctgatcggaa ggcctagcta aggaggaaca acgctcgctt    60
gcgactctga cctgcctctc cgaccggaag gcctggccaa                         100
```

<210> SEQ ID NO 305
<211> LENGTH: 100
<212> TYPE: DNA
<213> ORGANISM: Saccharum spontaneum

<400> SEQUENCE: 305

```
tcggagtcag aatcgagcgt cgttcctcct tggctaggcc ttttggttgg agaggcgggt    60
cagagttaga agcgagcatc gttcctcctt ggccaggcct                         100
```

<210> SEQ ID NO 306
<211> LENGTH: 85
<212> TYPE: DNA
<213> ORGANISM: Saccharum spontaneum

<400> SEQUENCE: 306

```
ctggcacctc ctccaaactc tttccttctc tcctctctct atttctaaag actagatcct    60
aataaggact aatcttctct cgata                                         85
```

<210> SEQ ID NO 307
<211> LENGTH: 84
<212> TYPE: DNA
<213> ORGANISM: Saccharum spontaneum

<400> SEQUENCE: 307

```
gaagctactg ttggttggga gctaatcgga atgactattt atcatttttt gaaaataaaa    60
agggatgact gatacttatg caca                                          84
```

<210> SEQ ID NO 308
<211> LENGTH: 100

```
<210> SEQ ID NO 308
<211> LENGTH: 100
<212> TYPE: DNA
<213> ORGANISM: Saccharum spontaneum

<400> SEQUENCE: 308
gaagggtggt aggtgggcat cgaacggacc tggtacatgg gcttgggaaa gccatagaag    60
tcgtagatgg tgtcgttgct gccgcggata acgttgaccg                         100

<210> SEQ ID NO 309
<211> LENGTH: 100
<212> TYPE: DNA
<213> ORGANISM: Saccharum spontaneum

<400> SEQUENCE: 309
gcgggcagac ccaaaccaga gacgcggcac gcgacgcggg agggcgagga gcagcggcgg    60
cgcggcgaca tcgcgaggcc agggccagac gcaacggccg                         100

<210> SEQ ID NO 310
<211> LENGTH: 146
<212> TYPE: DNA
<213> ORGANISM: Saccharum spontaneum

<400> SEQUENCE: 310
gacacacgac acgagagttt ggccatggca acggtctcct cgctcgctcg ctcctcactg    60
gcggccgtca cacctggaga gtgaccgact ggcagtagct gtagcagccc tcagcctcac   120
gcgacgcagc gcaggcctct ggatgc                                        146

<210> SEQ ID NO 311
<211> LENGTH: 160
<212> TYPE: DNA
<213> ORGANISM: Saccharum spontaneum

<400> SEQUENCE: 311
gaccacgcgg gcgacatcga caccagcaag agcacgagcg ggattctctt cttcctcggc    60
aggtgcctcg ttagctggca gtcggtcaag cagcaggtgg tggccctgtc cagctgcgag   120
gccgagtaca tagcggcttc caccgcttcg acttaggcgc                         160

<210> SEQ ID NO 312
<211> LENGTH: 100
<212> TYPE: DNA
<213> ORGANISM: Saccharum spontaneum

<400> SEQUENCE: 312
gacgcggcga tcaggccgga aggagtcgtg gcgccgccgt ccgtgagctt acctgattga    60
tttgattgat tgttgcattg gttaattatt attagttact                         100

<210> SEQ ID NO 313
<211> LENGTH: 100
<212> TYPE: DNA
<213> ORGANISM: Saccharum spontaneum

<400> SEQUENCE: 313
gagaatgccg gtgagcagga tcgccgtggg cgctccgggc gagctgtccc accccgacac    60
cgccaaggcc gccgtcgccg agttcatctc catgctcatc                         100

<210> SEQ ID NO 314
<211> LENGTH: 111
<212> TYPE: DNA
<213> ORGANISM: Saccharum spontaneum
```

```
<400> SEQUENCE: 314
gagcggcggc gacggcggaa atggagaggg cggtggggggg aaagcggcct agggttcgag    60
gggagaggga atggatacga ttgaggggtg aggggcgcgg ggatggggcg a             111

<210> SEQ ID NO 315
<211> LENGTH: 155
<212> TYPE: DNA
<213> ORGANISM: Saccharum spontaneum

<400> SEQUENCE: 315
gaggacagcg accagagctg gaggaggatc gatcggcgga gggtggtctg ttatgttccg    60
tgaccaggcg tgactccgtg tcgcatatga ttagggaaag gatatgaacc gtgagctccg   120
tggcgctgaa gttgcgccgg ttagctggtc actga                              155

<210> SEQ ID NO 316
<211> LENGTH: 146
<212> TYPE: DNA
<213> ORGANISM: Saccharum spontaneum

<400> SEQUENCE: 316
taacccacca aagatagcct tgcatgctcc ttagtgtcgc ttattttggt ttaagacggg    60
taagtctagc tgagtaccTT ctcgtactca gggcgttgtt ctcattgttg ttgcagatgg   120
ttagatgtac tatggatatt gcgtca                                        146

<210> SEQ ID NO 317
<211> LENGTH: 148
<212> TYPE: DNA
<213> ORGANISM: Saccharum spontaneum

<400> SEQUENCE: 317
tagcccacta aaataaaacc ttgcatactc cttggtgtca ctttatttct gtttaaggcg    60
ggtaagtcta gctgagtacc ctctcgtact cagggctttg ttcctattgt tgttgcagat   120
ggccagatgt actatggtta ttgcatca                                      148

<210> SEQ ID NO 318
<211> LENGTH: 112
<212> TYPE: DNA
<213> ORGANISM: Saccharum spontaneum

<400> SEQUENCE: 318
tcggaacgtc aaggccaagt acatgagctc tggagcactc agaagccaga catcgatcaa    60
ctcatgttga gccatcagcg agccgtgtcg atccatcaaa caagccgtcc ga           112
```